(12) United States Patent
Bruenker et al.

(10) Patent No.: US 11,525,007 B2
(45) Date of Patent: Dec. 13, 2022

(54) ANTIBODY FAB AND FC VARIANTS

(71) Applicant: Hoffmann-La Roche Inc., Little Falls, NJ (US)

(72) Inventors: Peter Bruenker, Schlieren (CH); Frank Herting, Penzberg (DE); Sylvia Herter, Schlieren (CH); Christian Klein, Schlieren (CH); Ekkehard Moessner, Schlieren (CH); Tilman Schlothauer, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 437 days.

(21) Appl. No.: 16/107,409

(22) Filed: Aug. 21, 2018

(65) Prior Publication Data
US 2019/0106502 A1 Apr. 11, 2019

Related U.S. Application Data

(63) Continuation of application No. PCT/EP2017/054543, filed on Feb. 28, 2017.

(30) Foreign Application Priority Data

Mar. 1, 2016 (EP) .................................... 16158083
Nov. 15, 2016 (EP) .................................... 16198788

(51) Int. Cl.
| | | |
|---|---|---|
| *C07K 16/00* | (2006.01) | |
| *C12P 21/08* | (2006.01) | |
| *A61K 39/395* | (2006.01) | |
| *A61K 39/40* | (2006.01) | |
| *C07K 16/28* | (2006.01) | |
| *A61P 35/00* | (2006.01) | |
| *C07K 1/00* | (2006.01) | |
| *A61K 39/00* | (2006.01) | |

(52) U.S. Cl.
CPC .......... *C07K 16/2887* (2013.01); *A61P 35/00* (2018.01); *C07K 16/00* (2013.01); *A61K 2039/505* (2013.01); *C07K 2317/24* (2013.01); *C07K 2317/51* (2013.01); *C07K 2317/52* (2013.01); *C07K 2317/522* (2013.01); *C07K 2317/53* (2013.01); *C07K 2317/55* (2013.01); *C07K 2317/71* (2013.01); *C07K 2317/73* (2013.01); *C07K 2317/732* (2013.01); *C07K 2317/734* (2013.01); *C07K 2317/92* (2013.01); *C07K 2317/94* (2013.01)

(58) Field of Classification Search
None
See application file for complete search history.

(56) References Cited

U.S. PATENT DOCUMENTS 7,381,560 B2 6/2008 Anderson et al.
2012/0251531 A1 10/2012 Baehner et al.

FOREIGN PATENT DOCUMENTS

| EP | 2 000 149 B1 | 5/2009 |
|---|---|---|
| JP | 2009-505650 A | 2/2009 |
| JP | 2014-514287 | 6/2014 |
| NZ | 588860 A | 3/2012 |
| WO | 2005044859 A2 | 5/2005 |
| WO | 2007/031875 A2 | 3/2007 |
| WO | 2012/130831 A1 | 10/2012 |
| WO | 2014023679 A1 | 2/2014 |

OTHER PUBLICATIONS

Murray et al. Harper's Biochemistry. 23rd Edition. 1993, Chapter 4, pp. 23-28 (Year: 1993).*
Abes et al., "Activating and inhibitory Fcγ receptors in immunotherapy: being the actor or being the target" Expert Rev Clin Immunol 5(6):735-747 ( 2009).
De Reys et al., "Human platelet aggregation by murine monoclonal antiplatelet antibodies is subtype-dependent" Blood 81:1792-1800 (1993).
ISR and Written Opinion of PCT/EP2017/054542 (Completed on Apr. 26, 2017).
ISR and Written Opinion of PCT/EP2017/054543 (Completed on Apr. 26, 2017).
Lesk et al., "Elbow motion in the immunoglobins involves a molecular ball-and-socket joint" Nature 335(8):188-190 ( 2012).
Ludwig et al., "Monoclonal antibody therapeutics and apoptosis" Oncogene 22:9097-9106 ( 2003).
Mossner et al., "Increasing the efficacy of CD20 antibody therapy through the engineering of a new type II anti-CD20 antibody with enhanced direct and immune effector cell-mediated B-cell cytotoxicity" Blood 115(22):4393-4402 ( 2010).
Niederfellner et al., "Epitope Characterization and Crystal Structure of GA101 Provide Insights into the Molecular Basis for Type I/II Distinction of CD20 Antibodies" Blood 118(2):358-367 ( 2011).
Raghavan and Bjorkman, "Fc receptors and their interactions with immunoglobins" Annu Rev Cell Dev Biol 12:181-220 ( 1996).
Ravetch and Bolland, "IgG Fc receptors" Ann Rev Immunol 19:275-290 ( 2001).
Taylor et al., "Thrombosis and shock induced by activating antiplatelet antibodies in human FcγRIIA transgenic mice: the interplay among antibody, spleen, and Fc receptor" Blood 96(13):4254-4260 (Dec. 2000).
WHO Drug Information 2012 vol. 26 No. 4 p. 453.

* cited by examiner

*Primary Examiner* — Chun W Dahle
(74) *Attorney, Agent, or Firm* — Morrison & Foerster LLP

(57) ABSTRACT

The present invention relates to modified antibodies. In particular, the present invention relates to recombinant monoclonal antibodies having altered ability to induce direct cell death and effector function. In addition, the present invention relates to nucleic acid molecules encoding such antibodies, and vectors and host cells comprising such nucleic acid molecules. The invention further relates to methods for producing the antibodies of the invention, and to methods of using these antibodies in treatment of disease.

5 Claims, 6 Drawing Sheets

Specification includes a Sequence Listing.

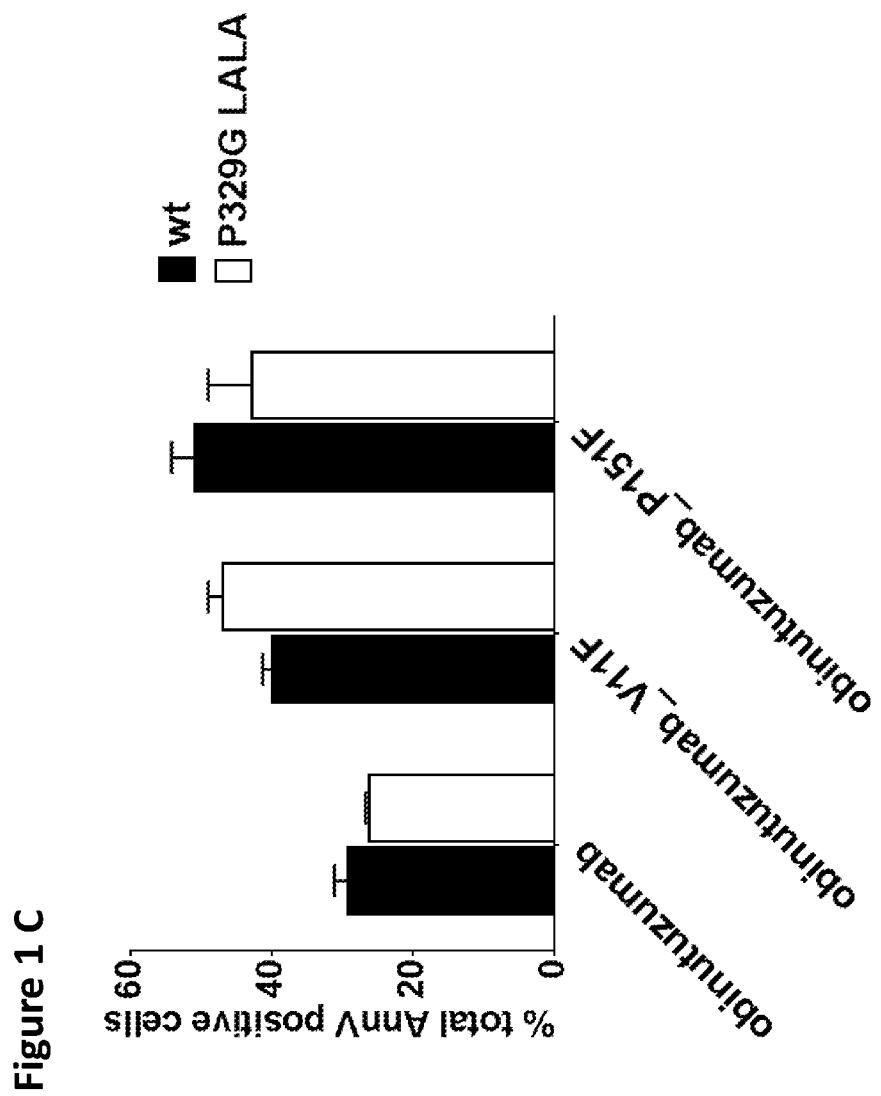

SEQUENCE LISTING

```
<160> NUMBER OF SEQ ID NOS: 22

<210> SEQ ID NO 1
<211> LENGTH: 448
<212> TYPE: PRT
<213> ORGANISM: Artificial Sequence
<220> FEATURE:
<223> OTHER INFORMATION: Description of Artificial Sequence: Synthetic
      chimeric polypeptide
<220> FEATURE:
<223> OTHER INFORMATION: Obinutuzumab heavy chain amino acid sequence
      (SEQ ID NO: 1)

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30
```

-continued

```
Trp Ile Asn Trp Val Arg Gln Ala Pro Gly Gln Gly Leu Glu Trp Met
        35                  40                  45
Gly Arg Ile Phe Pro Gly Asp Gly Asp Thr Asp Tyr Asn Gly Lys Phe
 50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asn Val Phe Asp Gly Tyr Trp Leu Val Tyr Trp Gly Gln Gly
                100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
        180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
        260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
        340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
        420                 425                 430
Ala Leu His Asn His Tyr Thr Gln Lys Ser Leu Ser Leu Ser Pro Gly
        435                 440                 445
```

```
<210> SEQ ID NO 2
<211> LENGTH: 451
<212> TYPE: PRT
<213> ORGANISM: Artificial Sequence
<220> FEATURE:
<223> OTHER INFORMATION: Description of Artificial Sequence: Synthetic
      chimeric polypeptide
<220> FEATURE:
<223> OTHER INFORMATION: Rituximab heavy chain amino acid sequence (SEQ
      ID NO: 2)

<400> SEQUENCE: 2

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

```
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 3
<211> LENGTH: 112
<212> TYPE: PRT
<213> ORGANISM: Mus sp.
<220> FEATURE:
<223> OTHER INFORMATION: Amino acid sequence of variable region of the
      heavy chain (VH) of murine monoclonal anti-CD20 antibody B-Ly1

<400> SEQUENCE: 3

Gly Pro Glu Leu Val Lys Pro Gly Ala Ser Val Lys Ile Ser Cys Lys
1               5                   10                  15

Ala Ser Gly Tyr Ala Phe Ser Tyr Ser Trp Met Asn Trp Val Lys Leu
            20                  25                  30

Arg Pro Gly Gln Gly Leu Glu Trp Ile Gly Arg Ile Phe Pro Gly Asp
        35                  40                  45

Gly Asp Thr Asp Tyr Asn Gly Lys Phe Lys Gly Lys Ala Thr Leu Thr
    50                  55                  60

Ala Asp Lys Ser Ser Asn Thr Ala Tyr Met Gln Leu Thr Ser Leu Thr
65                  70                  75                  80

Ser Val Asp Ser Ala Val Tyr Leu Cys Ala Arg Asn Val Phe Asp Gly
                85                  90                  95

Tyr Trp Leu Val Tyr Trp Gly Gln Gly Thr Leu Val Thr Val Ser Ala
            100                 105                 110

<210> SEQ ID NO 4
<211> LENGTH: 103
<212> TYPE: PRT
<213> ORGANISM: Mus sp.
<220> FEATURE:
<223> OTHER INFORMATION: Amino acid sequence of variable region of the
      light chain (VL) of murine monoclonal anti-CD20 antibody B-Ly1

<400> SEQUENCE: 4

Asn Pro Val Thr Leu Gly Thr Ser Ala Ser Ile Ser Cys Arg Ser Ser
1               5                   10                  15

Lys Ser Leu Leu His Ser Asn Gly Ile Thr Tyr Leu Tyr Trp Tyr Leu
            20                  25                  30

Gln Lys Pro Gly Gln Ser Pro Gln Leu Leu Ile Tyr Gln Met Ser Asn
        35                  40                  45

Leu Val Ser Gly Val Pro Asp Arg Phe Ser Ser Ser Gly Ser Gly Thr
    50                  55                  60

Asp Phe Thr Leu Arg Ile Ser Arg Val Glu Ala Glu Asp Val Gly Val
65                  70                  75                  80
```

Tyr Tyr Cys Ala Gln Asn Leu Glu Leu Pro Tyr Thr Phe Gly Gly Gly
                85                  90                  95

Thr Lys Leu Glu Ile Lys Arg
            100

<210> SEQ ID NO 5
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HH2)

<400> SEQUENCE: 5

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 6
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HH3)

<400> SEQUENCE: 6

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Leu Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HH4)

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ala Phe Ser Tyr Ser
            20                  25                  30

Trp Met Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HH5)

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Met Ser Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Amino acid sequences of variable region of the
    heavy chain (VH) of humanized B-Ly1 antibody (B-HH6)

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Amino acid sequences of variable region of the
    heavy chain (VH) of humanized B-Ly1 antibody (B-HH7)

<400> SEQUENCE: 10

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Ser Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 11
<211> LENGTH: 119

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HH8)

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Tyr Ser
                20                  25                  30

Trp Met Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HH9)

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Tyr Ser
                20                  25                  30

Trp Met Asn Trp Val Arg Gln Ala Pro Gly Gln Gly Leu Glu Trp Met
            35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 13
<211> LENGTH: 119
<212> TYPE: PRT
<213> ORGANISM: Artificial Sequence
<220> FEATURE:
```

<223> OTHER INFORMATION: Description of Artificial Sequence: Synthetic
    polypeptide
<220> FEATURE:
<223> OTHER INFORMATION: Amino acid sequences of variable region of the
    heavy chain (VH) of humanized B-Ly1 antibody (B-HL8)

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Amino acid sequences of variable region of the
    heavy chain (VH) of humanized B-Ly1 antibody (B-HL10)

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ala Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:

<223> OTHER INFORMATION: Amino acid sequences of variable region of the
      heavy chain (VH) of humanized B-Ly1 antibody (B-HL11)

<400> SEQUENCE: 15

```
Gln Val Gln Leu Val Glu Ser Gly Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Val
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HL12)

<400> SEQUENCE: 16

```
Glu Val Gln Leu Val Glu Ser Gly Ala Gly Leu Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HL13)

```
<400> SEQUENCE: 17

Glu Val Gln Leu Val Glu Ser Gly Gly Val Val Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
            35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 18
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HL14)

<400> SEQUENCE: 18

Glu Val Gln Leu Val Glu Ser Gly Gly Gly Leu Lys Lys Pro Gly Gly
1               5                   10                  15

Ser Leu Arg Leu Ser Cys Ala Ala Ser Gly Phe Thr Phe Ser Tyr Ser
            20                  25                  30

Trp Met Asn Trp Val Arg Gln Ala Pro Gly Lys Gly Leu Glu Trp Met
            35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 19
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HL15)

<400> SEQUENCE: 19

Glu Val Gln Leu Val Glu Ser Gly Gly Gly Leu Val Lys Pro Gly Ser
```

-continued

```
                1               5                  10                 15
Ser Leu Arg Leu Ser Cys Ala Ala Ser Gly Phe Thr Phe Ser Tyr Ser
            20                  25                 30

Trp Met Asn Trp Val Arg Gln Ala Pro Gly Lys Gly Leu Glu Trp Met
            35                  40                 45

Gly Arg Ile Phe Pro Gly Asp Gly Asp Thr Asp Tyr Asn Gly Lys Phe
        50                  55                 60

Lys Gly Arg Val Thr Ile Thr Ala Asp Lys Ser Thr Ser Thr Ala Tyr
65                  70                  75                 80

Met Glu Leu Ser Ser Leu Arg Ser Glu Asp Thr Ala Val Tyr Tyr Cys
                85                  90                 95

Ala Arg Asn Val Phe Asp Gly Tyr Trp Leu Val Tyr Trp Gly Gln Gly
                100                 105                110

Thr Leu Val Thr Val Ser Ser
        115
```

<210> SEQ ID NO 20
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HL16)

<400> SEQUENCE: 20

```
Glu Val Gln Leu Val Glu Ser Gly Gly Gly Leu Val Lys Pro Gly Gly
1               5                   10                 15

Ser Leu Arg Val Ser Cys Ala Ala Ser Gly Phe Thr Phe Ser Tyr Ser
            20                  25                 30

Trp Met Asn Trp Val Arg Gln Ala Pro Gly Lys Gly Leu Glu Trp Met
            35                  40                 45

Gly Arg Ile Phe Pro Gly Asp Gly Asp Thr Asp Tyr Asn Gly Lys Phe
        50                  55                 60

Lys Gly Arg Val Thr Ile Thr Ala Asp Lys Ser Thr Ser Thr Ala Tyr
65                  70                  75                 80

Met Glu Leu Ser Ser Leu Arg Ser Glu Asp Thr Ala Val Tyr Tyr Cys
                85                  90                 95

Ala Arg Asn Val Phe Asp Gly Tyr Trp Leu Val Tyr Trp Gly Gln Gly
                100                 105                110

Thr Leu Val Thr Val Ser Ser
        115
```

<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      heavy chain (VH) of humanized B-Ly1 antibody (B-HL17)

<400> SEQUENCE: 21

```
Glu Val Gln Leu Val Glu Ser Gly Gly Gly Leu Val Lys Pro Gly Gly
1               5                   10                 15

Ser Leu Arg Leu Ser Cys Ala Ala Ser Gly Phe Thr Phe Ser Tyr Ser
```

```
                    20                  25                  30
Trp Met Asn Trp Val Arg Gln Ala Pro Gly Lys Gly Leu Glu Trp Met
        35                  40                  45

Gly Arg Ile Phe Pro Gly Asp Gly Asp Thr Asp Tyr Asn Gly Lys Phe
        50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
                100                 105                 110

Thr Leu Val Thr Val Ser Ser
            115

<210> SEQ ID NO 22
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Amino acid sequences of variable region of the
      light chain (VL) of humanized B-Ly1 antibody B-KV1

<400> SEQUENCE: 22

Asp Ile Val Met Thr Gln Thr Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Val Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
                100                 105                 110

Arg Thr Val
        115
```

1

ANTIBODY FAB AND FC VARIANTS

CROSS REFERENCE TO RELATED APPLICATIONS

This application is a continuation of, and claims priority to, International Patent Application No. PCT/EP2017/054543 filed on Feb. 28, 2017, which claims priority to European Patent Application No. 16158083.2, filed on Mar. 1, 2016 and European Patent Application No. 16198788.8, filed on Nov. 15, 2016. The entire contents of each of the above patent applications are hereby incorporated by reference.

SEQUENCE LISTING

The instant application contains a Sequence Listing which has been filed electronically in ASCII format and is hereby incorporated by reference in its entirety. Said ASCII copy, created on Sep. 18, 2018, is named P33405-US_SL.txt and is 33,879 bytes in size.

FIELD OF THE INVENTION

The present invention relates to modified antibodies. In particular, the present invention relates to recombinant monoclonal antibodies having altered ability to induce direct cell death and effector function. In addition, the present invention relates to nucleic acid molecules encoding such antibodies, and vectors and host cells comprising such nucleic acid molecules. The invention further relates to methods for producing the antibodies of the invention, and to methods of using these antibodies in treatment of disease.

BACKGROUND

Antibodies, also called immunoglobulins, have a basic structure comprising four polypeptide chains: two identical heavy (H) chains paired with two identical light (L) chains. Each heavy and light chain comprises a variable region (VH and VL, respectively) and a constant region (CH and CL, respectively). The CH region has 3 domains (CH1, CH2, and CH3), while the smaller CL region has only one domain (simply referred to as CL). Each VH and VL region comprises 3 complementarity determining regions (CDRs) flanked by 4 framework regions in the following order: FR1-CDR1-FR2-CDR2-FR3-CDR3-FR4. The CDRs are the most variable part of the V region, and determine the antigen specificity of the antibody. Together, a paired VH and VL region form the antigen binding site, and bivalent antibodies have two such antigen binding sites. It should be noted that this basic antibody structure can be modified in various ways (e.g., by generating fragments of the structure) while still retaining or even improving desired functions and/or antigen binding activity.

The pharmaceutical use of antibodies, especially in the field of cancer therapy, has tremendously increased over the past years. Examples of monoclonal antibodies approved for human cancer therapy are RITUXAN®/MABTHERA® (rituximab), HERCEPTIN© (trastuzumab), AVASTIN© (BEVACIZUMAB) and GAZYVA©/GAZYVARO© (obinutuzumab). In addition to mediating effector functions such as antibody-dependent cell-mediated cytotoxicity (ADCC), antibody-dependent cellular phagocytosis (ADCP) and complement dependent cytotoxicity (CDC), such monoclonal antibodies can modulate cellular functions by inducing or inhibiting cell signaling activity. For example, monoclonal antibodies have been shown to mediate antigen cross-linking, activate death receptors (e.g., by facilitating oligomerization of receptors or mimicking ligand binding), and blocking of ligand-mediated cell signaling in cell growth differentiation, and/or proliferation pathways (see, e.g., Ludwig et al, Oncogene (2003) 22: 9097-9106). In contrast to Fc mediated effector functions induction of apoptosis or direct cell death mediated by monoclonal antibodies is much less understood. The orientation of the variable domains of e.g. IgG type antibodies seem to play a crucial role regarding antibody mediated induction of direct cell death.

The interface between the VH and CH1 domains comprises conserved amino acids (see e.g., Lesk and Chothia, Nature (1988) 335(8):188-190). The area of contact can be described as a "molecular ball-and-socket joint". This joint determines the "elbow motion" and also the so called "elbow angle" of the VH and VL regions with respect to the CH1 and CL regions, and prevents a rigid contact from forming between the V and C regions (Lesk and Chothia, Nature (1988) 335(8): 188-190)). The "socket" of this ball-and-socket joint is formed by amino acid residues in the VH framework region whereas the "ball" is formed by amino acid residues in the CH1 domain. Differences in the amino acids at these positions can dictate the elbow angle that is formed between the V and C regions, and therefore the orientation of the VH-VL dimer (see Lesk and Chothia, Nature (1988) 335(8): 188-190). Conformational alterations of the elbow angle have been identified to be responsible for significant changes in binding behavior of the antibody/antigen interaction without changing overall affinity.

Direct cell death can be triggered by several different mechanisms. For example, the activation of signaling pathways through cell membrane-bound "death receptors", e.g., members of the tumor necrosis factor receptor (TNFR) superfamily, can lead to induction of direct cell death. Likewise, dimerization or cross-linking of surface antigen, e.g., CD20, can also induce direct cell death (see, e.g., Ludwig et al, Oncogene (2003) 22: 9097-9106).

There remains a need for enhanced monoclonal antibodies with improved therapeutic potential for human therapy. Specifically targeting signaling pathways with monoclonal antibodies is very challenging, but modulating antigens associated with cell signaling, including, but not limited to, the induction of direct cell death, is much needed for improved cancer therapy, including, but not limited to, humans.

SUMMARY OF THE INVENTION

There remains a need for monoclonal antibodies with improved therapeutic potential for human therapy. Targeting signaling pathways with monoclonal antibodies is very challenging, but modulating antigens associated with cell signaling, including, but not limited to, the induction of direct cell death, is much needed for improved cancer therapy. Unexpectedly, the present inventors found that mutations in the elbow hinge region at the amino acid positions as disclosed herein lead to altered (increases or decreased) induction of direct cell death. Surprisingly, these mutations can be combined with mutations in the Fc part of the antibodies as disclosed herein, leading to reduced or ablated effector function. In combination, the modifications as disclosed herein allow a selective and independent modulation of induction of direct cell death and/or effector function as compared to non-modified parent antibodies.

Accordingly, the invention provides an antibody comprising a variant heavy chain region comprising at least one amino acid substitution relative to the parent non-substituted heavy chain region, wherein the heavy chain region of the parent non-substituted antibody comprises at least one of the amino acid residues selected from the group consisting of Val11, Leu11 and Pro151, and wherein said substitution is at one of said amino acid residues selected from the group consisting of Val11, Leu11 and Pro151, wherein direct cell death induced by the antibody comprising the variant heavy chain region is altered compared to direct cell death induced by the antibody comprising the parent non-substituted heavy chain region. In another aspect of the invention at least one of the amino acid residues selected from the group consisting of Val11, Leu11 and Pro151 is substituted with at least one of the amino acid residues selected from the group consisting of alanine, glycine, phenylalanine, threonine and tryptophan.

In a specific aspect of the invention said parent non-substituted antibody is an anti-CD20 antibody. In another specific aspect of the invention the parent non-substituted antibody is a type I anti-CD20 antibody. In yet another specific aspect of the invention the parent non-substituted antibody is a type II anti-CD20 antibody. In a specific aspect of the invention the parent non-substituted antibody is obinutuzumab. In yet another specific aspect of the invention the parent non-substituted antibody is rituximab.

Another aspect of the invention is an antibody as disclosed herein, wherein direct cell death induced by the antibody comprising the variant heavy chain region is increased compared to direct cell death induced by the antibody comprising the parent non-substituted heavy chain region. Yet another aspect of the invention is an antibody as disclosed herein, wherein direct cell death induced by the antibody comprising the variant heavy chain region is decreased compared to direct cell death induced by the antibody comprising the parent non-substituted heavy chain region.

A specific aspect of the invention is the antibody disclosed herein, wherein at least one of the amino acid residues selected from the group consisting of Val11, Leu11 and Pro151 is substituted with at least one of the amino acid residues selected from the group consisting of alanine and glycine, wherein direct cell death induced by the antibody comprising the variant heavy chain region is decreased compared to direct cell death induced by the antibody comprising the parent non-substituted heavy chain region. Another specific aspect of the invention is the antibody disclosed herein, wherein at least one of the amino acid residues selected from the group consisting of Val11, Leu11 and Pro151 is substituted with at least one of the amino acid residues selected from the group consisting of phenylalanine, threonine and tryptophan, wherein direct cell death induced by the antibody comprising the variant heavy chain region is increased compared to direct cell death induced by the antibody comprising the parent non-substituted heavy chain region. Yet another aspect of the invention is an antibody as disclosed herein, comprising said at least one substitution at an amino acid residue selected from the group consisting of Val11, Leu11 and Pro151, further comprising at least one additional amino acid substitution in the heavy chain region, wherein the parent non-substituted heavy chain region comprises the amino acid residues Leu234, Leu235 and Pro329, wherein the variant heavy chain region comprises at least one of the amino acid substitutions Leu234Ala, Leu235Ala and Pro329Gly relative to the parent non-substituted heavy chain region, and wherein binding to FcγR and C1q is abolished, wherein Fc-mediated effector function is abolished.

Yet another aspect of the invention is an antibody comprising a variant heavy chain region comprising an amino acid substitution relative to the parent non-substituted heavy chain region, wherein the heavy chain region of the parent non-substituted antibody comprises the amino acid residue Pro151, wherein the residues are numbered according to the EU index as in Kabat, and wherein said substitution is at said amino acid residue Pro151, wherein direct cell death induced by the antibody comprising the variant heavy chain region is altered compared to direct cell death induced by the antibody comprising the parent non-substituted heavy chain region. Another aspect of the invention is the antibody as disclosed herein, wherein Pro151 is substituted with alanine, wherein direct cell death induced by the antibody comprising the variant heavy chain region is decreased compared to direct cell death induced by the antibody comprising the parent non-substituted heavy chain region. Another aspect of the invention is the antibody as disclosed herein, wherein Pro151 is substituted with phenylalanine, wherein direct cell death induced by the antibody comprising the variant heavy chain region is increased compared to direct cell death induced by the antibody comprising the parent non-substituted heavy chain region. Another aspect of the invention is the antibody as disclosed herein comprising a variant heavy chain region comprising a further amino acid substitution relative to the parent non-substituted heavy chain region, wherein the heavy chain region of the parent non-substituted antibody comprises the amino acid residue Val11, wherein the residues are numbered according to Kabat numbering, and wherein said further substitution is at said amino acid residue Val11, wherein direct cell death induced by the antibody comprising the variant heavy chain region is altered compared to direct cell death induced by the antibody comprising valine at position Val11. Yet another aspect of the invention is an antibody comprising a variant heavy chain region comprising at least one amino acid substitution relative to the parent non-substituted heavy chain region, wherein the heavy chain region of the parent non-substituted antibody comprises the amino acid residue Val11, wherein the residues are numbered according to Kabat numbering, and wherein said substitution is at said amino acid residue Val11, and wherein direct cell death induced by the antibody comprising the variant heavy chain region is altered compared to direct cell death induced by the antibody comprising the parent non-substituted heavy chain region. Another aspect of the invention is the antibody as disclosed herein, wherein Val11 is substituted with an amino acid selected from the group consisting of alanine and glycine, and wherein direct cell death induced by the antibody comprising the variant heavy chain region is decreased compared to direct cell death induced by the antibody comprising valine at position Val11. Another aspect of the invention is the antibody as disclosed herein, wherein Val11 is substituted with an amino acid selected from the group consisting of phenylalanine, threonine and tryptophan, and wherein direct cell death induced by the antibody comprising the variant heavy chain region is increased compared to direct cell death induced by the antibody comprising valine at position Val11. Yet another aspect of the invention is an antibody as disclosed herein, comprising said at least one amino acid substitution in the heavy chain region, further comprising at least one additional amino acid substitution in the heavy chain region, wherein the parent non-substituted heavy chain region comprises the amino acid residues Leu234, Leu235 and Pro329, wherein the residues are numbered according to the EU index as in Kabat, wherein the variant heavy chain region comprises the amino acid substitutions Leu234Ala, Leu235Ala and Pro329Gly relative to the parent non-substituted heavy chain region, and wherein binding to FcγR and C1q is abolished, wherein Fc-mediated effector function is abolished.

Another aspect of the invention is the antibody as disclosed herein with an amount of fucose of 60% or less of the total amount of oligosaccharides (sugars) at the amino acid residue Asn297 in the heavy chain region.

Another aspect of the invention is the antibody as disclosed herein, wherein the antibody specifically binds to CD20. In a specific aspect of the invention, said antibody binds to CD20 with a dissociation constant (Kd) on cells of 10 nM or less as determined by scatchard analysis.

Another aspect of the invention is a polynucleotide encoding a variant heavy chain region of an antibody as disclosed herein. Another aspect of the invention is a polynucleotide encoding a light chain region of an antibody as disclosed herein. Yet another aspect of the invention is a vector comprising at least one of the polynucleotides as disclosed herein. Another aspect of the invention is a polycistronic vector comprising the polynucleotides as disclosed herein.

Another aspect of the invention is a host cell comprising the vector or a polynucleotide as disclosed herein. Yet another aspect of the invention is a host cell as disclosed herein, wherein said host is engineered to express at least one nucleic acid encoding a polypeptide having β(1,4)-N-acetylglucosaminyltransferase III activity. Yet another aspect of the invention is a host cell as disclosed herein, wherein said polypeptide having β(1,4)-N-acetylglucosaminyltransferase III activity is a fusion polypeptide further comprising the Golgi localization domain of a heterologous Golgi resident polypeptide. Yet another aspect of the invention is a host cell as disclosed herein, wherein said Golgi localization domain is selected from the localization domain of mannosidase II, the localization domain of β(1,2)-N-acetylglucosaminyltransferase I, the localization of β(1,2)-N-acetylglucosaminyltransferase II, the localization domain of mannosidase I, and the localization of α1-6 core fucosyltransferase.

Another aspect of the invention is a method for the production of an antibody as disclosed herein comprising (i) culturing the host cell as disclosed herein under conditions permitting the expression of said at least one polynucleotide; and (ii) recovering said antibody from the culture medium.

Another aspect of the invention is a pharmaceutical composition comprising an antibody as disclosed herein and a pharmaceutically acceptable carrier. Yet another aspect of the invention is an antibody as disclosed herein for use as a medicament. Yet another aspect of the invention is an antibody as disclosed herein for use in treating a disease selected from the group consisting of proliferative disorder and autoimmune disease.

Another aspect of the invention is an antibody as disclosed herein, characterized in that said proliferative disorder is a CD20 expressing cancer. Yet another aspect of the invention is an antibody as disclosed herein, characterized in that said cancer is selected from the group consisting of lymphoma and lymphocytic leukemia. Yet another aspect of the invention is an antibody as disclosed herein, characterized in that said autoimmune disease is selected from the group consisting of rheumatoid arthritis, lupus, multiple sclerosis, Sjögren's syndrome and transplant rejection.

Another aspect of the invention is a method of treating a disease selected from the group consisting of proliferative disorder and autoimmune disease comprising administering to an individual an effective amount of the antibody as disclosed herein. Another aspect of the invention is the method of treating as disclosed herein, characterized in that said proliferative disorder is a CD20 expressing cancer. Yet another aspect of the invention is the method of treating as disclosed herein, characterized in that said cancer is selected from the group consisting of lymphoma and lymphocytic leukemia. Yet another aspect of the invention is a method of treating an individual having an autoimmune disease comprising administering to an individual an effective amount of the antibody as disclosed herein, characterized in that said autoimmune disease is selected from the group consisting of rheumatoid arthritis, lupus, multiple sclerosis, Sjögren's syndrome and transplant rejection.

Figure 1:
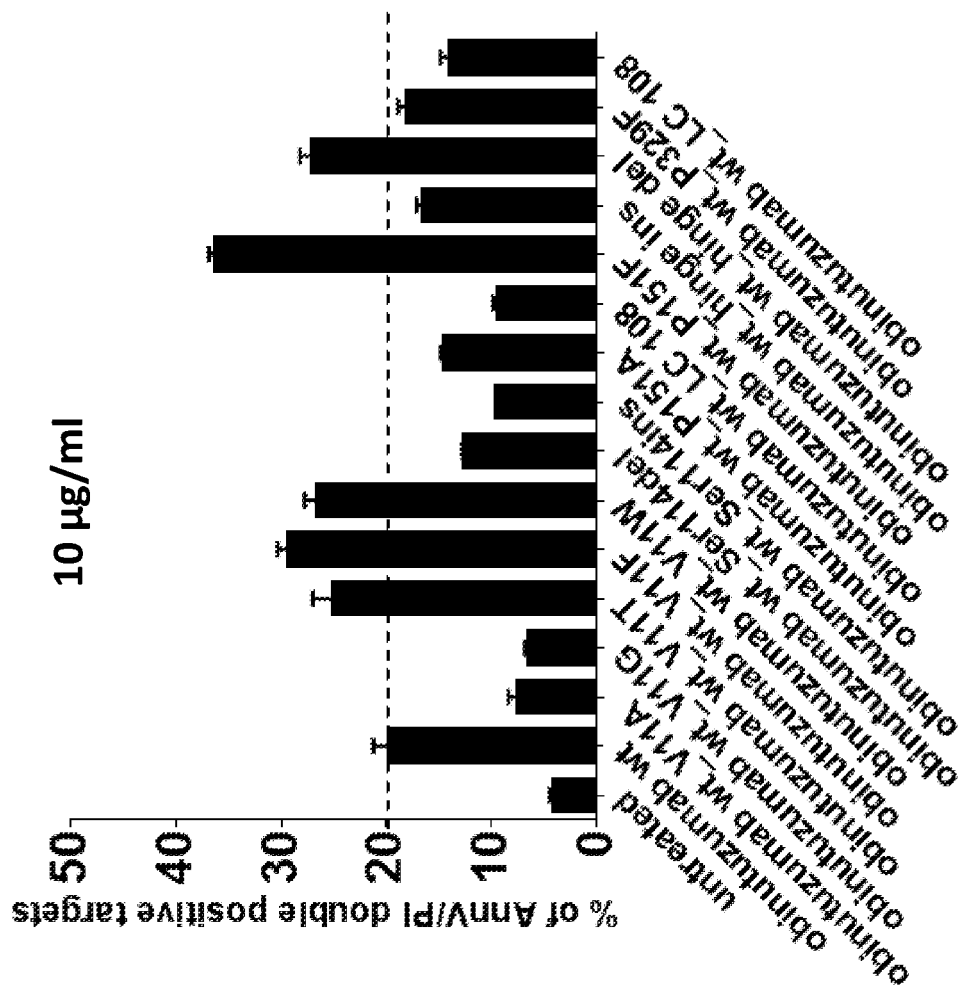
FIG. 1A and FIG. 1B
Figure 1:
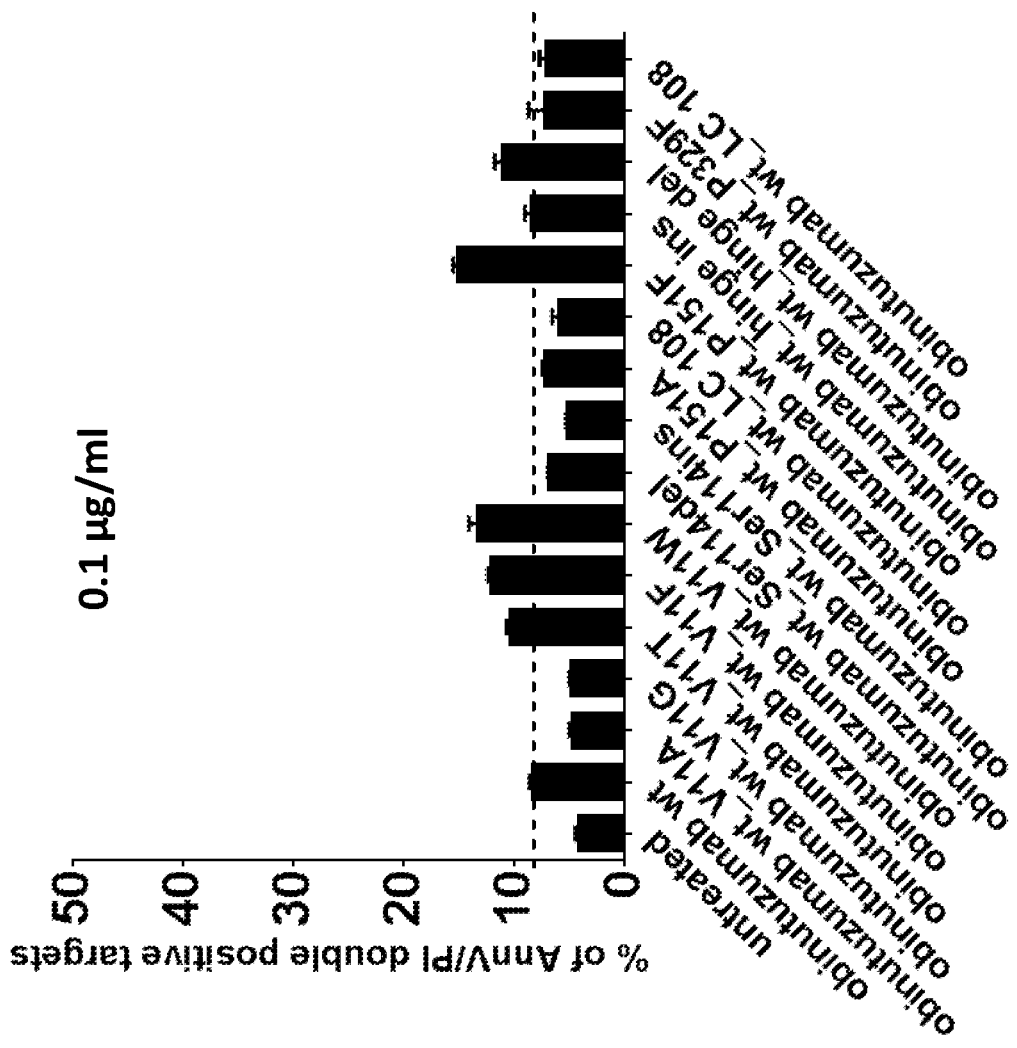
Figure 1:
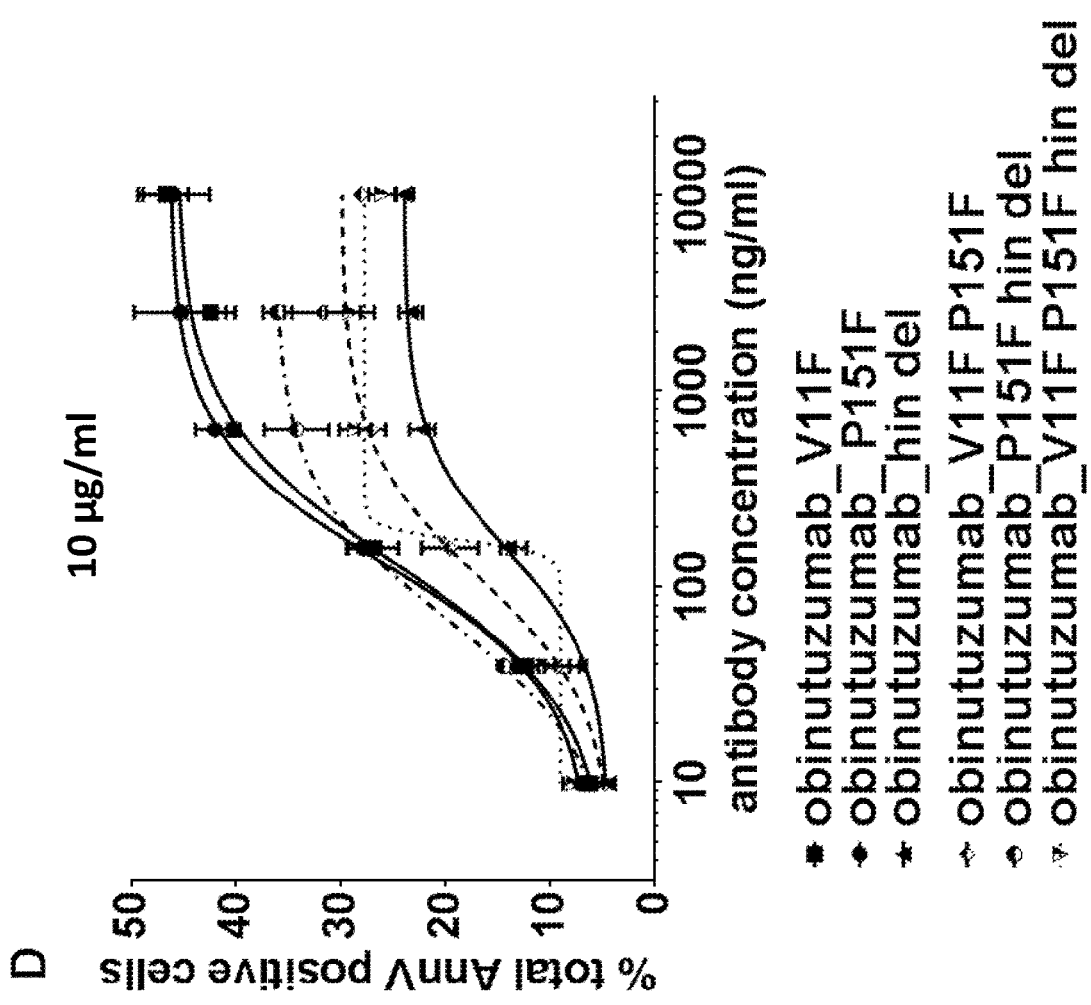

Induction of direct cell death by CD20 antibody (obinutuzumab, GA101) variants as measured by Annexin V binding and PI staining was determined using CD20-expressing mantle cell lymphoma (Z-138).

a) FIG. 1A: GA101 variants (GA101-wildtype, GA101-V11A, GA101-V11G, GA101-V11T, GA101-V11F, GA101-V11W, GA101-Ser114del, GA101-Ser114ins, GA101-P151A, GA101-LC 108, GA101-P151F, GA101-hinge ins, GA101-hinge del, GA101-P329F) were tested at an antibody concentration of 10 μg/ml;

b) FIG. 1B: GA101 variants (GA101-wildtype, GA101-V11A, GA101-V11G, GA101-V11T, GA101-V11F, GA101-V11W, GA101-Ser114del, GA101-Ser114ins, GA101-P151A, GA101-LC 108, GA101-P151F, GA101-hinge ins, GA101-hinge del, GA101-P329F) were tested at an antibody concentration of 0.1 μg/ml;

c) FIG. 1C: GA101 Fab variants (GA101-wildtype, GA101-V11F and GA101-P151F) and combined Fab/Fc variants (GA101-P329G L234A L235A, GA101-V11F P329G L234A L235A, GA101-P151F P329G L234A L235A and GA101-hinge del P329G L234A L235A) were compared for induction of direct cell death;

d) FIG. 1D: Fab variants (V11F, P151F and hinge del) and combined Fab variants (V11F P151F, P151F hinge del and V11F P151F hinge del) both on a GA101 P329G L234A L235A backbone were compared for induction of direct cell death.

FIG. 2

B cell depletion induced by obinutuzumab variants (GA101-wildtype, GA101-P329G L234A L235A, GA101-V11F P329G L234A L235A and GA101-P151F P329G L234A L235A) was measured by counting CD20/CD19 positive cells. Human whole blood was incubated with antibody variants at different concentrations and for one or two days, respectively.

FIG. 3

Concentration-time profile for GA101-V11F P329G L234A L235A, GA101-P151F P329G L234A L235A and GA101-P329G L234A L235A in SCID beige mice.

DETAILED DESCRIPTION OF EMBODIMENTS OF THE INVENTION

I. Definitions

Terms are used herein as generally used in the art, unless otherwise defined as follows and herein.

The term "heavy chain", "heavy chain domain" and "heavy chain region" are used interchangeably herein and refer to a polypeptide chain which essentially consists of the heavy chain of an immunoglobulin heavy chain or fragments thereof retaining the same functionality compared to the immunoglobulin heavy chain. In the present specification and claims, the numbering of the residues in an immunoglobulin heavy chain is that of Kabat et al., Sequences of Proteins of Immunological Interest, 5th Ed. Public Health Service, National Institutes of Health, Bethesda, Md. (1991), hereby expressly incorporated by reference in its entirety. Kabat et al. defined inter alia, a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., Sequences of Proteins of Immunological Interest, 5th Ed. Public Health Service, National Institutes of Health, Bethesda, Md. (1991) for variable domain sequences. Unless stated otherwise herein, references to residue number 11 of a heavy chain region means residue numbering by the Kabat numbering system (Kabat numbering). The "EU numbering" system or "EU index as in Kabat" can be used when referring to a residue in an immunoglobulin heavy chain constant region. The EU index as in Kabat refers to the residue numbering of the human IgG1 EU antibody. The numbering of residues may be determined for a given antibody by alignment at regions of homology of the sequence of the antibody with a "standard" Kabat numbered sequence. Unless stated otherwise herein, references to residue numbers 151, 234, 235, 297 and 329 of a heavy chain region means residue numbering by the EU numbering system (EU numbering) set forth by Kabat et al., Sequences of Proteins of Immunological Interest, 5th Ed. Public Health Service, National Institutes of Health, Bethesda, Md. (1991). Examples of two anti-CD20 antibodies numbered according to Kabat (Kabat numbering or EU numbering), in particular positions 11 (Kabat numbering), 151 (EU numbering), 234 (EU numbering), 235 (EU numbering), 329 (EU numbering) are included herein (SEQ ID NO: 01, SEQ ID NO: 02).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those disclosed herein. Specific illustrative embodiments for measuring binding affinity are disclosed herein.

An "affinity matured" antibody refers to an antibody with one or more alterations in one or more hypervariable regions (HVRs), compared to a parent antibody which does not possess such alterations, such alterations resulting in an improvement in the affinity of the antibody for its antigen.

The term "afucosylated antibody" refers to an antibody of IgG1 or IgG3 isotype (preferably of IgG1 isotype) with an altered pattern of glycosylation in the Fc region at Asn297 having a reduced level of fucose residues. Glycosylation of human IgG1 or IgG3 occurs at Asn297 as core fucosylated bianntennary complex oligosaccharide glycosylation terminated with up to 2 Gal residues. These structures are designated as G0, G1 ($\alpha$1,6 or $\alpha$1,3) or G2 glycan residues, depending from the amount of terminal Gal residues (Raju, T. S., BioProcess Int. 1 (2003) 44-53). CHO type glycosylation of antibody Fc parts is e.g. described by Routier, F. H., Glycoconjugate J. 14 (1997) 201-207. Antibodies which are recombinantly expressed in non glycomodified CHO host cells usually are fucosylated at Asn297 in an amount of at least 85%. It should be understood that the term an afucosylated antibody as used herein includes an antibody having no fucose in its glycosylation pattern. It is commonly known that typical glycosylated residue position in an antibody is the asparagine at position 297 according to the EU numbering system ("Asn297"). Thus an afucosylated antibody according to the invention means an antibody of IgG1 or IgG3 isotype (preferably of IgG1 isotype) wherein the amount of fucose is 60% or less of the total amount of oligosaccharides (sugars) at Asn297 (which means that at least 40% or more of the oligosaccharides of the Fc region at Asn297 are afucosylated).

As used herein, the term "agonist activity" is intended to refer to activity of an agent (e.g., an antigen binding molecule) when it interacts with (for example, binds to) a molecule associated with a cell surface and initiates or induces a reaction.

As used herein, the term "altered cell signaling activity" is intended to refer to an increase or decrease in the ability of an antibody to induce or inhibit cell signaling activity of a target antigen.

As used herein, the term "altered cross-linking of one or more target antigens" is intended to refer to an increase or decrease in the ability of an antibody to bring into closer proximity to each other, and/or into closer proximity with other membrane-associated molecules, and/or into a more favorable conformation for interaction target antigens that are capable of forming complexes (e.g., through cross-linking of proteins, or oligomerization of membrane-associated receptors) to initiate cell signaling activity.

As used herein, the term "altered induction of direct cell death" is intended to refer to an increase or decrease in the ability of an antibody to induce direct cell death.

As used herein, "amino acid substitution" is intended to refer to replacing one or more amino acids in a reference sequence (e.g., a parent molecule, such as an antibody). In one embodiment, amino acid substitution may be achieved by, for example, a point mutation in the sequence of a nucleic acid encoding a polypeptide as compared to a parent non-substituted sequence. In another embodiment, substitution of an amino acid residue may be achieved by replacing the entire framework region of the parent polypeptide with, for example, a framework region from a germline CH1 sequence that comprises the desired amino acid at the position to be substituted in reference to the parent.

As used herein, the term "antagonist activity" is intended to refer to activity of an agent (e.g., an antigen binding molecule) when it interacts with (for example, binds to) a molecule on a cell and prevents initiation or induction of a reaction or discontinues an ongoing reaction.

As used herein, the term "antibody" is intended to include whole antibody molecules, including monoclonal, polyclonal and multispecific (e.g., bispecific) antibodies, as well as antibody fragments retaining binding specificity, and fusion proteins that include a region equivalent to the heavy chain region of an immunoglobulin and that retain binding specificity. Also encompassed are "antibody fragments" that retain binding specificity including, but not limited to, VH fragments, VL fragments, Fab fragments, F(ab')$_2$ fragments, scFv fragments, Fv fragments, minibodies, diabodies, triabodies, and tetrabodies (see, e.g., Hudson and Souriau, Nature Med. 9: 129-134 (2003), hereby incorporated by reference in its entirety). Also encompassed are humanized, primatized and chimeric antibodies. As used herein, "whole antibody" refers to an immunoglobulin molecule comprising two "heavy chains" and two "light chains", each of which comprises a variable and constant region. As used herein, the term "modified antibody" is intended to refer to an antibody comprising at least one amino acid residue substitution in the heavy chain variable region and/or CH1 region and/or at least one amino acid residue substitution in the light chain variable region and/or CL region and/or at least one amino acid substitution in the Fc region.

An antibody "which binds" an antigen of interest, e.g. a tumor-associated polypeptide antigen target, is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of about $10^{-4}$ M or less, alternatively about $10^{-5}$ M or less, alternatively about $10^{-6}$ M or less, alternatively about $10^{-7}$ M or less, alternatively about $10^{-8}$ M or less, alternatively about $10^{-9}$ M or less, alternatively about $10^{-10}$ M or less, alternatively about $10^{-11}$ M or less, alternatively about $10^{-12}$ M or less, or less. In one embodiment, the term "specific binding" refers to binding where a molecule binds to a particular polypeptide or epitope on a particular polypeptide without substantially binding to any other polypeptide or polypeptide epitope.

The terms "anti-CD20 antibody" and "an antibody that specifically binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured by a radioimmunoassay (RIA). In certain embodiments, an antibody that binds to CD20 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M) as measured by scatchard analysis. In certain embodiments, an anti-CD20 antibody binds to an epitope of CD20 that is conserved among CD20 from different species. Depending on binding properties and biological activities of anti-CD20 antibodies to the CD20 antigen, two types of anti-CD20 antibodies (type I and type II anti-CD20 antibodies) can be distinguished according to Cragg, M. S., et al., Blood 103 (2004) 2738-2743; and Cragg, M. S., et al., Blood 101 (2003) 1045-1052, see Table 1.

TABLE 1

Properties of Type I and Type II anti-CD20 Antibodies

| Type I anti-CD20 antibodies | Type II anti-CD20 antibodies |
|---|---|
| Type I CD20 epitope | Type II CD20 epitope |
| Localize CD20 to lipid rafts | Do not localize CD20 to lipid rafts |
| Increased CDC (if IgG1 isotype) | Decreased CDC (if IgG1 isotype) |
| ADCC activity (if IgG1 isotype) | ADCC activity (if IgG1 isotype) |
| Full binding capacity | Reduced binding capacity |
| Homotypic aggregation | Stronger homotypic aggregation |

One essential property of type I and type II anti-CD20 antibodies is their mode of binding. Thus type I and type II anti-CD20 antibody can be classified by the ratio of the binding capacities to CD20 on Raji cells (ATCC-No. CCL-86) of said anti-CD20 antibody compared to rituximab.

An antibody which "induces direct cell death" or "induces apoptosis" or "induces apoptosis-like direct cell death" is one which induces programmed cell death as determined by binding of annexin V, cell shrinkage, dilation of endoplasmic reticulum, cell fragmentation, and/or formation of membrane vesicles (called apoptotic bodies). The cell is usually one which expresses a CD20 polypeptide. Preferably the cell is a tumor cell. More preferably the cell is a hematopoietic cell, such as a malignant B cell or a B cell involved in autoimmunity. Various methods are available for evaluating the cellular events associated with direct cell death. For example, phosphatidyl serine (PS) translocation can be measured by annexin binding.

An antibody which "induces cell death" is one which causes a viable cell to become nonviable. The cell is one which expresses a CD20 polypeptide and is of a cell type which specifically expresses or overexpresses a CD20 polypeptide. The cells may be cancerous or normal cells of the particular cell type. The cell may be a normal B cell involved in autoimmunity. The cell may be a cancer cell. Preferably the cell is a malignant B cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue (see Moore et al. Cytotechnology 17:1-11 (1995)) or 7AAD can be assessed relative to untreated cells. Preferred cell death-inducing antibodies are those which induce PI uptake in the PI uptake assay in BT474 cells.

By "antibody having altered antibody-dependent cell-mediated cytotoxicity" ("ADCC") is meant an antibody, as that term is defined herein, having altered ADCC as determined by any suitable method known to those of ordinary skill in the art. One accepted in vitro ADCC assay is as follows:

1) the assay uses target cells that are known to express the target antigen recognized by the antigen-binding region of the antibody;

2) the assay uses human peripheral blood mononuclear cells (PBMCs), isolated from blood of a randomly chosen healthy donor, as effector cells;

3) the assay is carried out according to the following protocol:

i) the PBMCs are isolated using standard density centrifugation procedures and are suspended at $5 \times 10^6$ cells/ml in RPMI cell culture medium;

ii) the target cells are grown by standard tissue culture methods, harvested from the exponential growth phase with a viability higher than 90%, washed in RPMI cell culture medium, labeled with 100 micro-Curies of $^{51}Cr$, washed twice with cell culture medium, and resuspended in cell culture medium at a density of $10^5$ cells/ml;

iii) 100 microliters of the final target cell suspension above are transferred to each well of a 96-well microtiter plate;

iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;

v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);

vi) for the spontaneous release (SR) controls, 3 additional wells in the plate containing the labeled target cells, receive 50 microliters of RPMI cell culture medium instead of the antibody solution (point iv above);

vii) the 96-well microtiter plate is then centrifuged at 50×g for 1 minute and incubated for 1 hour at 4° C.;

viii) 50 microliters of the PBMC suspension (point i above) are added to each well to yield an effector:target cell ratio of 25:1 and the plates are placed in an incubator under 5% $CO_2$ atmosphere at 37° C. for 4 hours;

ix) the cell-free supernatant from each well is harvested and the experimentally released radioactivity (ER) is quantified using a gamma counter;

x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

4) "increased ADCC" is defined as either an increase in the maximum percentage of specific lysis observed within the antibody concentration range tested herein, and/or a reduction in the concentration of antibody required to achieve one half of the maximum percentage of specific lysis observed within the antibody concentration range tested herein. The increase in ADCC is relative to the ADCC, measured with the above assay, mediated by the same antibody, produced by the same type of host cells, using the same standard production, purification, formulation and storage methods, which are known to those skilled in the art, but that has not been modified by amino acid substitution or glycoengineering. Thus, "decreased ADCC" is defined as either a decrease in the maximum percentage of specific lysis observed within the antibody concentration range tested herein, and/or an increase in the concentration of antibody required to achieve one half of the maximum percentage of specific lysis observed within the antibody concentration range tested herein. The decrease in ADCC is relative to the ADCC, measured with the above assay, mediated by the same antibody, produced by the same type of host cells, using the same standard production, purification, formulation and storage methods, which are known to those skilled in the art, but that has not been modified by amino acid substitution or glycoengineering.

As used herein, the term "apoptosis" is intended to refer to programmed cell death, which is characterized by certain cellular events such as nuclear fragmentation and/or formation of apoptotic bodies by condensation of cytoplasm, plasma membranes and/or organelles.

As used herein, the term "binding" or "specifically binding" refers to the binding of the antibody to an epitope of the tumor antigen in an in vitro assay. The in vitro assay can be a plasmon resonance assay (BIAcore, GE-Healthcare Uppsala, Sweden) with purified wild-type antigen. For anti-CD20 antibodies the in vitro assay is preferably a scatchard analysis. The affinity of the binding is defined by the term KD. Binding or specifically binding means a binding affinity (KD) of $10^{-8}$ M or less, preferably $10^{-8}$ M to $10^{-13}$ M (in one embodiment $10^{-9}$ M to $10^{-13}$ M). Thus, an afucosylated antibody according to the invention is specifically binding to the tumor antigen with a binding affinity (KD) of $10^{-8}$ mol/l or less, preferably $10^{-8}$ M to $10^{-13}$ M (in one embodiment $10^{-9}$ M to $10^{-13}$ M).

The term "CD20," as used herein, refers to any native CD20 from any vertebrate source, including mammals such as primates (e.g. humans) and rodents (e.g., mice and rats), unless otherwise indicated. The term encompasses "full-length" unprocessed CD20 as well as any form of CD20 that results from processing in the cell. The term also encompasses naturally occurring variants of CD20, e.g., splice variants or allelic variants. CD20 (also known as B-lymphocyte antigen CD20, B-lymphocyte surface antigen B1, Leu-16, Bp35, BM5, and LF5; the sequence is characterized by the SwissProt database entry P11836) is a hydrophobic transmembrane protein with a molecular weight of approximately 35 kD located on pre-B and mature B lymphocytes (Valentine, M. A. et al., J. Biol. Chem. 264 (1989) 11282-11287; Tedder, T. F., et al., Proc. Natl. Acad. Sci. U.S.A. 85 (1988) 208-212; Stamenkovic, I., et al., J. Exp. Med. 167 (1988) 1975-1980; Einfeld, D. A., et al., EMBO J. 7 (1988) 711-717; Tedder, T. F., et al., J. Immunol. 142 (1989) 2560-2568). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. Alternative splicing of this gene results in two transcript variants which encode the same protein. The terms "CD20" and "CD20 antigen" are used interchangeably herein, and include any variants, isoforms and species homologs of human CD20 which are naturally expressed by cells or are expressed on cells transfected with the CD20 gene. Binding of an antibody of the invention to the CD20 antigen mediate the killing of cells expressing CD20 by signaling through CD20, by inactivating CD20 or by cross-linking CD20. Preferably, the cell is a tumor cell. The killing of the cells expressing CD20 may occur by one or more of the following mechanisms: Direct cell death/apoptosis induction, ADCC, CDC and ADCP. Synonyms of CD20, as recognized in the art, include B-lymphocyte antigen CD20, B-lymphocyte surface antigen B1, Leu-16, Bp35, BM5, and LF5.

The term "CD20 expressing cancer" as used herein refers preferably to lymphomas (preferably B-Cell Non-Hodgkin's lymphomas (NHL)) and lymphocytic leukemias. Such lymphomas and lymphocytic leukemias include follicular lymphomas, Small Non-Cleaved Cell Lymphomas/Burkitt's lymphoma (including endemic Burkitt's lymphoma, sporadic Burkitt's lymphoma and Non-Burkitt's lymphoma), marginal zone lymphomas (including extranodal marginal zone B cell lymphoma (Mucosa-associated lymphatic tissue lymphomas, MALT), nodal marginal zone B cell lymphoma and splenic marginal zone lymphoma), Mantle cell lymphoma (MCL), Large Cell Lymphoma (including diffuse large B-cell lymphoma (DLBCL), Diffuse Mixed Cell Lymphoma, Immunoblastic Lymphoma, Primary Mediastinal B-Cell Lymphoma, Angiocentric Lymphoma-Pulmonary B-Cell Lymphoma), hairy cell leukemia, lymphocytic lymphoma, Waldenstrom's macroglobulinemia, acute lymphocytic leukemia (ALL), chronic lymphocytic leukemia (CLL)/small lymphocytic lymphoma (SLL), B-cell prolymphocytic leukemia, plasma cell neoplasms, plasma cell myeloma, multiple myeloma, plasmacytoma, Hodgkin's disease. More preferably, the term CD20 expressing cancer refers to Non-Hodgkin's lymphomas (NHL), follicular lymphomas, diffuse large B-cell lymphoma (DLBCL) and chronic lymphocytic leukemia (CLL).

The term "complement-dependent cytotoxicity (CDC)" refers to lysis of human tumor target cells by the antibody according to the invention in the presence of complement. CDC is measured preferably by the treatment of a preparation of CD20 expressing cells with an anti-CD20 antibody according to the invention in the presence of complement. CDC is found if the antibody induces at a concentration of 100 nM the lysis (cell death) of 20% or more of the tumor cells after 4 hours. The assay is performed preferably with $^{51}$Cr or Eu labeled tumor cells and measurement of released $^{51}$Cr or Eu. Controls include the incubation of the tumor target cells with complement but without the antibody.

Typically, type I and type II anti-CD20 antibodies of the IgG1 isotype show characteristic CDC properties. Type I anti-CD20 antibodies have and increased CDC (if IgG1 isotype) and type II anti-CD20 antibodies have a decreased CDC (if IgG1 isotype) compared to each other. Preferably both type I and type II anti-CD20 antibodies are IgG1 isotype antibodies.

As used herein, "cell signaling mechanism" or "cell signaling activity" is intended to refer to the entire signaling (i.e., signal transduction) pathway that leads to a particular cellular event or biological function, as well as any signaling steps along the pathway.

As used herein, the term "CH1 region" is intended to refer to the domain of the heavy chain of an immunoglobulin that is just C-terminal to the variable region and N-terminal to the hinge region. In an immunoglobulin of the IgG type, for example, CH1 is normally defined by Kabat positions 114 to 223 (Kabat numbering).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., Sequences of Proteins of Immunological Interest, 5th Ed. Public Health Service, National Institutes of Health, Bethesda, Md. (1991) and by Chothia et al., J Mol Biol. 196:901-917 (1987), each of which is hereby incorporated by reference in its entirety, where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

"Conservative" amino acid substitutions are those made by replacing one amino acid with another amino acid having similar structural and/or chemical properties, i.e., conservative amino acid replacements, and may be made on the basis of similarity in polarity, charge, solubility, hydrophobicity, hydrophilicity, and/or the amphipathic nature, and/or the bulk sizes of the residues involved. For example, nonpolar (hydrophobic) amino acids include glycine, alanine, leucine, isoleucine, valine, proline, phenylalanine, tryptophan, and methionine; polar neutral amino acids include serine, threonine, cysteine, tyrosine, asparagine, and glutamine; positively charged (basic) amino acids include arginine, lysine, and histidine; and negatively charged (acidic) amino acids include aspartic acid and glutamic acid. Furthermore, naturally occuring amino acid residues can be divided into classes differentiated by the bulk size of the amino acid residues. Small bulk size residues comprise alanine and glycine, medium bulk size residues comprise valine, isoleucine, leucine and proline and large bulk size residues comprise threonine, phenylalanine and tryptophan. The term "is substituted with an amino acid residue which is smaller or larger" is intended to refer to an amino acid substitution from the medium bulk size class to the small bulk size class (smaller) or to the large bulk size class (larger). Accordingly, the term "is substituted with an amino acid residue which is smaller" is intended to refer to an amino acid substitution from the medium bulk size class to the small bulk size class and to an amino acid substitution from the large bulk size class to the medium or small bulk size class. Accordingly, the term "is substituted with an amino acid residue which is larger" is intended to refer to an amino acid substitution from the medium bulk size class to the large bulk size class and to an amino acid substitution from the small bulk size class to the medium or large bulk size class.

"Substitutions", "insertions" or "deletions" are preferably in the range of about 1 to 20 amino acids, more preferably 1 to 10 amino acids, more preferably 1 to 4 amino acids, most preferably 1 amino acid. The variation allowed may be experimentally determined by systematically making insertions, deletions, or substitutions of amino acids in a polypeptide molecule using recombinant DNA techniques and assaying the resulting recombinant variants for activity.

"Cytokine release syndrome", which is an "infusion reaction", is a common immediate complication occurring with the use of antibody infusions such as e.g., the CD20-antibody rituximab. The pathogenesis is characterized in that the antibodies bind to T cell receptors, activating said T cells. The cytokines released by the activated T cells produce a type of systemic inflammatory response similar to that found in severe infection characterised by hypotension, pyrexia and rigors. Deaths due to cytokine release syndrome have been reported, and it can cause life-threatening pulmonary edema if the patient is fluid overloaded.

The term "cytotoxic agent" as used herein refers to a substance that inhibits or prevents a cellular function and/or causes cell death or destruction. Cytotoxic agents include, but are not limited to, radioactive isotopes (including but not limited to, $^{211}$Astatine, $^{131}$Iodine, $^{125}$Iodine, $^{90}$Yttrium, $^{186}$Rhenium, $^{188}$Rhenium, $^{153}$Samarium, $^{212}$Bismuth, $^{32}$Phosphorus, $^{212}$Lead and radioactive isotopes of Lutetium); chemotherapeutic agents or drugs (including but not limited to, methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof and the various antitumor or anticancer agents disclosed below.

An "effective amount" of an agent, e.g., a pharmaceutical formulation, refers to an amount effective, at dosages and for periods of time necessary, to achieve the desired therapeutic or prophylactic result.

As used herein, the term "effector function" or "Fc-mediated effector function" refers to those biological activities attributable to the Fc region (a native sequence Fc region or amino acid sequence variant Fc region) of an antibody, and vary with the antibody isotype. Examples of antibody effector functions include, but are not limited to: C1q binding and complement dependent cytotoxicity (CDC), Fc receptor binding affinity, antibody-dependent cell-mediated cytotoxicity (ADCC), antibody-dependent cellular phagocytosis (ADCP), cytokine secretion, immune-complex-mediated antigen uptake by antigen-presenting cells, down-regulation of cell surface receptors.

As used herein, the terms "engineer, engineered, engineering, glycoengineer, glycoengineered, glycoengineering", and "glycosylation engineering" are considered to include any manipulation of the glycosylation pattern of a naturally occurring or recombinant polypeptide, such as an antibody, or fragment thereof. Glycosylation engineering includes metabolic engineering of the glycosylation machinery of a cell, including genetic manipulations of the oligosaccharide synthesis pathways to achieve altered glycosylation of glycoproteins expressed in cells. In one embodiment, the glycosylation engineering is an alteration in glycosyltransferase activity. In a particular embodiment, the engineering results in altered glucosaminyltransferase activity and/or fucosyltransferase activity.

The term "expression of the CD20 antigen" is intended to indicate a significant level of expression of the CD20 antigen in a cell, preferably on the cell surface of a T- or B-cell, more preferably a B-cell, from a tumor or cancer, respectively, preferably a non-solid tumor. Patients having a "CD20 expressing cancer" can be determined by standard assays known in the art. "Expression of the CD20" antigen is also preferable intended to indicate a significant level of expression of the CD20 antigen in a cell, preferably on the cell surface of a T- or B-cell, more preferably a B-cell, in an autoimmune disease. CD20 antigen expression is measured e.g., using immunohistochemical (IHC) detection, FACS or via PCR-based detection of the corresponding mRNA.

As used herein, the term "Fc region" is intended to refer to a C-terminal region of an IgG heavy chain. Although the boundaries of the Fc region of an IgG heavy chain might vary slightly, the human IgG heavy chain Fc region is usually defined to stretch from the amino acid residue at position Cys226 to the carboxyl-terminus.

As used herein, the term "Fc-mediated cellular cytotoxicity" includes "antibody-dependent cell-mediated cytotoxicity" (ADCC) and cellular cytotoxicity mediated by a soluble Fc-fusion protein containing a human Fc-region. It is an immune mechanism leading to the lysis of "antibody-targeted cells" by "human immune effector cells", wherein the human immune effector cells are a population of leukocytes that display Fc receptors on their surface through which they bind to the Fc-region of antibodies or of Fc-fusion proteins and perform effector functions. Such a population may include, but is not limited to, peripheral blood mononuclear cells (PBMC) and/or natural killer (NK) cells. The antibody-targeted cells are cells bound by the antibodies or Fc-fusion proteins. The antibodies or Fc fusion-proteins bind to target cells via the protein part N-terminal to the Fc region.

As used herein, the terms "fusion" and "chimeric", when used in reference to polypeptides such as antibodies refer to polypeptides comprising amino acid sequences derived from two or more heterologous polypeptides, such as portions of antibodies from different species. For chimeric antibodies, for example, the non-antigen binding components may be derived from a wide variety of species, including primates such as chimpanzees and humans. The constant region of the chimeric antibody is most preferably substantially identical to the constant region of a natural human antibody; the variable region of the chimeric antibody is most preferably derived from a non-human (i.e., donor) antigen binding molecule that specifically binds an antigen of interest. The chimeric antibody may comprise the entire donor variable region; alternatively, the chimeric antibody may comprise a humanized or primatized antibody. Humanized antibodies are a particularly preferred form of fusion or chimeric antibody. Other forms of "chimeric antibodies" encompassed by the present invention are those in which the class or subclass has been modified or changed from that of the original antibody. Such "chimeric" antibodies are also referred to as "class-switched antibodies". Methods for producing chimeric antibodies involve conventional recombinant DNA and gene transfection techniques now well known in the art. See, e.g., Morrison, S. L., et al., Proc. Natl. Acad Sci. USA 81 (1984) 6851-6855; U.S. Pat. Nos. 5,202, 238 and 5,204,244.

As used herein, the term "Golgi localization domain" refers to the amino acid sequence of a Golgi resident polypeptide which is responsible for anchoring the polypeptide in location within the Golgi complex. Generally, localization domains comprise amino terminal "tails" of an enzyme.

As used herein, the term "heavy chain variable region" is intended to refer to the N-terminal domain of an immunoglobulin heavy chain. In one example, the heavy chain variable region is defined by Kabat positions 1 to 113 (with possible insertions at particular residues as designated by Kabat et al., Sequences of Proteins of Immunological Interest, 5th Ed. Public Health Service, National Institutes of Health, Bethesda, Md. (1991)). According to one embodiment of the present invention, a modified antibody can comprise a functional fragment of a heavy chain variable region.

As used herein, the term "heavy chain constant region" is intended to refer to the C terminal domain of an immunoglobulin heavy chain. There are five naturally-occurring classes of heavy chain constant regions: IgA, IgG, IgE, IgD, and IgM. In one example, the heavy chain constant region comprises a CH1 domain, a CH2 domain, and a CH3 domain.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). Disclosed also in van Dijk and van de Winkel, Curr. Opin. Pharmacol., 5: 368-74 (2001). Human antibodies can be prepared by administering the antigen to a transgenic animal that has been modified to produce such antibodies in response to antigenic challenge, but whose endogenous loci have been disabled, e.g., immunized xenomice (disclosed, e.g. in, U.S. Pat. Nos. 6,075,181 and 6,150,584 regarding XENOMOUSE™ technology). See also, for example, Li et al., Proc. Natl. Acad. Sci. USA, 103:3557-3562 (2006) regarding human antibodies generated via a human B-cell hybridoma technology.

As used herein, the term "humanized" is used to refer to an antigen binding molecule derived from a non-human antigen-binding molecule, for example, a murine antibody, that retains or substantially retains the antigen-binding properties of the parent molecule but which is less immunogenic in humans. This may be achieved by various methods including (a) grafting the entire non-human variable domains onto human constant regions to generate chimeric antibodies, (b) grafting only the non-human CDRs onto human framework and constant regions with or without retention of critical framework residues (e.g., those that are important for retaining good antigen binding affinity or antibody functions), or (c) transplanting the entire non-human variable domains, but "cloaking" them with a human-like section by replacement of surface residues. Such methods are disclosed in Jones et al., Morrison et al., Proc. Natl. Acad. Sd., 81:6851-6855 (1984); Morrison and Oi, Adv. Immunol, 44:65-92 (1988); Verhoeyen et al., Science, 239:1534-1536 (1988); Padlan, Molec. Immun., 28:489-498 (1991); Padlan, Molec. Immun., 31(3):169-217 (1994), each of which is hereby incorporated by reference in its entirety. There are generally three complementarity determining regions (CDRs) (CDR1, CDR2 and CDR3), in each of the heavy and light chain variable domains of an antibody, which are flanked by four framework subregions (i.e., FR1, FR2, FR3, and FR4) in each of the heavy and light chain variable domains of an antibody: FR1-CDR1-FR2-CDR2-FR3-CDR3-FR4. A discussion of humanized antibodies can be found, inter alia, in U.S. Pat. No. 6,632,927, and in published U.S. Application No. 2003/0175269, each of which is hereby incorporated by reference in its entirety. Similarly, as used herein, the term "primatized" is used to refer to an antigen-binding molecule derived from a non-primate antigen-binding molecule, for example, a murine antibody, that retains or substantially retains the antigen-binding properties of the parent molecule but which is less immunogenic in primates.

As used herein, a nucleic acid that "hybridizes under stringent conditions" to a nucleic acid sequence of the invention, refers to a polynucleotide that hybridizes in an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

As used herein, the term "host cell" covers any kind of cellular system which can be engineered to generate the polypeptides and antigen-binding molecules of the present invention. Host cells include cultured cells, including but not limited to, mammalian cultured cells, such as CHO cells, BHK cells, HEK293-EBNA cells, NSO cells, SP2/0 cells, Y0 myeloma cells, P3X63 mouse myeloma cells, PER cells, PER. C6 cells or hybridoma cells, yeast cells, insect cells, and plant cells, to name only a few, but also cells comprised within a transgenic animal, transgenic plant or cultured plant or animal tissue. In one embodiment, the host cell is engineered to allow the production of an antigen binding molecule with modified glycoforms. In a preferred embodiment, the antigen binding molecule is an antibody, antibody fragment, or fusion protein. In certain embodiments, the host cells have been further manipulated to express increased levels of one or more polypeptides having GnTIII activity. In other embodiments, the host cells have been engineered to have eliminated, reduced or inhibited core α1,6-fucosyltransferase activity. The term core α1,6-fucosyltransferase activity encompasses both expression of the core α1,6-fucosyltransferase gene as well as interaction of the core α1,6-fucosyltransferase enzyme with its substrate.

An "immunoconjugate" is an antibody conjugated to one or more heterologous molecule(s), including but not limited to a cytotoxic agent.

As used herein, the term "altered Fc-mediated cellular cytotoxicity" or "altered antibody-dependent cell-mediated cytotoxicity" (ADCC) is defined as either an increase or decrease in the number of "antibody-targeted cells" that are lysed in a given time, at a given concentration of antibody, or of Fc-fusion protein, in the medium surrounding the target cells, by the mechanism of ADCC defined herein, and/or a reduction or increase in the concentration of antibody, or of Fc-fusion protein, in the medium surrounding the target cells, required to achieve the lysis of a given number of "antibody-targeted cells", in a given time, by the mechanism of ADCC. The increase or decrease in ADCC is relative to the cellular cytotoxicity mediated by the same antibody, or Fc-fusion protein, produced by the same type of host cells, using the same standard production, purification, formulation and storage methods, which are known to those skilled in the art, but that has not been produced by host cells engineered to express the glycosyltransferase GnTIII by the methods disclosed herein or that has not been subjected to amino acid substitution as disclosed herein.

An "individual" or "subject" is a mammal. Mammals include, but are not limited to, domesticated animals (e.g., cows, sheep, cats, dogs, and horses), primates (humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). A review of methods for assessment of antibody purity is disclosed, inter alia, in Flatman et al., J. Chromatogr. B 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-CD20 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being disclosed herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150'000 daltons, composed of two identical "light chains" and two identical "heavy chains" that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (2), based on the amino acid sequence of its constant domain.

The term "nucleic acid molecule", as used herein, is intended to include DNA molecules and RNA molecules. A nucleic acid molecule may be single-stranded or double-stranded, but preferably is double-stranded DNA.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the term "parent antibody", or "parent non-modified antibody", or "parent non-substituted antibody" refers to an antibody having a particular amino acid sequence encoded by a polynucleotide sequence. The sequence of the parent molecule (i.e., the "parent sequence") serves as a reference sequence for making amino acid residue substitutions that alter the ability of the resulting molecule (e.g., a modified antigen binding molecule) to induce or block cell signaling activity and/or cross-linking of antigen. Likewise, the activity of a parent molecule (e.g., the "parent non-substituted antibody) serves as the reference when determining whether a substitution has an effect on cell signaling activity and/or cross-linking of antigen, and, where relevant, the extent of that effect. A sequence containing one or more amino acid substitutions in comparison to its parent (e.g., a variant heavy chain region) may in turn serve as a parent sequence for further substitutions.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The terms "polypeptide" and "protein" are used interchangeably to refer to a polymer of amino acid residues, comprising natural or non-natural amino acid residues, and are not limited to a minimum length. Thus, peptides, oligopeptides, dimers, multimers, and the like are included within the definition. Both full-length proteins and fragments thereof are encompassed by the definition. The terms also include post-translational modifications of the polypeptide, including, for example, glycosylation, sialylation, acetylation, and phosphorylation.

Furthermore, a "polypeptide" herein also refers to a modified protein such as single or multiple amino acid residue deletions, additions, and substitutions to the native sequence, as long as the protein maintains a desired activity.

For example, a serine residue may be substituted to eliminate a single reactive cysteine or to remove disulfide bonding or a conservative amino acid substitution may be made to eliminate a cleavage site. These modifications may be deliberate, as through site-directed mutagenesis, or may be accidental, such as through mutations of hosts which produce the proteins or errors due to polymerase chain reaction (PCR) amplification.

As used herein, a "polypeptide having GnTIII activity" refers to polypeptides that are able to catalyze the addition of a N-acetylglucosamine (GlcNAc) residue in β-1-4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependence in a given activity as compared to the GnTIII (i.e., the candidate polypeptide will exhibit greater activity or not more than about 25-fold less and, preferably, not more than about tenfold less activity, and most preferably, not more than about threefold less activity relative to the GnTIII).

The "ratio of the binding capacities to CD20 on Raji cells (ATCC-No. CCL-86) of an anti-CD20 antibodies compared to rituximab" is determined by direct immunofluorescence measurement (the mean fluorescent intensities (MFI) is measured) using said anti-CD20 antibody conjugated with Cy5 and rituximab conjugated with Cy5 in a FACSArray (Becton Dickinson) with Raji cells (ATCC-No. CCL-86), and calculated as follows:

Ratio of the binding capacities to CD20 on Raji cells (ATCC-No. CCL-86)=

$$\frac{MFI(Cy5\text{-anti-}CD20 \text{ antibody})}{MFI(Cy5\text{-rituximab})} \times \frac{Cy5\text{-labeling ratio}(Cy5\text{-rituximab})}{Cy5\text{-labeling ratio}(Cy5\text{-anti-}CD20 \text{ antibody})}$$

MFI is the mean fluorescent intensity. The "Cy5-labeling ratio" as used herein means number of Cy5-label molecules per molecule antibody.

The term "recombinant human antibody", as used herein, is intended to include all human antibodies that are prepared, expressed, created or isolated by recombinant means, such as antibodies isolated from a host cell such as a NSO or CHO cell or from an animal (e.g. a mouse) that is transgenic for human immunoglobulin genes or antibodies expressed using a recombinant expression vector transfected into a host cell. Such recombinant human antibodies have variable and constant regions derived from human germline immunoglobulin sequences in a rearranged form. The recombinant human antibodies according to the invention have been subjected to in vivo somatic hypermutation. Thus, the amino acid sequences of the recombinant antibodies are sequences that, while derived from and related to human germline sequences, may not naturally exist within the human antibody germline repertoire in vivo.

As used herein, the term "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as ADCC). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)). In one embodiment, a region equivalent to the Fc region can also form part of a heterologous fusion protein. In some embodiments, a region equivalent to the Fc region also encompasses a corresponding region from another class of immunoglobulin heavy chain (including but not limited to, IgA, IgE, IgD, and IgM).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The "variable region" or "variable domain" of an antibody refers to the amino-terminal domains of the heavy or light chain of the antibody. The variable domain of the heavy chain may be referred to as "VH". The variable domain of the light chain may be referred to as "VL". These domains are generally the most variable parts of an antibody and contain the antigen-binding sites.

By "variant protein", "protein variant" or "variant" as used herein is meant a protein that differs from that of a parent protein by virtue of at least one amino acid modification. Variant may refer to the protein itself, a composition comprising the polypeptide, or the amino sequence that encodes it. Preferably, the protein variant has at least one amino acid modification compared to the parent protein, e.g. from about one to about seventy amino acid modifications, and preferably from about one to about five amino acid modifications compared to the parent. The protein variant sequence as disclosed herein will preferably possess at least about 80% homology with a parent protein sequence, and most preferably at least about 90% homology, more preferably at least about 95% homology. Variant protein can refer to the variant protein itself, compositions comprising the protein variant, or the DNA sequence that encodes it. Accordingly, by "antibody variant", "variant antibody" or "variant heavy chain region" as used herein is meant an antibody, or part of an antibody, that differs from a parent antibody by virtue of at least one amino acid modification including but not limited to amino acid substitution, deletion or insertion. "IgG variant" or "variant IgG" as used herein is meant an antibody that differs from a parent IgG by virtue of at least one amino acid modification, and "immunoglobulin variant" or "variant immunoglobulin" as used herein is meant an immunoglobulin sequence that differs from that of a parent immunoglobulin sequence by virtue of at least one amino acid modification.

In the context of the present invention, the term "variant" is used interchangeably with the term "mutated". Accordingly, by "antibody mutant", "mutated antibody" or "mutaded heavy chain region" as used herein is meant an antibody, or part of an antibody, that differs from a parent antibody by virtue of at least one amino acid modification including but not limited to amino acid substitution, deletion or insertion. "IgG mutant" or "mutated IgG" as used herein is meant an antibody that differs from a parent IgG by virtue of at least one amino acid modification, and "immunoglobulin mutant" or "mutant immunoglobulin" as used herein is meant an immunoglobulin sequence that differs from that of a parent immunoglobulin sequence by virtue of at least one amino acid modification.

The term "variable" in relation with the term "variable domain" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody-dependent cell-mediated cytotoxicity (ADCC).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors". Recombinant variants encoding same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

The term "wildtype polypeptide" and "wildtype (human) Fc region" as used herein refers to a polypeptide and Fc region, respectively, comprising an amino acid sequence which lacks one or more of the Fc region modifications disclosed herein, because they have not been introduced, and serve for example as controls. The wildtype polypeptide may comprise a native sequence Fc region or an Fc region with pre-existing amino acid sequence modifications (such as additions, deletions and/or substitutions).

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polypeptide is at least 80%, 85%, 90%, 95%, 96%, 97%, 98% or 99% identical to a nucleotide sequence or polypeptide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al, Comp. App. Biosci. 6:237-245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the FASTDB program as disclosed herein using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at the 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' end of the subject sequence which are not matched/aligned with the query. In this case the percent identity calculated by FASTDB is not manually corrected. Once again, only bases on the 5' and 3' end of the subject sequence which are not matched/aligned with the query sequence are manually corrected for. No other manual corrections are to be made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to a reference polypeptide can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al, Comp. App. Biosci. 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the FASTDB program as disclosed herein using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to be made for the purposes of the present invention.

II. Embodiments According to the Invention

Modified Antibodies According to the Invention

There remains a need for monoclonal antibodies with improved therapeutic potential for human therapy. Targeting signaling pathways with monoclonal antibodies is very challenging, but modulating antigens associated with cell signaling, including, but not limited to, the induction of direct cell death, is much needed for improved cancer therapy. Unexpectedly, the present inventors found that mutations in the elbow hinge region at the amino acid positions as disclosed herein lead to altered (increased or decreased) induction of direct cell death. Surprisingly, these mutations can be combined with mutations in the Fc part of the antibodies according to the present invention, leading to reduced or ablated effector function. In combination, the modifications according to the present invention allow a selective and independent modulation of induction of direct cell death and/or effector function as compared to non-substituted parent antibodies.

The present inventors found in the case of anti-CD20 antibodies that mutations of valine or leucine residues at Kabat position 11 and of proline at position 151 do contribute to altered cell signaling activity including, but not limited to, altered induction of direct cell death. Alone or in combination these modifications to the elbow hinge region affect the elbow angle which is defined as the angle between the two axis of pseudorotational symmetry between the VL/VH and the CL/CH1 pairs. Increasing or decreasing the elbow angle change the orientation by which the antibodies of the present invention bind the respective antigen target without changing the overall affinity compared to the parent antibodies. Accordingly, in one embodiment, an antibody is provided, comprising a variant heavy chain region comprising at least one amino acid substitution relative to the parent non-substituted heavy chain region, wherein the heavy chain region of the parent non-substituted antibody comprises at least one of the amino acid residues selected from the group consisting of Val11, Leu11 and Pro151, and wherein said substitution is at one of said amino acid residues selected from the group consisting of Val11, Leu11 and Pro151, wherein direct cell death induced by the antibody comprising the variant heavy chain region is altered compared to direct cell death induced by the antibody comprising the parent non-substituted heavy chain region. In a preferred embodiment at least one of the amino acid residues selected from the group consisting of Val11, Leu11 and Pro151 is substituted with at least one of the amino acid residues selected from the group consisting of alanine, glycine, phenylalanine, threonine and tryptophan.

In a further aspect, the present invention is directed to antibodies comprising a modified heavy chain CH1 region and/or a modified VH region as disclosed herein, whereby the ability of these antibodies to induce cell signaling activity of a target antigen and/or mediate cross-linking of target antigen is enhanced (i.e., induced or increased) or reduced (i.e., inhibited or decreased). The cell signaling activity can be agonist activity or antagonist activity. According to one aspect of the invention, agonist activity is induced by a modified antibody when it binds to a cell membrane-associated receptor and initiates cell signaling activity. In a specific embodiment, the cell signaling activity is an apoptosis pathway. In another embodiment, the cell signaling activity is a cell differentiation pathway. According to another aspect of the invention, antagonist activity by a modified antibody occurs, when the antibody binds to a cell membrane-associated receptor and prevents the induction of cell signaling activity or disrupts an ongoing signal. Antagonist activity may be achieved, for example, by blocking the binding and subsequent signal transduction of an endogenous ligand and/or by preventing the cross-linking or oligomerization of receptors or other molecules that would be necessary for induction of cell signaling activity. In one embodiment, the cell signaling activity that is inhibited or disrupted is a cell growth pathway. In another embodiment, the cell signaling activity that is inhibited or disrupted is a cell division pathway. In another embodiment, the cell signaling activity that is inhibited or disrupted is a cell survival pathway.

Likewise, the amino acid sequence of the parent polypeptide may be modified to generate an antibody with altered ability to mediate cross-linking of one or more target antigens when the modified antibody is complexed with (e.g., bound to) the target antigen(s). In one embodiment, the bound target antigens (e.g., cell surface receptor molecules) are brought into closer proximity to each other and/or a more favorable conformation for interaction than they would be by the corresponding non-substituted parent antibody, thereby increasing cross-linking and oligomerization between the bound antigens. In another embodiment, the bound target antigens (e.g., cell surface receptor molecules) are kept farther apart from each other, and/or in a less favorable conformation for interaction than they would be by the corresponding non-substituted parent antibody, thereby reducing or preventing cross-linking and oligomerization between the bound antigens. In a particular embodiment, the increased cross-linking or oligomerization results in increased direct cell death, increased cell differentiation, decreased cell growth, decreased cell division, or decreased cell survival. In another embodiment, decreased cross-linking or oligomerization results in decreased direct cell death, decreased cell differentiation, increased cell growth, increased cell division, or increased cell survival.

In a preferred aspect of the present invention, said altered ability to induce cell signaling activity and/or cross-linking of target antigen leads to altered induction of direct cell death. In a further embodiment induction of direct cell death is altered compared to direct cell death induced by the parent non-substituted antibody. In a preferred embodiment induction of direct cell death is increased compared to direct cell death induced by the parent non-substituted antibody. In another preferred embodiment induction of direct cell death is decreased compared to direct cell death induced by the parent non-substituted antibody.

The modified heavy chain regions of the antibodies of the present invention differ from the corresponding non-modified parent antibody by at least one amino acid substitution. The "parent", "non-substituted", "starting", or "non-modified" polypeptide preferably comprises at least a portion of an antibody heavy chain, and may be prepared using techniques available in the art for generating polypeptides comprising a heavy chain CH1 and VH region or portion thereof. Preferably, the parent non-substituted polypeptide is an antibody.

In one aspect of the present invention the parent non-substituted antibody is any of any class (for example, but not limited to IgG, IgM, and IgE). In certain embodiments, antibodies of the invention are members of the IgG class of antibodies. In a specific embodiment, antibodies of the invention are of the IgG1, IgG2 or IgG4 subclass.

In one embodiment, the parent non-substituted antibody comprises at least one of the amino acid residues selected from the group consisting of Val11, Leu11 and Pro151. In another embodiment, at least one of the amino acid residues selected from the group consisting of Val11, Leu11 and Pro151 is substituted. In another embodiment, at least one of the amino acid residues selected from the group consisting of Val11, Leu11 and Pro151 is substituted with an amino acid residue which is smaller or larger compared to the amino acid residue at the corresponding position in the non-substituted parent heavy chain region. In another embodiment, at least one of the amino acid residues selected from the group consisting of Val11, Leu11 and Pro151 is substituted with an amino acid residue which is smaller or larger compared to the amino acid residue at the corresponding position in the non-substituted parent heavy chain region, wherein the elbow hinge angle defined by the intersection of the two axis of pseudorotational symmetry between the VL/VH and the CL/CH1 pair is altered compared to the elbow hinge angle of the parent non-substituted antibody.

In another embodiment, at least one of the amino acid residues selected from the group consisting of Val11, Leu11 and Pro151 is substituted with an amino acid residue which is smaller compared to the amino acid residue at the corresponding position in the non-substituted parent heavy chain region, wherein the elbow hinge angle defined by the intersection of the two axis of pseudorotational symmetry between the VL/VH and the CL/CH1 pair is reduced compared to the elbow hinge angle of the parent non-substituted antibody, wherein direct cell death induced by the antibody comprising the variant heavy chain region is decreased compared to direct cell death induced by the antibody comprising the parent non-substituted heavy chain region. In another embodiment, the elbow hinge angle defined by the intersection of the two axis of pseudorotational symmetry between the VL/VH and the CL/CH1 pair is reduced to less than 150° compared to the elbow hinge angle of the parent non-substituted antibody. In preferred embodiments the elbow hinge angle is reduced to less than 145°, preferably less than 140°, preferably less than 135°.

In another embodiment, at least one of the amino acid residues selected from the group consisting of Val11, Leu11 and Pro151 is substituted with an amino acid residue selected from the group consisting of alanine and glycine, wherein the elbow hinge angle defined by the intersection of the two axis of pseudorotational symmetry between the VL/VH and the CL/CH1 pair is decreased compared to the elbow hinge angle of the parent non-substituted antibody, wherein direct cell death induced by the antibody comprising the variant heavy chain region is decreased compared to direct cell death induced by the antibody comprising the parent non-substituted heavy chain region. In a preferred embodiment at least one of the amino acid residues selected from the group consisting of Val11, Leu11 and Pro151 is substituted with alanine.

In another embodiment, at least one of the amino acid residues selected from the group consisting of Val11, Leu11 and Pro151 is substituted with an amino acid residue which is larger compared to the amino acid residue at the corresponding position in the non-substituted parent heavy chain region, wherein the elbow hinge angle defined by the intersection of the two axis of pseudorotational symmetry between the VL/VH and the CL/CH1 pair is increased compared to the elbow hinge angle of the parent non-substituted antibody, wherein direct cell death induced by the antibody comprising the variant heavy chain region is increased compared to direct cell death induced by the antibody comprising the parent non-substituted heavy chain region. In another embodiment, the elbow hinge angle defined by the intersection of the two axis of pseudorotational symmetry between the VL/VH and the CL/CH1 pair is increased to more than 150° compared to the elbow hinge angle of the parent non-substituted antibody. In preferred embodiments the elbow hinge angle is increased to more than 155°, preferably more than 160°, preferably more than 165°.

In another embodiment, at least one of the amino acid residues selected from the group consisting of Val11, Leu11 and Pro151 is substituted with an amino acid residue selected from the group consisting of phenylalanine, threonine and tryptophan, wherein the elbow hinge angle defined by the intersection of the two axis of pseudorotational symmetry between the VL/VH and the CL/CH1 pair is increased compared to the elbow hinge angle of the parent non-substituted antibody, wherein direct cell death induced by the antibody comprising the variant heavy chain region is increased compared to direct cell death induced by the antibody comprising the parent non-substituted heavy chain region. In a preferred embodiment at least one of the amino acid residues selected from the group consisting of Val11, Leu11 and Pro151 is substituted with phenylalanine.

In one embodiment, an antibody is provided, comprising a variant heavy chain region comprising an amino acid substitution relative to the parent non-substituted heavy chain region, wherein the heavy chain region of the parent non-substituted antibody comprises the amino acid residue Pro151, wherein the residues are numbered according to the EU index as in Kabat, and wherein said substitution is at said amino acid residue Pro151, wherein direct cell death induced by the antibody comprising the variant heavy chain region is altered compared to direct cell death induced by the antibody comprising the parent non-substituted heavy chain region. In another embodiment, Pro151 is substituted with an amino acid which is either smaller or larger than proline, wherein the elbow hinge angle defined by the intersection of the two axis of pseudorotational symmetry between the VL/VH and the CL/CH1 pair is altered compared to the elbow hinge angle of the parent non-substituted antibody.

Parent non-substituted antibodies according to the invention include, but are not limited to, monoclonal antibodies. They may either be so-called chimaeric antibodies, humanized antibodies or fully human antibodies. They may either be full length antibodies or antibody fragments having the same biological activity including amino acid sequence variants and/or glycosylation variants of such antibodies or fragments. Parent non-substituted antibodies according to the invention include, but are not limited to, 3F8 (anti-GD2), Abagovomab (anti CA-125), Abciximab (anti CD41 (integrin alpha-IIb)), Adalimumab (anti-TNF-α), Adecatumumab (anti-EpCAM, CD326), Afelimomab (anti-TNF-α); Afutuzumab (anti-CD20), Alacizumab pegol (anti-VEGFR2), ALD518 (anti-IL-6), Alemtuzumab (Campath, MabCampath, anti-CD52), Altumomab (anti-CEA), Anatumomab (anti-TAG-72), Anrukinzumab (IMA-638, anti-IL-13), Apolizumab (anti-HLA-DR), Arcitumomab (anti-CEA), Aselizumab (anti-L-selectin, CD62L), Atlizumab (tocilizumab, Actemra, RoActemra, anti-IL-6 receptor), Atorolimumab (anti-Rhesus factor), Bapineuzumab (anti-beta amyloid), Basiliximab (Simulect, antiCD25 (a chain of IL-2 receptor)), Bavituximab (anti-phosphatidylserine), Bectumomab (LymphoScan, anti-CD22), Belimumab (Benlysta, LymphoStat-B, anti-BAFF), Benralizumab (anti-CD125), Bertilimumab (anti-CCL11 (eotaxin-1)), Besilesomab (Scintimun, anti-CEA-related antigen), Bevacizumab (Avastin, anti-VEGF-A), Biciromab (FibriScint, anti-fibrin II beta chain), Bivatuzumab (anti-CD44 v6), Blinatumomab (BiTE, anti-CD19), Brentuximab (cAC10, anti-CD30 TNFRSF8), Briakinumab (anti-IL-12, IL23), Canakinumab (Ilaris, anti-IL-1), Cantuzumab (C242, anti-CanAg), Capromab, Catumaxomab (Removab, anti-EpCAM, anti-CD3), CC49 (anti-TAG-72), Cedeliziumab (anti-CD4), Certolizumab pegol (Cimzia anti-TNF-α), Cetuximab (Erbitux, IMC-C225, anti-EGFR), Citatuzumab bogatox (anti-EpCAM), Cixutumumab (anti-IGF-1), Clenoliximab (anti-CD4), Clivatuzumab (anti-MUC 1), Conatumumab (anti-TRAIL-R2), CR6261 (anti-Influenza A hemagglutinin), Dacetuzumab (anti-CD40), Daclizumab (Zenapax, anti-CD25 (a chain of IL-2 receptor)), Daratumumab (anti-CD38, cyclic ADP ribose hydrolase), Denosumab (Prolia, anti-RANKL), Detumomab (anti-B-lymphoma cell), Dorlimomab, Dorlixizumab, Ecromeximab (anti-GD3 ganglioside), Eculizumab (Soliris, anti-C5), Edobacomab (anti-endotoxin), Edrecolomab (Panorex, MAb17-1A, anti-EpCAM), Efalizumab (Raptiva, anti-LFA-1 (CD 11a)), Efungumab (Mycograb, anti-Hsp90), Elotuzumab (anti-SLAMF7), Elsilimomab (anti-IL-6), Enlimomab pegol (anti-ICAM-1 (CD54)), Epitumomab (anti-episialin), Epratuzumab (anti-CD22), Erlizumab (anti-ITGB2 (CD 18)), Ertumaxomab (Rexomun, anti-HER2/neu, CD3), Etaracizumab (Abegrin, anti-integrin $α_vβ_3$), Exbivirumab (anti-hepatitis B surface antigen), Fanolesomab (NeutroSpec, anti-CD 15), Faralimomab (anti-interferon receptor), Farletuzumab (anti-folate receptor 1), Felvizumab (anti-respiratory syncytial virus), Fezakinumab (anti-IL-22), Figitumumab (anti-IGF-1 receptor), Fontolizumab (anti-IFN-γ), Foravirumab (anti-rabies virus glycoprotein), Fresolimumab (anti-TGF-β), Galiximab (anti-CD80), Gantenerumab (anti-beta amyloid), Gavilimomab (anti-CD147 (basigin)), Gemtuzumab (anti-CD33), Girentuximab (anti-carbonic anhydrase 9), Glembatumumab (CR011, anti-GPNMB), Golimumab (Simponi, anti-TNF-α), Gomiliximab (anti-CD23 (IgE receptor)), Ibalizumab (anti-CD4), Ibritumomab (anti-CD20), Igovomab (Indimacis-125, anti-CA-125), Imciromab (Myoscint, anti-cardiac myosin), Infliximab (Remicade, anti-TNF-a), Intetumumab (anti-CD51), Inolimomab (anti-CD25 (a chain of IL-2 receptor)), Inotuzumab (anti-CD22), Ipilimumab (anti-CD 152), Iratumumab (anti-CD30 (TNFRSF8)), Keliximab (anti-CD4), Labetuzumab (CEA-Cide, anti-CEA), Lebrikizumab (anti-IL-13). Lemalesomab (anti-NCA-90 (granulocyte antigen)), Lerdelimumab (anti-TGF beta 2), Lexatumumab (anti-TRAIL-R2), Libivirumab (anti-hepatitis B surface antigen), Lintuzumab (anti-CD33)), Lucatumumab (anti-CD40), Lumiliximab (anti-CD23 (IgE receptor), Mapatumumab (anti-TRAIL-R1), Maslimomab (anti-T-cell receptor), Matuzumab (anti-EGFR), Mepolizumab (Bosatria, anti-IL-5), Metelimumab (anti-TGF beta 1), Milatuzumab (anti-CD74), Minretumomab (anti-TAG-72), Mitumomab (BEC-2, anti-GD3 ganglioside), Morolimumab (anti-Rhesus factor), Motavizumab (Numax, anti-respiratory syncytial virus), Muromonab-CD3 (Orthoclone OKT3, anti-CD3), Nacolomab (anti-C242), Naptumomab (anti-5T4), Natalizumab (Tysabri, anti-integrin $\alpha_4$), Nebacumab (anti-endotoxin), Necitumumab (anti-EGFR), Nerelimomab (anti-TNF-a), Nimotuzumab (Theracim, Theraloc, anti-EGFR), Nofetumomab, Obinutuzumab (anti-CD20), Ocrelizumab (anti-CD20), Odulimomab (Afolimomab, anti-LFA-1 (CD11a)), Ofatumumab (Arzerra, anti-CD20), Olaratumab (anti-PDGF-R$\alpha$), Omalizumab (Xolair, anti-IgE Fc region), Oportuzumab (anti-EpCAM), Oregovomab (OvaRex, anti-CA-125), Otelixizumab (anti-CD3), Pagibaximab (anti-lipoteichoic acid), Palivizumab (Synagis, Abbosynagis, anti-respiratory syncytial virus), Panitumumab (Vectibix, ABX-EGF, anti-EGFR), Panobacumab (anti-*Pseudomonas aeruginosa*), Pascolizumab (anti-IL-4), Pemtumomab (Theragyn, anti-MUC1), Pertuzumab (Omnitarg, 2C4, anti-IIER2/neu), Pexelizumab (anti-C5), Pintumomab (anti-adenocarcinoma antigen), Priliximab (anti-CD4), Pritumumab (anti-vimentin), PRO 140 (anti-CCR5), Racotumomab (1E10, anti-(N-glycolylneuraminic acid (NeuGc, NGNA)-gangliosides GM3)), Rafivirumab (anti-rabies virus glycoprotein), Ramucirumab (anti-VEGFR2), Ranibizumab (Lucentis, anti-VEGF-A), Raxibacumab (anti-anthrax toxin, protective antigen), Regavirumab (anti-cytomegalovirus glycoprotein B), Reslizumab (anti-IL-5), Rilotumumab (anti-HGF), Rituximab (MabThera, Rituxanmab, anti-CD20), Robatumumab (anti-IGF-1 receptor), Rontalizumab (anti-IFN-a), Rovelizumab (LeukArrest, anti-CD11, CD 18), Ruplizumab (Antova, anti-CD 154 (CD40L)), Satumomab (anti-TAG-72), Sevirumab (anti-cytomegalovirus), Sibrotuzumab (anti-FAP), Sifalimumab (anti-IFN-a), Siltuximab (anti-IL-6), Siplizumab (anti-CD2), (Smart) MI95 (anti-CD33), Solanezumab (anti-beta amyloid), Sonepcizumab (anti-spingosine-1-phosphate), Sontuzumab (anti-episialin), Stamulumab (anti-myostatin), Sulesomab (LeukoScan, (anti-NCA-90 (granulocyte antigen), Tacatuzumab (anti-alpha-fetoprotein), Tadocizumab (anti-integrin $\alpha_{IIb}\beta_3$), Talizumab (anti-IgE), Tanezumab (anti-NGF), Taplitumomab (anti-CD19), Tefibazumab (Aurexis, (anti-clumping factor A)), Telimomab, Tenatumomab (anti-tenascin C), Teneliximab (anti-CD40), Teplizumab (anti-CD3), TGN1412 (anti-CD28), Ticilimumab (Tremelimumab, (anti-CTLA-4)), Tigatuzumab (anti-TRAIL-R2), TNX-650 (anti-IL-13), Tocilizumab (Atlizumab, Actemra, RoActemra, (anti-IL-6 receptor)), Toralizumab (anti-CD 154 (CD40L)), Tositumomab (anti-CD20), Trastuzumab (Herceptin, (anti-HER2/neu)), Tremelimumab (anti-CTLA-4), Tucotuzumab celmoleukin (anti-EpCAM), Tuvirumab (anti-hepatitis B virus), Urtoxazumab (anti-*Escherichia coli*), Ustekinumab (Stelara, anti-IL-12, IL-23), Vapaliximab (anti-AOC3 (VAP-1)), Vedolizumab (anti-integrin $\alpha_4\beta_7$), Veltuzumab (anti-CD20), Vepalimomab (anti-AOC3 (VAP-1), Visilizumab (Nuvion, anti-CD3), Vitaxin (anti-vascular integrin avb3), Volociximab (anti-integrin $\alpha_5\beta_1$), Votumumab (HumaSPECT, anti-tumor antigen CTAA16.88), Zalutumumab (HuMax-EGFr, (anti-EGFR)), Zanolimumab (HuMax-CD4, anti-CD4), Ziralimumab (anti-CD 147 (basigin)), Zolimomab (anti-CD5), Etanercept (Enbrel®), Alefacept (Amevive®), Abatacept (Orencia®), Rilonacept (Arcalyst), 14F7 (anti-IRP-2 (Iron Regulatory Protein 2)), 14G2a (anti-GD2 ganglioside, from Nat. Cancer Inst, for melanoma and solid tumors), J591 (anti-PSMA, Weill Cornell Medical School for prostate cancers), 225.28S (anti-HMW-MAA (High molecular weight-melanoma-antigen), Sorin Radiofarrnaci S.R.L. (Milan, Italy) for melanoma), COL-1 (anti-CEACAM3, CGM1, from Nat. Cancer Inst. USA for colorectal and gastric cancers), CYT-356 (Oncoltad®, for prostate cancers), HNK20 (OraVax Inc. for respiratory syncytial virus), ImmuRAIT (from Immunomedics for NHL), Lym-1 (anti-HLA-DR10, Peregrine Pharm. for Cancers), MAK-195F (anti-TNF (tumor necrosis factor; TNFA, TNF-alpha; TNFSF2), from Abbott/Knoll for Sepsis toxic shock), MEDI-500 (T10B9, anti-CD3, TR$\alpha\beta$ (T cell receptor alpha/beta), complex, from MedImmune Inc for Graft-versus-host disease), RING SCAN (anti-TAG 72 (tumour associated glycoprotein 72), from Neoprobe Corp. for Breast, Colon and Rectal cancers), Avicidin (anti-EPCAM (epithelial cell adhesion molecule), anti-TACSTD1 (Tumor-associated calcium signal transducer 1), anti-GA733-2 (gastrointestinal tumor-associated protein 2), anti-EGP-2 (epithelial glycoprotein 2); anti-KSA (KS ¼ antigen; M4S; tumor antigen 17-1A; CD326, from NeoRx Corp. for Colon, Ovarian, Prostate cancers and NHL); LymphoCide (Immunomedics, NJ), Smart ID10 (Protein Design Labs), Oncolym (Techniclone Inc, CA), Allomune (BioTransplant, CA), anti-VEGF (Genentech, CA); CEAcide (Immunomedics, NJ), IMC-1C11 (ImClone, NJ) and Cetuximab (ImClone, NJ).

In a preferred embodiment, the parent non-substituted antibody is an anti-CD20 antibody. Such antibodies are preferably monoclonal antibodies. They may either be chimaeric antibodies, humanized antibodies or fully human antibodies. They may either be full length anti-CD20 antibodies or anti-CD20 antibody fragments having the same biological activity including amino acid sequence variants and/or glycosylation variants of such antibodies or fragments. Humanized anti-CD20 parent non-substituted antibodies according to the invention are specified with the INN names rituximab (see e.g., U.S. Pat. No. 7,381,560 and EP2000149B1 of Anderson et. al., see e.g., FIGS. 4 and 5), ocrelizumab (as disclosed in WO 2004/056312 and WO 2006/084264), ibritumomab (see WO 94/011026), tositumomab (WHO Drug Information, Vol. 12, No. 4, 1998, p. 281), veltuzumab (WHO Drug Information, Vol. 22, No. 3, 2008, p. 28) and obinutuzumab (recommended INN, WHO Drug Information, Vol. 26, No. 4, 2012, p. 453).

A preferred parent non-substituted CD20 antibody is rituximab (a type I anti-CD20 antibody) which is sold by Genentech Inc. and F. Hoffmann-La Roche Ltd under the trade name MABTHERA™ or RITUXAN™. Rituximab is a genetically engineered chimeric human gamma 1 murine constant domain containing monoclonal antibody directed against the human CD20 antigen. This chimeric antibody contains human gamma 1 constant domains and is identified by the name "C2B8" in U.S. Pat. No. 5,736,137 (Anderson et. al.) issued on Apr. 17, 1998, assigned to IDEC Pharmaceuticals Corporation. Rituximab is approved for the treatment of patients with relapsed or refracting low-grade or follicular, CD20 positive, B cell non-Hodgkin's lymphoma. In vitro mechanism of action studies have shown that rituximab exhibits human complement-dependent cytotoxicity (CDC) (Reff, M. E., et. al., Blood 83 (1994) 435-445). Additionally, it exhibits significant activity in assays that measure antibody-dependent cell-mediated cytotoxicity (ADCC). Rituximab is not afucosylated.

Yet another parent non-substituted antibody according to the invention is a humanized B-Ly1 antibody. The term "humanized B-Ly1 antibody" refers to humanized B-Ly1 antibodies as disclosed in WO 2005/044859 and WO 2007/031875, which were obtained from the murine monoclonal anti-CD20 antibody B-Ly1 (variable region of the murine heavy chain (VH): SEQ ID NO: 3; variable region of the murine light chain (VL): SEQ ID NO: 4 (see Poppema, S. and Visser, L., Biotest Bulletin 3 (1987) 131-139)) by chimerization with a human constant domain from IgG1 and following humanization (see WO 2005/044859 and WO 2007/031875). These humanized B Ly1 antibodies are disclosed in detail in WO 2005/044859 and WO 2007/031875. In one embodiment, the humanized B-Ly1 antibody has variable region of the heavy chain (VH) selected from group of SEQ ID NO: 5 to SEQ ID NO: 21 (B-HH2 to B-HH9 and B-HL8 to B-HL17 of WO 2005/044859 and WO 2007/031875). In one specific embodiment, such variable domain is selected from the group consisting of SEQ ID NOs: 5, 6, 9, 11, 13, 15 and 17 (B-HH2, BHH-3, B-HH6, B-HH8, B-HL8, B-HL11 and B-HL13 of WO 2005/044859 and WO 2007/031875). In one specific embodiment, the humanized B-Ly1 antibody has variable region of the light chain (VL) of SEQ ID NO: 22 (B-KV1 of WO 2005/044859 and WO 2007/031875). In one specific embodiment, the humanized B-Ly1 antibody has a variable region of the heavy chain (VH) of SEQ ID NO: 9 (B-HH6 of WO 2005/044859 and WO 2007/031875) and a variable region of the light chain (VL) of SEQ ID NO: 22 (B-KV1 of WO 2005/044859 and WO 2007/031875). Furthermore, in one embodiment, the humanized B-Ly1 antibody is an IgG1 antibody. According to one aspect of the invention such afucosylated humanized B-Ly1 antibodies are glycoengineered (GE) in the Fc region according to the procedures described in WO 2005/044859, WO 2004/065540, WO 2007/031875, Umana, P. et al., Nature Biotechnol. 17 (1999) 176-180 and WO 99/154342. In one embodiment, the parent non-substituted antibody according to the invention is the afucosylated glyco-engineered humanized B-Ly1 B-HH6-B-KV1 GE. In one embodiment, the parent non-substituted antibody according to the invention is obinutuzumab (recommended INN, WHO Drug Information, Vol. 26, No. 4, 2012, p. 453). As used herein, obinutuzumab is synonymous for GA101. This replaces all previous versions (e.g. Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124).

In a preferred embodiment, the parent non-substituted antibody is a type I anti-CD20 antibody. One essential property of type I and type II anti-CD20 antibodies is their mode of binding. In particular, type I and type II anti-CD20 antibodies can be classified by the ratio of the binding capacities to CD20 on Raji cells (ATCC-No. CCL-86) of said anti-CD20 antibody compared to rituximab. The type I anti-CD20 antibodies have a ratio of the binding capacities to CD20 on Raji cells (ATCC No. CCL-86) of said anti-CD20 antibody compared to rituximab of 0.8 to 1.2, preferably of 0.9 to 1.1. Preferred type I parent non-substituted anti-CD20 antibodies include rituximab, in EP2000149B1 (Anderson et. al., see FIGS. 4 and 5), 1F5 IgG2a (ECACC, hybridoma; Press et al., Blood 69/2:584-591 (1987)), HI47 IgG3 (ECACC, hybridoma), 2C6 IgG1 (as disclosed in WO 2005/103081), 2F2 IgG1 or ofatumumab (as disclosed and WO 2004/035607 and WO 2005/103081) and 2H7 IgG1 (as disclosed in WO 2004/056312) and WO 2006/084264 (including but not limited to the variants disclosed in tables 1 and 2). Preferably said type I parent non-substituted anti-CD20 antibody is a monoclonal antibody that binds to the same epitope as rituximab. In one embodiment, a type I anti-CD20 antibody is provided, comprising a variant heavy chain region comprising an amino acid substitution relative to the parent non-substituted heavy chain region, wherein the heavy chain region of the parent non-substituted antibody comprises the amino acid residue Pro151, wherein the residues are numbered according to the EU index as in Kabat, and wherein said substitution is at said amino acid residue Pro151, wherein direct cell death induced by the antibody comprising the variant heavy chain region is altered compared to direct cell death induced by the antibody comprising the parent non-substituted heavy chain region. In another embodiment, Pro151 is substituted with an amino acid which is either smaller or larger than proline. In a preferred embodiment, the parent non-substituted antibody is rituximab.

In another preferred embodiment, the parent non-substituted antibody is a type II anti-CD20 antibody. The type II anti-CD20 antibodies have a ratio of the binding capacities to CD20 on Raji cells (ATCC No. CCL-86) of said anti-CD20 antibody compared to Rituximab of 0.3 to 0.6, preferably of 0.35 to 0.55, more preferably 0.4 to 0.5. Preferred type II parent non-substituted anti-CD20 antibodies comprise, obinutuzumab, tositumomab (B1 IgG2a), humanized B-Ly1 antibody IgG1 (a chimeric humanized IgG1 antibody as disclosed in WO 2005/044859), 11B8 IgG1 (as disclosed in WO 2004/035607), and AT80 IgG1. Preferably said type II parent non-substituted anti-CD20 antibody is a monoclonal antibody that binds to the same epitope as humanized B-Ly1 antibody (as disclosed in WO 2005/044859). In a further embodiment, a type II anti-CD20 antibody is provided, comprising a variant heavy chain region comprising an amino acid substitution relative to the parent non-substituted heavy chain region, wherein the heavy chain region of the parent non-substituted antibody comprises the amino acid residue Pro151, wherein the residues are numbered according to the EU index as in Kabat, and wherein said substitution is at said amino acid residue Pro151, wherein direct cell death induced by the antibody comprising the variant heavy chain region is altered compared to direct cell death induced by the antibody comprising the parent non-substituted heavy chain region. In another embodiment, Pro151 is substituted with an amino acid which is either smaller or larger than proline. In a preferred embodiment, the parent non-substituted antibody is obinutuzumab.

In a further aspect of the present invention, the amino acid sequence of the parent antibody is modified to generate an antibody with altered ability to induce direct cell death resulting from complexing the modified antibody with its target antigen. In one embodiment, an antibody is provided, comprising a variant heavy chain region comprising at least one amino acid substitution relative to the parent non-substituted heavy chain region, wherein the heavy chain region of the parent non-substituted antibody comprises at least one of the amino acid residues selected from the group consisting of Val11, Leu11 and Pro151, and wherein said substitution is at one of said amino acid residues selected from the group consisting of Val11, Leu11 and Pro151, wherein direct cell death induced by the antibody comprising the variant heavy chain region is increased compared to direct cell death induced by the antibody comprising the parent non-substituted heavy chain region. In still a further embodiment direct cell death induced by the antibody comprising the variant heavy chain region is increased to at least 110% of the direct cell death induced by the antibody comprising the parent non-substituted heavy chain region. In a preferred embodiment direct cell death induced by the antibody comprising the variant heavy chain region is increased to at least 120% of the direct cell death induced by the antibody comprising the parent non-substituted heavy chain region. In further preferred embodiments direct cell death induced by the antibody comprising the variant heavy chain region is increased to at least 130%, to at least 140%, to at least 150%, to at least 160%, to at least 170%, to at least 180%, to at least 190% to at least 200% of the direct cell death induced by the antibody comprising the parent non-substituted heavy chain region. In yet a further preferred embodiment direct cell death induced by the antibody comprising the variant heavy chain region is increased to 120% to 200% of the direct cell death induced by the antibody comprising the parent non-substituted heavy chain region. In a further embodiment induction of direct cell death may be measured by Annexin V binding and PI staining. In yet a further aspect of the present invention, direct cell death induced by the antibody comprising the variant heavy chain region is decreased compared to direct cell death induced by the antibody comprising the parent non-substituted heavy chain region. In still a further embodiment direct cell death induced by the antibody comprising the variant heavy chain region is decreased to 90% or less of the direct cell death induced by the antibody comprising the parent non-substituted heavy chain region. In a preferred embodiment direct cell death induced by the antibody comprising the variant heavy chain region is decreased to 80% or less of the direct cell death induced by the antibody comprising the parent non-substituted heavy chain region. In further preferred embodiments direct cell death induced by the antibody comprising the variant heavy chain region is decreased to 70% or less, to 60% or less, to 50% or less, to 40% or less, to 30% or less, to 20% or less, to 10% or less of the direct cell death induced by the antibody comprising the parent non-substituted heavy chain region. In yet a further preferred embodiment direct cell death induced by the antibody comprising the variant heavy chain region is decreased to 10% to 80% of the direct cell death induced by the antibody comprising the parent non-substituted heavy chain region. In still another preferred embodiment, direct cell death induced by the antibody comprising the variant heavy chain region is abolished. In a further embodiment induction of direct cell death may be measured by Annexin V binding and PI staining.

In one embodiment, an antibody is provided, comprising a variant heavy chain region comprising at least one amino acid substitution relative to the parent non-substituted heavy chain region, wherein the heavy chain region of the parent non-substituted antibody comprises the amino acid residue Pro151, wherein the residues are numbered according to the EU index as in Kabat, and wherein said substitution is at said amino acid residue Pro151, wherein direct cell death induced by the antibody comprising the variant heavy chain region is increased compared to direct cell death induced by the antibody comprising the parent non-substituted heavy chain region. In another embodiment, direct cell death induced by the antibody comprising the variant heavy chain region is decreased compared to direct cell death induced by the antibody comprising the parent non-substituted heavy chain region.

In one embodiment, an antibody is provided, comprising a variant heavy chain region comprising at least one amino acid substitution relative to the parent non-substituted heavy chain region, wherein the heavy chain region of the parent non-substituted antibody comprises at least one of the amino acid residues selected from the group consisting of Val11, Leu11 and Pro151, and wherein said substitution is at one of said amino acid residues selected from the group consisting of Val11, Leu11 and Pro151, wherein direct cell death induced by the antibody comprising the variant heavy chain region is altered compared to direct cell death induced by the antibody comprising the parent non-substituted heavy chain region, wherein at least one of the amino acid residues selected from the group consisting of Val11, Leu11 and Pro151 is substituted with at least one of the amino acid residues selected from the group consisting of alanine and glycine, wherein direct cell death induced by the antibody comprising the variant heavy chain region is decreased compared to direct cell death induced by the antibody comprising the parent non-substituted heavy chain region. In a further embodiment, at least one of the amino acid residues selected from the group consisting of Val11, Leu11 and Pro151 is substituted with at least one of the amino acid residues selected from the group consisting of phenylalanine, threonine and tryptophan, wherein direct cell death induced by the antibody comprising the variant heavy chain region is increased compared to direct cell death induced by the antibody comprising the parent non-substituted heavy chain region. In a preferred embodiment, the parent non-substituted antibody is rituximab. In another preferred embodiment, the parent non-substituted antibody is obinutuzumab.

In another aspect of the invention, the antibodies comprising one or more amino acid substitutions in the heavy chain CH1 and VH regions may further comprise an Fc region variant.

According to the invention an Fc region can be engineered to produce a variant with altered binding affinity for one or more FcRs. In another embodiment of the invention one or more amino acid residues of the Fc region can be modified in order to alter (increase or decrease) binding to an FcR. In one embodiment, an amino acid substitution is made at one or more of the Fc region residues identified as affecting FcR binding in order to generate such an Fc region variant. In preferred embodiments, no more than one to about ten Fc region residues will be deleted or substituted. The Fc regions herein comprising one or more amino acid modifications (including but not limited to substitutions) will preferably retain at least about 80%, and preferably at least about 90%, and most preferably at least about 95%, of the parent Fc region sequence or of a native sequence human Fc region.

In one aspect the present invention is directed to antibodies as disclosed herein having a modification at position 151 in the CH1 region and/or a modification at position 11 in the VH region, resulting with altered signaling behavior of the modified antibodies, said antibodies comprising further modifications in the Fc region of the antibodies resulting with altered induction of antibody-dependent cell-mediated cytotoxicity (ADCC), complement dependent cytotoxicity (CDC) and antibody dependent cellular phagocytosis (ADCP). One embodiment of the invention encompasses polypeptides comprising an Fc region of an antibody, comprising the addition, substitution, or deletion of at least one amino acid residue to the Fc region resulting in reduced or ablated affinity for at least one Fc receptor. The Fc region interacts with a number of receptors or ligands including but not limited to Fc receptors (including but not limited to, FcγRI, FcγRIIA, FcγRIIIA), the complement protein C1q, and other molecules such as proteins A and G. These interactions are essential for a variety of effector functions and downstream signaling events including, but not limited to, antibody-dependent cell-mediated cytotoxicity (ADCC), antibody-dependent cellular phagocytosis (ADCP) and complement dependent cytotoxicity (CDC). Accordingly, in certain embodiments the variants of the invention have reduced or ablated affinity for an Fc receptor responsible for an effector function compared to an antibody having the same amino acid sequence as the antibody comprising a variant of the invention but not comprising the addition, substitution, or deletion of at least one amino acid residue to the Fc region (also referred to herein as a "parent non-substituted" or "parent antibody"). In certain embodiments, antibodies comprising a CH1 and/or VH and/or Fc variant of the invention comprise at least one or more of the following properties: increased or decreased induction of direct cell death, reduced or ablated effector (ADCC and/or CDC and/or ADCP) function, reduced or ablated binding to Fc receptors, reduced or ablated binding to C1q, reduced or ablated toxicities and reduced or ablated infusion reaction (cytokine release syndrome). More specifically, embodiments of the invention provide antibodies with increased induction of direct cell death and reduced affinity for Fc receptors (including but not limited to, FcγRT, FcγRII, FcγRIIIA) and/or reduced affinity for the complement protein C1q. Accordingly, in one aspect, the present invention is directed to antibodies comprising at least one modification at position Pro151 in the CH1 region and/or Val11 in the VH region, said modifications resulting with altered induction of direct cell death, wherein said modified antibodies further comprise at least one modification in the Fc region of the antibodies leading to reduced or ablated effector (ADCC and/or CDC and/or ADCP) function. In yet a further embodiment the present invention is directed to antibodies comprising at least one modification at position Pro151 in the CH1 region and/or Val11 in the VH region, said modifications resulting with altered induction of direct cell death, wherein said modified antibodies further comprise at least one modification in the Fc region of the antibodies leading to reduced or ablated infusion reaction (cytokine release syndrome) compared to the parent non-modified antibody. A preferred embodiment of the invention is an antibody as disclosed herein, comprising said at least one substitution at an amino acid residue selected from the group consisting of Val11, Leu11 and Pro151, further comprising at least one additional amino acid substitution in the Fc region, wherein the parent non-substituted heavy chain region comprises the amino acid residues Leu234, Leu235 and Pro329, wherein the variant heavy chain region comprises the amino acid substitutions Leu234Ala, Leu235Ala and Pro329Gly relative to the parent non-substituted heavy chain region, and wherein binding to FcγR and C1q is abolished, wherein Fc-mediated effector function is abolished. In another preferred embodiment an antibody as disclosed herein comprising at least one of said amino acid substitutions at positions selected from the group consisting of Val11, Leu11 and Pro151 is provided, wherein the parent non-substituted heavy chain region comprises the amino acid residues Leu234, Leu235 and Pro329, wherein the variant heavy chain region comprises the amino acid substitutions Leu234Ala, Leu235Ala and Pro329Gly relative to the parent non-substituted heavy chain region, and wherein infusion reaction (cytokine release syndrome) is abolished. In a preferred embodiment, the parent non-substituted antibody is rituximab. In another preferred embodiment, the parent non-substituted antibody is obinutuzumab.

In another embodiment, an antibody is provided, comprising a variant heavy chain region comprising at least one amino acid substitution relative to the parent non-substituted heavy chain region, wherein the heavy chain region of the parent non-substituted antibody comprises the amino acid residue Pro151, wherein the residues are numbered according to the EU index as in Kabat, and wherein said substitution is at said amino acid residue Pro151, wherein direct cell death induced by the antibody comprising the variant heavy chain region is altered compared to direct cell death induced by the antibody comprising the parent non-substituted heavy chain region. In a further embodiment Pro151 is substituted with an amino acid selected from the group consisting of phenylalanine and alanine. In a further aspect of the invention Pro151 is substituted with alanine, wherein direct cell death induced by the antibody comprising the variant heavy chain region is decreased compared to direct cell death induced by the antibody comprising the parent non-substituted heavy chain region. In a preferred embodiment, Pro151 is substituted with phenylalanine, wherein direct cell death induced by the antibody comprising the variant heavy chain region is increased compared to direct cell death induced by the antibody comprising the parent non-substituted heavy chain region. In yet a further preferred embodiment, the parent non-substituted antibody is obinutuzumab and the variant heavy chain region comprises the amino acid substitution Pro151Phe of the CH1 region, wherein induction of direct cell death is increased compared to direct cell death induced by obinutuzumab. In another preferred embodiment, the parent non-substituted antibody is rituximab and the variant heavy chain region comprises the amino acid substitution Pro151Phe of the CH1 region, wherein induction of direct cell death is increased compared to direct cell death induced by rituximab.

In a further embodiment an antibody is provided, comprising a variant heavy chain region comprising at least one amino acid substitution relative to the parent non-substituted heavy chain region, wherein the heavy chain region of the parent non-substituted antibody comprises the amino acid residue Pro151, wherein the residues are numbered according to the EU index as in Kabat, and wherein said substitution is at said amino acid residue Pro151, wherein direct cell death induced by the antibody comprising the variant heavy chain region is altered compared to direct cell death induced by the antibody comprising the parent non-substituted heavy chain region, wherein the heavy chain region of the parent non-substituted antibody comprises the amino acid residue Val11, wherein the residues are numbered according to Kabat numbering, said variant heavy chain region comprising a further amino acid substitution relative to the parent non-substituted heavy chain region, wherein said further substitution is at said amino acid residue Val11, wherein direct cell death induced by the antibody comprising the variant heavy chain region is altered compared to direct cell death induced by the antibody comprising valine at position Val11. In a further embodiment an antibody is provided comprising a variant heavy chain region comprising at least one amino acid substitution relative to the parent non-substituted heavy chain region, wherein the heavy chain region of the parent non-substituted antibody comprises the amino acid residue Val11, wherein the residues are numbered according to Kabat numbering, and wherein said substitution is at said amino acid residue Val11, wherein direct cell death induced by the antibody comprising the variant heavy chain region is altered compared to direct cell death induced by the antibody comprising the parent non-substituted heavy chain region. In a preferred embodiment, the parent non-substituted antibody is an anti-CD20 antibody. In another preferred embodiment, the parent non-substituted antibody is a type I anti-CD20 antibody. In still another preferred embodiment, the parent non-substituted antibody is a type II anti-CD20 antibody. In a specific embodiment, the parent non-substituted antibody is obinutuzumab. In another specific embodiment, the parent non-substituted antibody is rituximab. In one embodiment, direct cell death induced by the antibody comprising the variant heavy chain region is increased compared to direct cell death induced by the antibody comprising valine at position Val11. In one embodiment, direct cell death induced by the antibody comprising the variant heavy chain region is decreased compared to direct cell death induced by the antibody comprising valine at position Val11.

In a further embodiment a modified antibody as disclosed herein is provided, wherein the heavy chain region of the parent non-substituted antibody comprises the amino acid residue Val11, wherein the residues are numbered according to Kabat numbering, said variant heavy chain region comprising an amino acid substitution relative to the parent non-substituted heavy chain region, wherein said substitution is at said amino acid residue Val11, wherein direct cell death induced by the antibody comprising the variant heavy chain region is altered compared to direct cell death induced by the antibody comprising valine at position Val11, wherein Val11 is substituted with an amino acid selected from the group consisting of alanine, glycine, phenylalanine, threonine and tryptophan. In a further aspect of the invention, Val11 is substituted with an amino acid selected from the group consisting of alanine and glycine, wherein direct cell death induced by the antibody comprising the variant heavy chain region is decreased compared to direct cell death induced by the antibody comprising valine at position Vail 1. In a further aspect of the invention Val11 is substituted with an amino acid selected from the group consisting of phenylalanine, threonine and tryptophan, wherein direct cell death induced by the antibody comprising the variant heavy chain region is increased compared to direct cell death induced by the antibody comprising valine at position Val11. In a preferred embodiment, the parent non-substituted antibody is obinutuzumab. In another preferred embodiment, the parent non-substituted antibody is rituximab.

In a specific aspect of the present invention, a modified antibody is provided, comprising a variant CH1 and/or VH region and a variant Fc region compared to the respective parent non-substituted antibody. Accordingly, in one embodiment, an antibody as disclosed herein is provided, wherein the parent non-substituted heavy chain region comprises the amino acid residues Leu234, Leu235 and Pro329, wherein the residues are numbered according to the EU index as in Kabat, wherein the variant heavy chain region comprises the amino acid substitutions Leu234Ala, Leu235Ala and Pro329Gly relative to the parent non-substituted heavy chain region, and wherein binding to FcγR and Clq is abolished, wherein Fc-mediated effector function is abolished. In a further embodiment the modification as disclosed herein lead to reduced or ablated effector (ADCC and/or CDC and/or ADCP) function. In a specific embodiment said variant heavy chain region comprises the following amino acid substitutions relative to the parent non-substituted heavy chain region: Pro151Phe of the CH1 region, Val11Phe of the VH region and Leu234Ala, Leu235Ala and Pro329Gly of the Fc region. In a preferred embodiment the variant heavy chain region comprises the following amino acid substitutions relative to the parent non-substituted heavy chain region: Pro151Phe of the CH1 region and Leu234Ala, Leu235Ala and Pro329Gly of the Fc region. In another specific embodiment, the parent non-modified antibody is obinutuzumab and the variant heavy chain region comprises the following amino acid substitutions: Pro151Phe of the CH1 region, Val11Phe of the VH region and Leu234Ala, Leu235Ala and Pro329Gly of the Fc region. In a preferred embodiment, the parent non-substituted antibody is obinutuzumab and the variant heavy chain region comprises the following amino acid substitutions: Pro151Phe of the CH1 region and Leu234Ala, Leu235Ala and Pro329Gly of the Fc region. In another specific embodiment, the parent non-substituted antibody is rituximab and the variant heavy chain region comprises the following amino acid substitutions: Pro151Phe of the CH1 region, Val11Phe of the VH region and Leu234Ala, Leu235Ala and Pro329Gly of the Fc region. In a preferred embodiment, the parent non-substituted antibody is rituximab and the variant heavy chain region comprises the following amino acid substitutions: Pro151Phe of the CH1 region and Leu234Ala, Leu235Ala and Pro329Gly of the Fc region.

In certain specific embodiments the present invention is directed to modified antibodies that have increased ability to induce apoptosis compared to the corresponding non-modified parent antibody. For example, a parent antibody that has little or no ability to induce apoptosis may be modified according to the present invention to generate a modified antibody that does have the ability to induce apoptosis or that has an increased ability to induce apoptosis. The present invention is also directed to modified antibodies that have increased ability to induce growth arrest or cell differentiation as compared to the corresponding non-modified parent antibody.

For example, a parent antibody that has little or no ability to induce growth arrest or cell differentiation may be modified according to the present invention to generate a modified antibody that does have the ability to induce growth arrest or differentiation or that has an increased ability to induce growth arrest or differentiation.

In another embodiment, antibodies of the invention are any of any class (for example, but not limited to IgG, IgM, and IgE). In certain embodiments, antibodies of the invention are members of the IgG class of antibodies. In a specific embodiment, antibodies of the invention are of the IgG1, IgG2 or IgG4 subclass. In another specific embodiment, antibodies of the invention are of the IgG1 subclass and comprise the amino acid residues Pro151, Leu234, Leu235 and Pro329, wherein the variant heavy chain region comprise the following amino acid substitutions: Pro151Phe of the CH1 region and Leu234Ala, Leu235Ala Pro329Gly of the Fc region. In another embodiment, antibodies comprising a variant heavy chain region are provided, wherein induction of direct cell death is increased compared to the direct cell death induced by an antibody comprising the parent non-modified antibody heavy chain region, and wherein the effector (ADCC and/or CDC and/or ADCP) functions are reduced or ablated. In certain embodiments, the modified antibodies of the present invention are produced by combining a Fab domain comprising one or more of the amino acid substitutions disclosed herein, with an Fc domain comprising one or more of the amino acid substitutions disclosed herein. In other embodiments modified antibodies of the invention are produced by modifying a Fab domain and/or an Fc domain-containing antibody by introducing one or more of the amino acid substitutions into the Fab and/or Fc domain.

In one aspect of the invention, antibodies according to the present invention have an altered pattern of glycosylation in the Fc region, preferably having a reduced level of fucose residues. In another embodiment, the oligosaccharides of the Fc region are preferably bisected. These glycoengineered antibodies have an increased ADCC. In one embodiment, an antibody as disclosed herein is provided with an amount of fucose of 60% or less of the total amount of oligosaccharides (sugars) at the amino acid residue Asn297 in the heavy chain region. In one embodiment, the amount of fucose is between 40% and 60% of the oligosaccharides of the Fc region at Asn297. In another embodiment, the amount of fucose is 50% or less, and in still another embodiment the amount of fucose is 30% or less of the oligosaccharides of the Fc region at Asn297. According to the invention "amount of fucose" means the amount of said oligosaccharide (fucose) within the oligosaccharide (sugar) chain at Asn297, related to the sum of all oligosaccharides (sugars) attached to Asn297 (e.g., complex, hybrid and high mannose structures) measured by MALDI-TOF mass spectrometry and calculated as average value (a detailed procedure to determine the amount of fucose, is disclosed e.g. WO 2008/077546). Furthermore, in one embodiment, the oligosaccharides of the Fc region are bisected. The afucosylated antibody according to the invention can be expressed in a glycomodified host cell engineered to express at least one nucleic acid encoding a polypeptide having GnTIII activity in an amount sufficient to partially fucosylate the oligosaccharides in the Fc region. In one embodiment, the polypeptide having GnTIII activity is a fusion polypeptide. Alternatively, α1,6-fucosyltransferase activity of the host cell can be decreased or eliminated according to U.S. Pat. No. 6,946,292 to generate glycomodified host cells. The amount of antibody fucosylation can be predetermined e.g., either by fermentation conditions (e.g. fermentation time) or by combination of at least two antibodies with different fucosylation amount. Such afucosylated antibodies and respective glycoengineering methods are disclosed in WO 2005/044859, WO 2004/065540, WO 2007/031875, Umana, P., et al., Nature Biotechnol. 17 (1999) 176-180, WO 99/154342, WO 2005/018572, WO 2006/116260, WO 2006/114700, WO 2005/011735, WO 2005/027966, WO 97/028267, US 2006/0134709, US 2005/0054048, US 2005/0152894, WO 2003/035835, WO 2000/061739. These glycoengineered antibodies have an increased ADCC. Other glycoengineering methods yielding afucosylated antibodies according to some aspects of the invention are described e.g. in Niwa, R., et al., J. Immunol. Methods 306 (2005) 151-160; Shinkawa, T., et al., J. Biol. Chem, 278 (2003) 3466-3473; WO 03/055993 or US 2005/0249722.

Another aspect of the invention is glycoengineered antibodies as disclosed herein. In a particular embodiment, the altered glycosylation of the modified antibody comprises a reduced level of fucose residues in the Fc region. See U.S. Pat. Appl. Pub. No. 2005/0123546 to Umaña et al., the entire contents of which is hereby incorporated by reference in its entirety. In a specific embodiment the modified antibodies comprise an amount of fucose of 60% or less of the total amount of oligosaccharides (sugars) at the amino acid residue Asn297 in the heavy chain region. Another aspect of the invention is an afucosylated anti-CD20 antibody of IgG1 or IgG3 isotype (preferably of IgG1 isotype) specifically binding to CD20 with an amount of fucose of 60% or less of the total amount of oligosaccharides (sugars) at Asn297, for the treatment of cancer. Another aspect of the invention is the use of an afucosylated anti-CD20 antibody of IgG1 or IgG3 isotype (preferably of IgG1 isotype) specifically binding to CD20 with an amount of fucose of 60% or less of the total amount of oligosaccharides (sugars) at Asn297, for the manufacture of a medicament for the treatment of cancer. In one embodiment, the amount of fucose is between 60% and 40% of the total amount of oligosaccharides (sugars) at Asn297. In one embodiment, the amount of fucose is between 0% and 20% of the total amount of oligosaccharides (sugars) at Asn297. In another embodiment, the Type I or Type II anti-CD20 antibodies have undergone polypeptide engineering as taught in U.S. Pat. No. 6,737,056 to Presta or U.S. Pat. Appl. Pub. No. 2004 0185045 (Macrogenics) or U.S. Pat. Appl. Pub. No. 2004 0132101 (Xencor), each of which is hereby incorporated by reference in its entirety. The invention is further directed to methods of making such engineered Type I or Type II antibodies and to methods of using such antibodies in the treatment of various B cell disorders, including B cell lymphomas.

A further aspect of the present invention is the provision of modified anti-CD20 antibodies. In a preferred embodiment, the antibody as disclosed herein specifically binds to CD20. In certain embodiments, the modified anti-CD20 antibody as disclosed herein has a dissociation constant (Kd) of ≤1 µM, ≤100 nM, ≤10 nM, ≤1 nM, ≤0.1 nM, ≤0.01 nM, or ≤0.001 nM, from $10^{-8}$ M to $10^{-13}$ M or from $10^{-9}$ M to $10^{-13}$ M. In a preferred embodiment, the antibody as disclosed herein specifically binds to CD20 with a dissociation constant (Kd) on cells of 10 nM or less as determined by scatchard analysis. In one embodiment, the present invention is directed to a modified anti-CD20 antibody comprising a substitution in the heavy chain region compared to a type I parent anti-CD20 antibody, wherein the substitutions result in increased induction of apoptosis by the modified anti-CD20 antibody. In another embodiment, the present invention is directed to engineered type II anti-CD20 antibodies having decreased ADCC as a result of engineering for decreased effector function and without loss of substantial ability to induce apoptosis. In one embodiment, the type II anti-CD20 antibodies comprise a substitution in one or more amino acids in the heavy chain compared to a parent molecule. In another embodiment, the present invention is directed to a modified anti-CD20 antibody, comprising a variant heavy chain region, wherein the heavy chain region of the parent non-substituted antibody comprises at least one of the amino acid residues selected from the group consisting of Val11, Leu11 and Pro151, said variant heavy chain region comprising at least one amino acid substitution relative to the parent non-substituted heavy chain region, wherein said substitution is at one of said amino acid residues selected from the group consisting of Val11, Leu11 and Pro151, wherein direct cell death induced by the antibody comprising the variant heavy chain region is altered compared to direct cell death induced by the antibody comprising the parent non-substituted heavy chain region. In another embodiment, direct cell death induced by the antibody comprising the variant heavy chain region according to the invention is increased compared to direct cell death induced by the antibody comprising the parent non-substituted heavy chain region. In another embodiment, the Type I and/or Type II anti-CD20 antibodies have been engineered to have an altered pattern of glycosylation in the Fc region. In a particular embodiment, the altered glycosylation of the modified antibodies comprises an increased level of bisected complex residues in the Fc region.

In a further embodiment of the present invention, a modified anti-CD20 antibody is provided, comprising a variant CH1 and/or VH region as disclosed herein and a variant Fc region as disclosed herein compared to the respective parent non-substituted antibody. In one embodiment an anti-CD20 antibody is provided, comprising a variant heavy chain region, wherein the heavy chain region of the parent non-substituted antibody comprises the amino acid residues Pro151, Leu234, Leu235 and Pro329, said variant heavy chain region comprising the following amino acid substitutions: Pro151Phe, Leu234Ala, Leu235Ala and Pro329Gly relative to the parent non-substituted heavy chain region, wherein induction of direct cell death is increased and wherein effector (ADCC and/or CDC and/or ADCP) function is decreased compared to direct cell death and effector function induced by an antibody comprising the parent non-substituted antibody heavy chain region. In a further embodiment an anti-CD20 antibody is provided, comprising a variant heavy chain region, wherein the heavy chain region of the parent non-substituted antibody comprises at least one of the amino acid residues selected from the group consisting of Val11, Leu234, Leu235 and Pro329, said variant heavy chain region comprising the following amino acid substitutions: Val11Phe, Leu234Ala, Leu235Ala and Pro329G relative to the parent non-substituted heavy chain region, wherein induction of direct cell death is increased and wherein effector (ADCC and/or CDC and/or ADCP) function is decreased compared to direct cell death and effector function induced by an antibody comprising the parent non-substituted antibody heavy chain region. In a further aspect said antibodies exhibit a reduced affinity to the human FcγRIIIA and/or FcγRIIA and/or FcγRI compared to antibodies with wildtype Fc region. In a further aspect, said modifications in the Fc region lead to reduced or ablated effector (ADCC and/or CDC and/or ADCP) function, reduced or ablated binding to Fc receptors, reduced or ablated binding to C1q, reduced or ablated toxicities and reduced or ablated infusion reaction (cytokine release syndrome).

In still another embodiment, the heavy chain variants of the present invention exhibit a reduced affinity to a human Fc receptor (FcγR) and/or a human complement receptor as compared to the polypeptide comprising the wildtype Fc polypeptide. In another embodiment, said antibody comprising a variant heavy chain region exhibits a reduced affinity to a human Fc receptor (FcγR) and/or a human complement receptor as compared to the polypeptide comprising the wildtype human Fc region. In a further embodiment the affinity to at least one of the FcγRI, FcγRII, FcγRIIIA is reduced, in a still further embodiment the affinity to the FcγRI and FcγRIIIA is reduced, and in a still further embodiment the affinity to the FcγRI, FcγRII and FcγRIIIA is reduced, in still a further aspect of the invention the affinity to the FcγRI receptor, FcγRIIIA receptor and C1q is reduced, and in still a further aspect of the invention the affinity to the FcγRI, FcγRII, FcγRIIIA and C1q receptor is reduced. In still a further embodiment the ADCC induced by said antibody comprising a heavy chain variant is reduced and in a preferred embodiment the ADCC is reduced to at least 20% of the ADCC induced by the polypeptide comprising the wildtype Fc polypeptide. In still a further aspect of the invention, the ADCC and CDC induced by the antibody comprising the wildtype Fc polypeptide is decreased or ablated and in a still further aspect the antibody comprising an Fc variant disclosed herein exhibit a decreased ADCC, CDC and ADCP compared to the polypeptide comprising the wildtype Fc polypeptide.

While, it is preferred to alter binding to a FcγR, Fc region variants with altered binding affinity for the neonatal receptor (FcRn) are also contemplated herein. Fc region variants with improved affinity for FcRn are anticipated to have longer serum half-lives, and such molecules will have useful applications in methods of treating mammals where long half-life of the administered polypeptide is desired, e.g., to treat a chronic disease or disorder. Fc region variants with decreased FcRn binding affinity, on the contrary, are expected to have shorter half-lives, and such molecules may, for example, be administered to a mammal where a shortened circulation time may be advantageous, e.g. for in vivo diagnostic imaging or for polypeptides which have toxic side effects when left circulating in the blood stream for extended periods, etc. Fc region variants with decreased FcRn binding affinity are anticipated to be less likely to cross the placenta, and thus may be utilized in the treatment of diseases or disorders in pregnant women. Fc region variants with altered binding affinity for FcRn include those comprising an Fc region amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447. Those which display reduced binding to FcRn will generally comprise an Fc region amino acid modification at any one or more of amino acid positions 252, 253, 254, 255, 288, 309, 386, 388, 400, 415, 433, 435, 436, 439 or 447; and those with increased binding to FcRn will usually comprise an Fc region amino acid modification at any one or more of amino acid positions 238, 256, 265, 272, 286, 303, 305, 307, 311, 312, 317, 340, 356, 360, 362, 376, 378, 380, 382, 413, 424 or 434.

In another aspect of the invention an anti-CD20 antibody is provided, comprising a variant heavy chain region, wherein the heavy chain region of the parent non-substituted antibody comprises the amino acid residue Pro151, wherein the residues are numbered according to the EU index as in Kabat, said variant heavy chain region comprising the amino acid substitution Pro151Phe relative to the parent non-substituted antibody, wherein direct cell death induced by the antibody comprising the variant heavy chain region is increased compared to direct cell death induced by the antibody comprising the parent non-substituted heavy chain region.

In still another aspect of the invention an anti-CD20 antibody is provided, comprising a variant heavy chain region, wherein the heavy chain region of the parent non-substituted antibody comprises the amino acid residue Pro151, wherein the residues are numbered according to the EU index as in Kabat, said variant heavy chain region comprising the amino acid substitution Pro151Ala relative to the parent non-substituted antibody, wherein direct cell death induced by the antibody comprising the variant heavy chain region is decreased compared to direct cell death induced by the antibody comprising the parent non-substituted heavy chain region.

In still another aspect of the invention an anti-CD20 antibody is provided, comprising a variant heavy chain region, wherein the heavy chain region of the parent non-substituted antibody comprises the amino acid residues Pro151, Leu234, Leu235 and Pro329, said variant heavy chain region comprising the following amino acid substitutions relative to the parent non-substituted antibody: Pro151Phe, Leu234Ala, Leu235Ala and Pro329Gly, wherein direct cell death induced by the antibody comprising the variant heavy chain region is increased compared to direct cell death induced by the antibody comprising the parent non-substituted heavy chain region, and wherein the induction of effector (ADCC and/or CDC and/or ADCP) function is reduced or ablated compared to effector function induced by the antibody comprising the parent non-substituted heavy chain region.

In still another aspect of the invention an anti-CD20 antibody is provided, comprising a variant heavy chain region, wherein the heavy chain region of the parent non-substituted antibody comprises the amino acid residues Pro151 and Pro329, said variant heavy chain region comprising the following amino acid substitutions relative to the parent non-substituted antibody: Pro151Phe and Pro329Gly, wherein direct cell death induced by the antibody comprising the variant heavy chain region is increased compared to direct cell death induced by the antibody comprising the parent non-substituted heavy chain region, and wherein the induction of effector (ADCC and/or CDC and/or ADCP) function is reduced or ablated compared to effector function induced by the antibody comprising the parent non-substituted heavy chain region.

In still another aspect of the invention an anti-CD20 antibody is provided, comprising a variant heavy chain region, wherein the heavy chain region of the parent non-substituted antibody comprises the amino acid residue Val11, said variant heavy chain region comprising the amino acid substitution Val11Phe relative to the parent non-substituted antibody, wherein direct cell death induced by the antibody comprising the variant heavy chain region is increased compared to direct cell death induced by the antibody comprising the parent non-substituted heavy chain region.

In still another aspect of the invention an anti-CD20 antibody is provided, comprising a variant heavy chain region, wherein the heavy chain region of the parent non-substituted antibody comprises the amino acid residue Val11, said variant heavy chain region comprising the amino acid substitution Val11Ala relative to the parent non-substituted antibody, wherein direct cell death induced by the antibody comprising the variant heavy chain region is decreased compared to direct cell death induced by the antibody comprising the parent non-substituted heavy chain region.

In still another aspect of the invention an anti-CD20 antibody is provided, comprising a variant heavy chain region, wherein the heavy chain region of the parent non-substituted antibody comprises the amino acid residues Val11, Leu234, Leu235 and Pro329, said variant heavy chain region comprising the following amino acid substitutions relative to the parent non-substituted antibody: Val11Phe, Leu234Ala, Leu235Ala and Pro329Gly, wherein direct cell death induced by the antibody comprising the variant heavy chain region is increased compared to direct cell death induced by the antibody comprising the parent non-substituted heavy chain region, and wherein the induction of effector (ADCC and/or CDC and/or ADCP) function is reduced or ablated compared to effector function induced by the antibody comprising the parent non-substituted heavy chain region.

In still another aspect of the invention an anti-CD20 antibody is provided, comprising a variant heavy chain region, wherein the heavy chain region of the parent non-substituted antibody comprises the amino acid residues Val11, Leu234, Leu235 and Pro329, said variant heavy chain region comprising the following amino acid substitutions relative to the parent non-substituted antibody: Val11Ala, Leu234Ala, Leu235Ala and Pro329Gly, wherein direct cell death induced by the antibody comprising the variant heavy chain region is decreased compared to direct cell death induced by the antibody comprising the parent non-substituted heavy chain region, and wherein the induction of effector (ADCC and/or CDC and/or ADCP) function is reduced or ablated compared to effector function induced by the antibody comprising the parent non-substituted heavy chain region.

In still another aspect of the invention an anti-CD20 antibody is provided, comprising a variant heavy chain region, wherein the heavy chain region of the parent non-substituted antibody comprises the amino acid residues Val11, Pro151, Leu234, Leu235 and Pro329, said variant heavy chain region comprising the following amino acid substitutions relative to the parent non-substituted antibody: Val11Phe, Pro151Phe, Leu234Ala, Leu235Ala and Pro329Gly, wherein direct cell death induced by the antibody comprising the variant heavy chain region is increased compared to direct cell death induced by the antibody comprising the parent non-substituted heavy chain region, and wherein the induction of effector (ADCC and/or CDC and/or ADCP) function is reduced or ablated compared to effector function induced by the antibody comprising the parent non-substituted heavy chain region.

In a specific embodiment an anti-CD20 antibody comprising a variant heavy chain region is provided, wherein the parent non-substituted antibody is obinutuzumab comprising the amino acid residue Pro151 in the heavy chain region, wherein the residues are numbered according to the EU index as in Kabat, wherein said variant heavy chain region comprises the amino acid substitution Pro151Phe relative to obinutuzumab, wherein direct cell death induced by the antibody comprising the variant heavy chain region is increased compared to direct cell death induced by obinutuzumab.

In a specific embodiment an anti-CD20 antibody comprising a variant heavy chain region is provided, wherein the parent non-substituted antibody is obinutuzumab comprising the amino acid residue Pro151 in the heavy chain region, wherein the residues are numbered according to EU index as in Kabat, wherein said variant heavy chain region comprises the amino acid substitution Pro151Ala relative to obinutuzumab, wherein direct cell death induced by the antibody comprising the variant heavy chain region is decreased compared to direct cell death induced by obinutuzumab.

In a specific embodiment an anti-CD20 antibody comprising a mutated heavy chain is provided, wherein the parent non-mutated antibody is obinutuzumab comprising the amino acid residue Pro151 in the heavy chain, wherein the residues are numbered according to the EU index as in Kabat, wherein said mutated heavy chain comprises the amino acid substitution Pro151Ala relative to obinutuzumab, wherein direct cell death induced by the antibody comprising the mutated heavy chain is decreased compared to direct cell death induced by obinutuzumab.

In a specific embodiment an anti-CD20 antibody comprising a variant heavy chain region is provided, wherein the parent non-substituted antibody is obinutuzumab comprising the amino acid residue Val11 in the heavy chain region, wherein the residues are numbered according to Kabat numbering, wherein said variant heavy chain region comprises the amino acid substitution Val11Thr relative to obinutuzumab, wherein direct cell death induced by the antibody comprising the variant heavy chain region is increased compared to direct cell death induced by obinutuzumab.

In a specific embodiment an anti-CD20 antibody comprising a variant heavy chain region is provided, wherein the parent non-substituted antibody is obinutuzumab comprising the amino acid residue Val11 in the heavy chain region, wherein the residues are numbered according to Kabat numbering, wherein said variant heavy chain region comprises the amino acid substitution Val11Phe relative to obinutuzumab, wherein direct cell death induced by the antibody comprising the variant heavy chain region is increased compared to direct cell death induced by obinutuzumab.

In a specific embodiment an anti-CD20 antibody comprising a variant heavy chain region is provided, wherein the parent non-substituted antibody is obinutuzumab comprising the amino acid residue Val11 in the heavy chain region, wherein the residues are numbered according to Kabat numbering, wherein said variant heavy chain region comprises the amino acid substitution Val11Trp relative to obinutuzumab, wherein direct cell death induced by the antibody comprising the variant heavy chain region is increased compared to direct cell death induced by obinutuzumab.

In a specific embodiment an anti-CD20 antibody comprising a variant heavy chain region is provided, wherein the parent non-substituted antibody is obinutuzumab comprising the amino acid residue Val11 in the heavy chain region, wherein the residues are numbered according to Kabat numbering, wherein said variant heavy chain region comprises the amino acid substitution Val11Ala relative to obinutuzumab, wherein direct cell death induced by the antibody comprising the variant heavy chain region is decreased compared to direct cell death induced by obinutuzumab.

In a specific embodiment an anti-CD20 antibody comprising a variant heavy chain region is provided, wherein the parent non-substituted antibody is obinutuzumab comprising the amino acid residue Val11 in the heavy chain region, wherein the residues are numbered according to Kabat numbering, wherein said variant heavy chain region comprises the amino acid substitution Val11 Gly relative to obinutuzumab, wherein direct cell death induced by the antibody comprising the variant heavy chain region is decreased compared to direct cell death induced by obinutuzumab.

In a further embodiment an antibody comprising a variant heavy chain region is provided, wherein the parent non-substituted antibody is obinutuzumab comprising the amino acid residues Val11, Leu234, Leu235 and Pro329 in the heavy chain region, wherein said variant heavy chain region comprises the following amino acid substitutions relative to obinutuzumab: Val11Phe of the VH region and Leu234Ala, Leu235Ala and Pro329Gly of the Fc region, wherein direct cell death induced by the antibody comprising the variant heavy chain region is increased compared to direct cell death induced by obinutuzumab, and wherein the induction of effector (ADCC and/or CDC and/or ADCP) function is reduced or ablated compared effector function induced by obinutuzumab.

In a further embodiment an antibody comprising a variant heavy chain region is provided, wherein the parent non-substituted antibody is obinutuzumab comprising the amino acid residues Val11, Leu234, Leu235 and Pro329 in the heavy chain region, wherein said variant heavy chain region comprises the following amino acid substitutions relative to obinutuzumab: Val11Ala of the VH region and Leu234Ala, Leu235Ala and Pro329Gly of the Fc region, wherein direct cell death induced by the antibody comprising the variant heavy chain region is decreased compared to direct cell death induced by obinutuzumab, and wherein the induction of effector (ADCC and/or CDC and/or ADCP) function is reduced or ablated compared effector function induced by obinutuzumab.

In a further embodiment an antibody comprising a variant heavy chain region is provided, wherein the parent non-substituted antibody is obinutuzumab comprising the amino acid residues Pro151, Leu234, Leu235 and Pro329 in the heavy chain region, wherein said variant heavy chain region comprises the following amino acid substitutions relative to obinutuzumab: Pro151Phe of the CH1 region and Leu234Ala, Leu235Ala and Pro329Gly of the Fc region, wherein direct cell death induced by the antibody comprising the variant heavy chain region is increased compared to direct cell death induced by obinutuzumab, and wherein the induction of effector (ADCC and/or CDC and/or ADCP) function is reduced or ablated compared effector function induced by obinutuzumab.

In a further embodiment an antibody comprising a variant heavy chain region is provided, wherein the parent non-substituted antibody is obinutuzumab comprising the amino acid residues Pro151, Leu234, Leu235 and Pro329 in the heavy chain region, wherein said variant heavy chain region comprises the following amino acid substitutions relative to obinutuzumab: Pro151Ala of the CH1 region and Leu234Ala, Leu235Ala and Pro329Gly of the Fc region, wherein direct cell death induced by the antibody comprising the variant heavy chain region is decreased compared to direct cell death induced by obinutuzumab, and wherein the induction of effector (ADCC and/or CDC and/or ADCP) function is reduced or ablated compared effector function induced by obinutuzumab.

In a further embodiment an antibody comprising a variant heavy chain region is provided, wherein the parent non-substituted antibody is rituximab comprising the amino acid residue Pro151 in the heavy chain region, wherein said variant heavy chain region comprises the amino acid substitution Pro151Phe relative to rituximab, and wherein direct cell death induced by the antibody comprising the variant heavy chain region is increased compared to direct cell death induced by rituximab.

In a further embodiment an antibody comprising a variant heavy chain region is provided, wherein the parent non-substituted antibody is rituximab comprising the amino acid residue Pro151 in the heavy chain region, wherein said variant heavy chain region comprises the amino acid substitution Pro151Ala relative to rituximab, and wherein direct cell death induced by the antibody comprising the variant heavy chain region is decreased compared to direct cell death induced by rituximab.

In a further embodiment an antibody comprising a variant heavy chain region is provided, wherein the parent non-substituted antibody is rituximab comprising the amino acid residue Leu11 in the heavy chain region, wherein said variant heavy chain region comprises the amino acid substitution Leu11Phe relative to rituximab, and wherein direct cell death induced by the antibody comprising the variant heavy chain region is increased compared to direct cell death induced by rituximab.

In a further embodiment an antibody comprising a variant heavy chain region is provided, wherein the parent non-substituted antibody is rituximab comprising the amino acid residue Leu11 in the heavy chain region, wherein said variant heavy chain region comprises the amino acid substitution Leu11Ala relative to rituximab, and wherein direct cell death induced by the antibody comprising the variant heavy chain region is decreased compared to direct cell death induced by rituximab.

In a further embodiment an antibody comprising a variant heavy chain region is provided, wherein the parent non-substituted antibody is rituximab comprising the amino acid residues Leu11, Leu234, Leu235 and Pro329 in the heavy chain region, wherein said variant heavy chain region comprises the following amino acid substitutions relative to rituximab: Leu11Phe of the VH region and Leu234Ala, Leu235Ala and Pro329Gly of the Fc region, wherein direct cell death induced by the antibody comprising the variant heavy chain region is increased compared to direct cell death induced by ritubimab, and wherein the induction of effector (ADCC and/or CDC and/or ADCP) function is reduced or ablated compared to effector function induced by rituximab.

In a further embodiment an antibody comprising a variant heavy chain region is provided, wherein the parent non-substituted antibody is rituximab comprising the amino acid residues Pro151, Leu234, Leu235 and Pro329 in the heavy chain region, wherein said variant heavy chain region comprises the following amino acid substitutions: Pro151Phe of the CH1 region, and Leu234Ala, Leu235Ala and Pro329Gly of the Fc region relative to rituximab, wherein direct cell death induced by the antibody comprising the variant heavy chain region is increased compared to direct cell death induced by rituximab, and wherein the induction of effector (ADCC and/or CDC and/or ADCP) function is reduced or ablated compared to effector function induced by rituximab.

Antibodies according to the present invention comprising amino acid modifications (substitutions, additions, deletions) may be prepared by methods known in the art. These methods include, but are not limited to, preparation by site-directed (or oligonucleotide-mediated) mutagenesis, PCR mutagenesis, and cassette mutagenesis of an earlier prepared nucleic acid encoding the polypeptide. Site-directed mutagenesis is a preferred method for preparing substitution variants. This technique is well known in the art (see e.g., Carter et a Nucleic Acids Res. 13: 4431-4443 (1985) and Kunkel et. al, Proc. Natl. Acad. Sci. USA 82: 488 (1987), each of which is hereby incorporated by reference in its entirety). Briefly, in carrying out site directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the non-modified starting polypeptide (see, e.g., Vallette et. al, Nuc. Acids Res. 17: 723-733 (1989), hereby incorporated by reference in its entirety). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method according to the invention for preparing the inventive antibody variants, cassette mutagenesis, is based on the technique described by Wells et al, Gene 34: 315-323 (1985), hereby incorporated by reference in its entirety. The starting material is the plasmid (or other vector) comprising the starting polypeptide DNA to be modified. The codon(s) in the starting DNA to be mutated are identified. There must be a unique restriction endonuclease site on each side of the identified mutation site(s). If no such restriction sites exist, they may be generated using the herein-disclosed oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding an antibody variant can be determined, and a nucleic acid sequence encoding such an amino acid sequence variant can be generated synthetically.

Variants and isoforms of the human Fc region are also encompassed by the present invention. For example, variant Fc regions suitable for use in the present invention can be produced according to the methods taught in U.S. Pat. No. 6,737,056 to Presta (Fc region variants with altered effector function due to one or more amino acid modifications); or in U.S. Pat. Appl. Nos. 60/439,498; 60/456,041; 60/514,549; or WO 2004/063351 (variant Fc regions with increased binding affinity due to amino acid modification); or in U.S. patent application Ser. No. 10/672,280 or WO 2004/099249 (Fc variants with altered binding to FcγR due to amino acid modification), each of which is hereby incorporated by reference in its entirety.

By introducing the appropriate amino acid sequence modifications in a parent Fc region, one can generate a variant Fc region which (a) mediates one or more effector functions in the presence of human effector cells more or less effectively and/or (b) binds an Fcγ receptor (FcγR) or Fc neonatal receptor (FcRn) with higher or smaller affinity than the parent polypeptide. Such modified Fc regions will generally comprise at least one amino acid modification in the Fc region.

In preferred embodiments, the parent polypeptide Fc region is a human Fc region, including but not limited to a native human Fc region human IgG1 (A and non-A allotypes), IgG2, IgG3, IgG4, and all allotypes known or discovered from any species Fc region. Such regions have sequences such as those disclosed in U.S. Provisional Patent Application No. 60/678,776, which is hereby incorporated by reference in its entirety.

In certain embodiments, in order to generate an antibody comprising one or more amino acid substitutions in the heavy chain CH1 and VH regions further comprising a modified Fc region with altered effector function (including but not limited to ADCC), the parent polypeptide preferably has pre-existing ADCC activity (e.g., the parent polypeptide comprises a human IgG1 or human IgG3 Fc region). In some embodiments, a modified Fc region with altered ADCC mediates ADCC substantially more or less effectively than an antibody with a native sequence IgG1 or IgG3 Fc region.

The polypeptides of the invention having modified heavy chain regions may be subjected to one or more further modifications, depending on the desired or intended use of the polypeptide. Such modifications involve, for example but are not limited to, further alteration of the amino acid sequence (substitution, insertion and/or deletion of amino acid residues), fusion to heterologous polypeptide(s) and/or covalent modifications. Such further modifications may be made prior to, simultaneously with, or following, the amino acid modification(s) disclosed herein which result in an alteration of signaling activity and/or of Fc receptor binding and/or effector function.

In another aspect of the invention, an antibody provided herein has a dissociation constant (Kd) of ≤1 µM, ≤100 nM, ≤10 nM, ≤1 nM, ≤0.1 nM, ≤0.01 nM, or ≤0.001 nM. Preferably, the dissociation constant is $10^{-8}$ M or less, from $10^{-8}$ M to $10^{-13}$ M, from $10^{-9}$ M to $10^{-13}$ M.

In one aspect of the invention, the dissociation constant Kd is measured by scatchard analysis using Europium labeled antibodies and analyzing the bound/free ratio at different antibody concentrations. $2 \times 10^5$ SU-DHL4 cells are seeded into V-bottom plates (NUNC) in culture medium containing 20% FCS (50 µl). Then, 50 µl Europium-labeled antibodies are added in different concentrations and incubated at 25° C. for 1 h. Thereafter, 150 µl complete medium is added and the plate is centrifuged. The cells are washed 2× by replacing the whole medium, transferred into a new plate and washed again 2×. Finally, the medium is removed after centrifugation and the pellet is resuspended in 200 µl enhancer solution, transferred into a black 96 well plate and put onto a shaker for 10 min. By this step, the coupled Europium is released into the supernatant, the fluorescence is enhanced and then analyzed on a BMG PheraStar machine (ex337/em615). The molarity of the antibodies bound is calculated by usage of relative fluorescence units (RFU) from a standard (Europium-antibody) titration curve. The amount of free antibody is calculated by subtraction of the bound antibody from the signal measured in the total antibody wells. The bound versus free antibody ratio is plotted against the number of bound antibody molecules and the slope of the curve (S) is determined. The affinity of the antibody is determined using the following formula: Kd (M)=1/−S.

According to another embodiment, the dissociation constant Kd is measured by a radiolabeled antigen or Fc receptor binding assay (RIA) performed with the Fab version of an antibody of interest and its antigen as disclosed by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen, et al., J. Mol. Biol. 293 (1999) 865-881). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Sigma-Aldrich P7366), 100 pM or 26 pM [$^{125}$I]-antigen are mixed with serial dilutions of a Fab of interest (e.g., consistent with assessment of the anti-VEGF antibody, Fab-12, in Presta, et al., Cancer Res. 57 (1997) 4593-4599). The Fab of interest is then incubated overnight; however, the incubation may continue for a longer period (e.g., about 65 hours) to ensure that equilibrium is reached. Thereafter, the mixtures are transferred to the capture plate for incubation at room temperature for one hour. The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, the dissociation constant Kd of the antibody is measured using surface plasmon resonance assays using a BIACORE®-2000 or a BIACORE®-3000 (BIAcore, Inc., Piscataway, N.J.) at 25° C. with immobilized antigen or Fc receptor CM5 chips at ~10 response units (RU). Briefly, carboxy methylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensograms. Kd is calculated as the ratio koff/kon. See, e.g., Chen, et al., J. Mol. Biol. 293 (1999) 865-881. If the on-rate exceeds $10^6$ $M^{-1}$ $s^{-1}$ by the surface plasmon resonance assay herein, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In a specific embodiment, the parent non-substituted heavy chain region is from obinutuzumab, as disclosed in SEQ ID NO: 1, and further disclosed herein. The amino acid positions 11, 151, 234, 235 and 329 according to Kabat are underlined.

Obinutuzumab heavy chain amino acid sequence
(SEQ ID NO: 1)
QVQLVQSGAEVKKPGSSVKVSCKASGYAFSYSWINWVRQAPGQGLEWMGR

IFPGDGDTDYNGKFKGRVTITADKSTSTAYMELSSLRSEDTAVYYCARNV

FDGYWLVYWGQGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

In another specific embodiment, the parent non-substituted heavy chain region is from rituximab, as disclosed in SEQ ID NO: 2, and further disclosed herein. The amino acid positions 11, 151, 234, 235 and 329 according to Kabat are underlined.

Rituximab heavy chain amino acid sequence
(SEQ ID NO: 2)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSAASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKAEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

Expression of Modified Antibodies

Methods which are well known to those skilled in the art can be used to construct expression vectors containing the coding sequence of a modified antibody having substantially the same binding specificity of a parent antibody along with appropriate transcriptional/translational control signals. These methods include in vitro recombinant DNA techniques, synthetic techniques and in vivo recombination/genetic recombination. See, for example, the techniques described in Maniatis et al, MOLECULAR CLONING A LABORATORY MANUAL, Cold Spring Harbor Laboratory, N. Y. (1989) and Ausubel et at, CURRENT PROTOCOLS IN MOLECULAR BIOLOGY, Greene Publishing Associates and Wiley Interscience, N.Y (1989).

A variety of host-expression vector systems may be utilized to express the coding sequence of the antibodies of the present invention. Preferably, mammalian cells are used as host cell systems transfected with recombinant plasmid DNA or cosmid DNA expression vectors containing the coding sequence of the protein of interest and the coding sequence of the fusion polypeptide. Most preferably, CHO cells, HEK293-EBNA cells, BHK cells, NSO cells, SP2/0 cells, YO myeloma cells, P3X63 mouse myeloma cells, PER cells, PER.C6 cells or hybridoma cells, other mammalian cells, yeast cells, insect cells, or plant cells are used as host cell system. Some examples of expression systems and selection methods are disclosed in the following references, and references therein: Borth et at, Biotechnol. Bioen. 71(4):266-73 (2000-2001), in Werner et al, Arzneimittelforschung/Drug Res. 48(8):870-80 (1998), in Andersen and Krummen, Curr. Op. Biotechnol. 13:117-123 (2002), in Chadd and Chamow, Curr. Op. Biotechnol. 12:188-194 (2001), and in Giddings, Curr. Op. Biotechnol. 12: 450-454 (2001). In alternate embodiments, other eukaryotic host cell systems may be contemplated, including yeast cells transformed with recombinant yeast expression vectors containing the coding sequence of an antibody of the present invention, such as the expression systems taught in U.S. Pat. Appl. No. 60/344,169 and WO 03/056914 (methods for producing human-like glycoprotein in a non-human eukaryotic host cell) (each of which is hereby incorporated by reference in its entirety); insect cell systems infected with recombinant virus expression vectors (e.g., baculo virus) containing the coding sequence of a modified antibody having substantially the same binding specificity of a parent antibody; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence of the antibody of the invention, including, but not limited to, the expression systems taught in U.S. Pat. No. 6,815,184 (methods for expression and secretion of biologically active polypeptides from genetically engineered duckweed); WO 2004/057002 (production of glycosylated proteins in bryophyte plant cells by introduction of a glycosyl transferase gene) and WO 2004/024927 (methods of generating extracellular heterologous non-plant protein in moss protoplast); and U.S. Pat. Appl. Nos. 60/365,769, 60/368,047, and WO 2003/078614 (glycoprotein processing in transgenic plants comprising a functional mammalian GnTIII enzyme) (each of which is hereby incorporated by reference in its entirety); or animal cell systems infected with recombinant virus expression vectors (e.g., adenovirus, vaccinia virus) including cell lines engineered to contain multiple copies of the DNA encoding a modified antibody having substantially the same binding specificity of a parent antibody either stably amplified (CHO/dhfr) or unstably amplified in double-minute chromosomes (e.g., murine cell lines). In one embodiment, the vector comprising the polynucleotide(s) encoding the antibody of the invention is polycistronic. In a preferred embodiment, the antibody is a humanized antibody.

In one embodiment, the present invention is directed to an expression vector and/or a host cell which comprise one or more isolated polynucleotides of the present invention. According to one aspect of the invention, the light and heavy chains can be expressed separately, using immunoglobulin light chain and immunoglobulin heavy chains in separate plasmids, or on a single (including but not limited to, a polycistronic) vector. Accordingly, in one aspect of the invention, a polynucleotide encoding a variant heavy chain region of an antibody is provided. In one aspect of the invention, a polynucleotide encoding a light chain region of an antibody is provided. In one aspect of the invention a vector comprising a polynucleotide encoding a variant heavy chain and/or a light chain of an antibody is provided. In a further aspect said vector is polycystronic. One embodiment of the present invention is directed to host cells comprising said polynucleotides or vectors. The present invention is also directed to a method for producing an antibody of the present invention in a host cell comprising (i) culturing the host cell under conditions permitting the expression of said at least one polynucleotide; and (ii) recovering said antibody from the culture medium.

For the methods of this invention, stable expression is generally preferred to transient expression because it typically achieves more reproducible results and also is more amenable to large-scale production. Rather than using expression vectors which contain viral origins of replication, host cells can be transformed with the respective coding nucleic acids controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched media, and then are switched to a selective media. The selectable marker in the recombinant plasmid confers resistance to the selection and allows selection of cells which have stably integrated the plasmid into their chromosomes and grow to form foci which in turn can be cloned and expanded into cell lines.

A number of selection systems may be used, including, but not limited to, the herpes simplex virus thymidine kinase (Wigler et al, Cell 11:223 (1977)), hypoxanthine-guanine phosphoribosyltransferase (Szybalska & Szybalski, Proc.

Natl. Acad. Sd. USA 48:2026 (1962)), and adenine phosphoribosyltransferase (Lowy et al, Cell 22:817 (1980)) genes, which can be employed in tk⁻, hgprt⁻ or aprt⁻ cells, respectively. Also, antimetabolite resistance can be used as the basis of selection for dhfr, which confers resistance to methotrexate (Wigler et al, Natl Acad. Sd. USA 77:3567 (1989); O'Hare et al, Proc. Natl Acad. ScL USA 78: 1527 (1981)); gpt, which confers resistance to mycophenolic acid (Mulligan & Berg, Proc. Natl Acad. ScL USA 78:2072 (1981)); neo, which confers resistance to the aminoglycoside G-418 (Colberre-Garapin et al, J. Mol Biol 150:1 (1981)); and hygro, which confers resistance to hygromycin (Santerre et al, Gene 30:147 (1984) genes. Recently, additional selectable genes have been described, namely trpB, which allows cells to utilize indole in place of tryptophan; hisD, which allows cells to utilize histinol in place of histidine (Hartman & Mulligan, Proc. Natl Acad. ScL USA S5:8047 (1988)); the glutamine synthase system; and ODC (ornithine decarboxylase) which confers resistance to the ornithine decarboxylase inhibitor, 2-(difluoromethyl)-DL-ornithine, DEMO (McConlogue, in: Current Communications in Molecular Biology, Cold Spring Harbor Laboratory ed. (1987)).

Expression of Modified Antibodies Comprising Fc Regions with Altered Glycosylation The therapeutic efficacy of the modified antibodies of the present invention can be further enhanced by producing them in a host cell that has been glycoengineered to have altered expression of at least one glycoprotein-modifying glycosyltransferase as herein disclosed. In one embodiment, the glycoengineered host cell further expresses one or more of the following: a polynucleotide encoding a polypeptide having β(1,4)-N-acetylglucosaminyltransferase III (GnTIII) activity, a polynucleotide encoding a polypeptide having mannosidase II (ManII) activity, or a polynucleotide encoding a polypeptide having GalT activity. In a preferred embodiment, the host cell expresses a polynucleotide encoding a polypeptide having GnTIII activity or ManII activity. In a preferred embodiment, the host cell expresses at least one polynucleotide encoding a polypeptide having GnTIII activity. In another preferred embodiment, the host cell expresses a polynucleotide encoding a polypeptide having GnTIII activity as well as a polynucleotide encoding a polypeptide having ManII activity. In yet another preferred embodiment, the polypeptide having GnTIII activity is a fusion polypeptide further comprising the Golgi localization domain of a Golgi resident polypeptide. In another preferred embodiment, said Golgi localization domain is selected from the localization domain of mannosidase II, the localization domain of β(1,2)-N-acetylglucosaminyltransferase I, the localization of β(1,2)-N-acetylglucosaminyltransferase II, the localization domain of mannosidase I, and the localization of α1-6 core fucosyltransferase. In another preferred embodiment, the expression of the modified antibodies of the present invention in a host cell that expresses a polynucleotide encoding a polypeptide having GnTIII activity results in modified antibodies with increased Fc receptor binding affinity and increased effector function. Accordingly, in one embodiment, the present invention is directed to a host cell comprising (a) an isolated nucleic acid comprising a sequence encoding a polypeptide having GnTIII activity; and (b) an isolated polynucleotide encoding an antibody of the present invention, such as a chimeric, primatized or humanized antibody. In a preferred embodiment, the polypeptide having GnTIII activity is a fusion polypeptide comprising the catalytic domain of GnTIII and the Golgi localization domain is the localization domain of mannosidase II. Methods for generating such fusion polypeptides and using them to produce antibodies with increased effector functions are disclosed in WO 2004065540 and U.S. Pat. Appl. Publ. No. 2004/0241817, each of which is hereby incorporated by reference in its entirety. In another preferred embodiment, the chimeric antibody is a chimeric antibody or a fragment thereof, having the binding specificity of the murine B-Ly1 antibody. In a particularly preferred embodiment, the chimeric antibody comprises a human Fc. In another preferred embodiment, the antibody is primatized or humanized. In one embodiment, one or several polynucleotides encoding an antibody of the present invention may be expressed under the control of a constitutive promoter or, alternately, a regulated expression system. Suitable regulated expression systems include, but are not limited to, a tetracycline-regulated expression system, an ecdysone-inducible expression system, a lac-switch expression system, a glucocorticoid-inducible expression system, a temperature-inducible promoter system, and a metallothionein metal-inducible expression system. If several different nucleic acids encoding an antibody of the present invention are comprised within the host cell system, some of them may be expressed under the control of a constitutive promoter, while others are expressed under the control of a regulated promoter. The maximal expression level is considered to be the highest possible level of stable polypeptide expression that does not have a significant adverse effect on cell growth rate, and will be determined using routine experimentation. Expression levels are determined by methods generally known in the art, including Western blot analysis using an antibody specific for the antibody or an antibody specific for a peptide tag fused to the antibody; and Northern blot analysis. In a further alternative, the polynucleotide may be operatively linked to a reporter gene; the expression levels of a modified antibody having substantially the same binding specificity of a parent antibody are determined by measuring a signal correlated with the expression level of the reporter gene. The reporter gene may be transcribed together with the nucleic acid(s) encoding said fusion polypeptide as a single mRNA molecule; their respective coding sequences may be linked either by an internal ribosome entry site (IRES) or by a cap-independent translation enhancer (CITE). The reporter gene may be translated together with at least one nucleic acid encoding a modified antibody having substantially the same binding specificity of a parent antibody such that a single polypeptide chain is formed. The nucleic acids encoding the antibodies of the present invention may be operatively linked to the reporter gene under the control of a single promoter, such that the nucleic acid encoding the fusion polypeptide and the reporter gene are transcribed into an RNA molecule which is alternatively spliced into two separate messenger RNA (mRNA) molecules; one of the resulting mRNAs is translated into said reporter protein, and the other is translated into said fusion polypeptide.

In one aspect, the present invention is further directed to a method for modifying the glycosylation profile of the modified antibodies comprising at least one amino acid substitution in the VH or CH1 region that are produced by a host cell, comprising expressing in said host cell a nucleic acid encoding a modified antibody of the invention and a nucleic acid encoding a polypeptide with GnTIII activity, or a vector comprising such nucleic acids. Preferably, the modified polypeptide is IgG or a fragment thereof comprise the Fc region. In a particularly preferred embodiment the antibody is a humanized antibody or a fragment thereof. In another embodiment, the host cell is engineered to co-express an antibody of the invention, GnTIII and mannosidase II.

In one aspect, the modified antibodies produced by the host cells of the invention exhibit increased Fc receptor binding affinity and/or increased effector function as a result of the modification. In a particularly preferred embodiment the modified antibody is a humanized antibody or a fragment thereof containing the Fc region. Preferably, the increased Fc receptor binding affinity is increased binding to a Fcγ activating receptor, such as the FcγRIIIa receptor. The increased effector function is preferably an increase in one or more of the following: increased antibody-dependent cell-mediated cytotoxicity, increased antibody-dependent cellular phagocytosis, increased cytokine secretion, increased immune-complex-mediated antigen uptake by antigen-presenting cells, increased Fc-mediated cellular cytotoxicity, increased binding to NK cells, increased binding to macrophages, increased binding to polymorphonuclear cells (PMNs), increased binding to monocytes, increased crosslinking of target-bound antibodies, increased direct signaling inducing apoptosis, increased dendritic cell maturation, and increased T cell priming.

Effector functions can be measured and/or determined by various assays known to those of skill in the art. Various assays for measuring effector functions, including Fc receptor binding affinity and complement dependent cytotoxicity, are described in US Application Publication No. 2004/0241817A1, which is hereby incorporated by reference in its entirety. Cytokine secretion can be measured, for example, using a sandwich ELISA, see, e.g., McRae et al, J. Immunol. 164: 23-28 (2000), or by the methods described in Takahashi et al, British J. Pharmacol. 137: 315-322 (2002), each of which is hereby incorporated by reference in its entirety. Dendritic cell maturation, for example, can be determined using assays as set forth by Kalergis and Ravetch, J. Exp. Med. 195: 1653-59 (2002), which is hereby incorporated by reference in its entirety. Examples of phagocytosis and antigen uptake/presentation assays are provided by Gresham et al, J. Exp. Med. 191: 515-28 (2000); Krauss et al, J. Immunol 153: 1769-77 (1994); and Rafiq et al, J. Clin. Invest. 110: 71-79 (2002), and Hamano et al, J. Immunol. 164: 6113-19 (2000), each of which is hereby incorporated by reference in its entirety. Down regulation of cell-surface receptors can be measured, for example, by methods set forth by Liao et at, Blood 83: 2294-2304 (1994), which is hereby incorporated by reference in its entirety. General methods, protocols and assays, can be found in CELL BIOLOGY: A LABORATORY HANDBOOK, Celis, J. E., ed., (2d ed., 1998), which is hereby incorporated by reference in its entirety. It is within the skill of one in the art to adapt the herein-referenced methods, protocols and assays for use with the present invention.

The present invention is also directed to a method for producing an antibody of the present invention, having modified oligosaccharides in a host cell comprising (a) culturing a host cell engineered to express at least one nucleic acid encoding a polypeptide having GnTIII activity under conditions which permit the production of an antibody according to the present invention, wherein said polypeptide having GnTIII activity is expressed in an amount sufficient to modify the oligosaccharides in the Fc region of said antibody produced by said host cell; and (b) isolating said antibody. In a preferred embodiment, the polypeptide having GnTIII activity is a fusion polypeptide comprising the catalytic domain of GnTIII. In a particularly preferred embodiment, the fusion polypeptide further comprises the Golgi localization domain of a Golgi resident polypeptide. Preferably the Golgi localization domain is the localization domain of mannosidase II or GnTI. Alternatively, the Golgi localization domain is selected from the group consisting of: the localization domain of mannosidase I, the localization domain of GnTII, and the localization domain of a 1-6 core fucosyltransferase. The antibodies produced by the methods of the present invention have increased Fc receptor binding affinity and/or increased effector function. Preferably, the increased effector function is one or more of the following: increased Fc-mediated cellular cytotoxicity (including increased antibody-dependent cell-mediated cytotoxicity), increased antibody-dependent cellular phagocytosis, increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. The increased Fc receptor binding affinity is preferably increased binding to Fc activating receptors such as FcγRIIIa. In a particularly preferred embodiment the antibody is a humanized antibody or a fragment thereof.

In another embodiment, the present invention is directed to a modified antibody having substantially the same binding specificity of a parent antibody produced by the methods of the invention which has an increased proportion of bisected oligosaccharides in the Fc region of said polypeptide. It is contemplated that such an antibody encompasses antibodies and fragments thereof comprising the Fc region. In a preferred embodiment, the antibody is a humanized antibody. In one embodiment, the percentage of bisected oligosaccharides in the Fc region of the antibody is at least 50%, more preferably, at least 60%, at least 70%, at least 80%, or at least 90%, and most preferably at least 90-95% of the total oligosaccharides, in yet another embodiment, the antibody produced by the methods of the invention has an increased proportion of nonfucosylated oligosaccharides in the Fc region as a result of the modification of its oligosaccharides by the methods of the present invention. In one embodiment, the percentage of nonfucosylated oligosaccharides is at least 50%, preferably at least 60% to 70%, most preferably at least 75%. The nonfucosylated oligosaccharides may be of the hybrid or complex type. In a particularly preferred embodiment, the antibody produced by the host cells and methods of the invention has an increased proportion of bisected, nonfucosylated oligosaccharides in the Fc region. The bisected, nonfucosylated oligosaccharides may be either hybrid or complex. Specifically, the methods of the present invention may be used to produce antibodies in which at least 15%, more preferably at least 20%, more preferably at least 25%, more preferably at least 30%, more preferably at least 35% of the oligosaccharides in the Fc region of the antibody are bisected, nonfucosylated. The methods of the present invention may also be used to produce polypeptides in which at least 15%, more preferably at least 20%, more preferably at least 25%, more preferably at least 30%, more preferably at least 35% of the oligosaccharides in the Fc region of the polypeptide are bisected hybrid nonfucosylated.

In another embodiment, the present invention is directed to a modified antibody having substantially the same binding specificity of a parent antibody engineered to have increased effector function and/or increased Fc receptor binding affinity, produced by the methods of the invention. Preferably, the increased effector function is one or more of the following: increased Fc-mediated cellular cytotoxicity (including increased antibody-dependent cell-mediated cytotoxicity), increased antibody-dependent cellular phagocytosis, increased cytokine secretion, increased immune-complex-mediated antigen uptake by antigen-presenting cells, increased binding to NK cells, increased binding to macrophages, increased binding to monocytes, increased binding to polymorphonuclear cells, increased direct signaling inducing apoptosis, increased crosslinking of target-bound antibodies, increased dendritic cell maturation, or increased T cell priming. In a preferred embodiment, the increased Fc receptor binding affinity is increased binding to a Fc activating receptor, most preferably FcγRIIIa. In one embodiment, the modified polypeptide is an antibody, an antibody fragment containing the Fc region, or a fusion protein that includes a region equivalent to the Fc region of an immunoglobulin. In a particularly preferred embodiment, the antibody is a humanized antibody.

Generation of Cell Lines for the Production of Modified Antibodies with Altered Glycosylation Pattern The present invention provides host cell expression systems for the generation of the modified antibodies of the present invention having modified glycosylation patterns. In particular, the present invention provides host cell systems for the generation of glycoforms of the modified antibodies of the present invention having an improved therapeutic value. Therefore, the invention provides host cell expression systems selected or engineered to express a polypeptide having GnTIII activity. In one embodiment, the polypeptide having GnTIII activity is a fusion polypeptide comprising the Golgi localization domain of a heterologous Golgi resident polypeptide. Specifically, such host cell expression systems may be engineered to comprise a recombinant nucleic acid molecule encoding a polypeptide having GnTIII, operatively linked to a constitutive or regulated promoter system.

In one specific embodiment, the present invention provides a host cell that has been engineered to express at least one nucleic acid encoding a fusion polypeptide having GnTIII activity and comprising the Golgi localization domain of a heterologous Golgi resident polypeptide. In one aspect, the host cell is engineered with a nucleic acid molecule comprising at least one gene encoding a fusion polypeptide having GnTIII activity and comprising the Golgi localization domain of a heterologous Golgi resident polypeptide.

Generally, any type of cultured cell line, including the cell lines discussed herein, can be used as a background to engineer the host cell lines of the present invention. In a preferred embodiment, CHO cells, BHK cells, NS0 cells, SP2/0 cells, YO myeloma cells, P3X63 mouse myeloma cells, PER cells, PER.C6 cells or hybridoma cells, other mammalian cells, yeast cells, insect cells, or plant cells are used as the background cell line to generate the engineered host cells of the invention.

The invention is contemplated to encompass any engineered host cells expressing a polypeptide having GnTIII activity, including a fusion polypeptide that comprises the Golgi localization domain of a heterologous Golgi resident polypeptide as defined herein.

One or several nucleic acids encoding a polypeptide having GnTIII activity may be expressed under the control of a constitutive promoter or, alternately, a regulated expression system. Such systems are well known in the art, and include the systems discussed herein. If several different nucleic acids encoding fusion polypeptides having GnTIII activity and comprising the Golgi localization domain of a heterologous Golgi resident polypeptide are comprised within the host cell system, some of them may be expressed under the control of a constitutive promoter, while others are expressed under the control of a regulated promoter. Expression levels of the fusion polypeptides having GnTIII activity are determined by methods generally known in the art, including Western blot analysis, Northern blot analysis, reporter gene expression analysis or measurement of GnTIII activity. Alternatively, a lectin may be employed which binds to biosynthetic products of the GnTIII, for example, E4-PHA lectin. Alternatively, a functional assay which measures the increased Fc receptor binding or increased effector function mediated by antibodies produced by the cells engineered with the nucleic acid encoding a polypeptide with GnTIII activity may be used.

Identification of Transfectants or Transformants that Express the Protein Having a Modified Glycosylation Pattern The host cells which contain the coding sequence of a modified antibody of the present invention and which express the biologically active gene products may be identified by at least four general approaches; (a) DNA-DNA or DNA-RNA hybridization; (b) the presence or absence of "marker" gene functions; (c) assessing the level of transcription as measured by the expression of the respective mRNA transcripts in the host cell; and (d) detection of the gene product as measured by immunoassay or by its biological activity.

In the first approach, the presence of the coding sequence of a modified antibody of the present invention and the coding sequence of the polypeptide having GnTIII activity can be detected by DNA-DNA or DNA-RNA hybridization using probes comprising nucleotide sequences that are homologous to the respective coding sequences, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the coding sequence of the modified antibody of the invention, or a fragment thereof, and the coding sequence of the polypeptide having GnTIII activity are inserted within a marker gene sequence of the vector, recombinants containing the respective coding sequences can be identified by the absence of the marker gene function. Alternatively, a marker gene can be placed in tandem with the coding sequences under the control of the same or different promoter used to control the expression of the coding sequences. Expression of the marker in response to induction or selection indicates expression of the coding sequence of the modified antibody of the invention and the coding sequence of the polypeptide having GnTIII activity.

In the third approach, transcriptional activity for the coding region of the modified antibody of the invention, or a fragment thereof, and the coding sequence of the polypeptide having GnTIII activity can be assessed by hybridization assays. For example, RNA can be isolated and analyzed by Northern blot using a probe homologous to the coding sequences of the modified antibody of the invention, or a fragment thereof, and the coding sequence of the polypeptide having GnTIII activity or particular portions thereof. Alternatively, total nucleic acids of the host cell may be extracted and assayed for hybridization to such probes.

In the fourth approach, the expression of the protein products can be assessed immunologically, for example by Western blots, immunoassays such as radioimmuno-precipitation, enzyme-linked immunoassays and the like. The ultimate test of the success of the expression system, however, involves the detection of the biologically active gene products.

Therapeutic Applications of Modified Antibodies According to the Methods of the Invention In the broadest sense, the modified antibodies of the present invention can be used to target cells in vivo or in vitro that express a target antigen, in particular, where said target antigen is expressed on the cell surface. The cells expressing a target antigen can be targeted for diagnostic or therapeutic purposes. In one aspect, the modified antibodies of the present invention can be used to alter cell signaling activity in cells expressing a target antigen. In another aspect, the modified antibodies of the present invention can be used to alter the cross-linking and/or oligomerization of one or more target antigens. Target antigens for the modified antibodies of the present invention can be cell surface receptors including, but not limited to CD20, CD21, CD22, CD19, CD47, CD99, CD2, CD45, Her1 (EGFR), Her2/neu, Her3, Her4, TRAIL receptors (e.g., TRAILR1, TRAILR2), TNFR, FGF receptors (e.g., FGFR1), IGF receptors, PDGF receptors, VEGF receptors, and other cell-surface associated receptors. In a particular embodiment, the target antigen is CD20. The modified antibodies of the invention also act to arrest the cell cycle, cause direct cell death of the target cells, inhibit angiogenesis and/or cause differentiation of target cells.

In another aspect, the invention is directed to a method for treating a disease that is treatable by altered cell signaling activity of a target antigen and/or by altered ability to mediate cross-linking of one or more target antigens comprising administering a therapeutically effective amount of a modified antibody of the present invention to a subject in need thereof. In a specific embodiment the modified antibody is humanized. Examples of diseases for which the modified antibodies can be administered include, but are not limited to, cell proliferation diseases or disorders, autoimmune diseases or disorders, and diseases or disorders related to bacterial or viral infection.

In one embodiment, the invention is directed to a method for treating a disease selected from the group consisting of proliferative disorder and autoimmune disease comprising administering to an individual an effective amount of the antibody according to the present invention. In a further aspect, said method comprises administering to a subject a pharmaceutically effective amount of a composition containing at least one of the modified antibodies of the invention (conjugated, including but not limited to an immunotoxin, or unconjugated). In one embodiment, said proliferative disorder include, but is not limited to, neoplasms, cancers, malignancies and/or tumors located in the abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Particular neoplasms, cancers, malignancies, and/or tumors that can be treated with the antibodies of the invention include, but are not limited to, epidermal and squamous cell carcinomas, gliomas, pancreatic cancer, ovarian cancer, prostate cancer, breast cancer, bladder cancer, head and neck cancer, renal cell carcinomas, colon cancer, colorectal cancer, lung cancer, brain tumor, malignant melanoma, leukemia, lymphomas, T cell lymphomas, multiple myeloma, gastric cancer, cervical cancer, endometrial carcinoma, esophageal cancer, liver cancer, cutaneous cancer, urinary tract carcinoma, choriocarcinoma, pharyngeal cancer, laryngeal cancer, thecomatosis, androblastoma, endometrium hyperplasy, endometriosis, embryoma, fibrosarcoma, Kaposi's sarcoma, hemangioma, cavernous hemangioma, angioblastoma, retinoblastoma, astrocytoma, neurofibroma, oligodendroglioma, medulloblastoma, ganglioneuroblastoma, glioma, rhabdomyosarcoma, hamartoblastoma, osteogenic sarcoma, leiomyosarcoma, thyroid sarcoma, Ewing's sarcoma, and Wilms tumor. In a preferred embodiment, said proliferative disorder is a CD20 expressing cancer. In another preferred embodiment, said cancer is selected from the group consisting of lymphoma and lymphocytic leukemia. Such lymphomas and lymphocytic leukemias include, but are not limited to, follicular lymphomas, Small Non-Cleaved Cell Lymphomas/Burkitt's lymphoma (including endemic Burkitt's lymphoma, sporadic Burkitt's lymphoma and Non-Burkitt's lymphoma), marginal zone lymphomas (including extranodal marginal zone B cell lymphoma (Mucosa-associated lymphatic tissue lymphomas, MALT), nodal marginal zone B cell lymphoma and splenic marginal zone lymphoma), Mantle cell lymphoma (MCL), Large Cell Lymphoma (including diffuse large B-cell lymphoma (DLBCL), Diffuse Mixed Cell Lymphoma, Immunoblastic Lymphoma, Primary Mediastinal B-Cell Lymphoma, Angiocentric Lymphoma-Pulmonary B-Cell Lymphoma), hairy cell leukemia, lymphocytic lymphoma, Waldenstrom's macroglobulinemia, acute lymphocytic leukemia (ALL), chronic lymphocytic leukemia (CLL)/small lymphocytic lymphoma (SLL), B-cell prolymphocytic leukemia, plasma cell neoplasms, plasma cell myeloma, multiple myeloma, plasmacytoma, Hodgkin's disease. In a preferred embodiment, said CD20 expressing cancer is selected from the group consisting of Non-Hodgkin's lymphomas (NHL), follicular lymphomas, diffuse large B-cell lymphoma (DLBCL) and chronic lymphocytic leukemia (CLL).

In a further aspect, the invention is directed to an improved method for treating B-cell proliferative disorders including B-cell lymphoma, based on B-cell depletion comprising administering a therapeutically effective amount of an antibody of the present invention to a human subject in need thereof. In a preferred embodiment, the antibody is a glycoengineered anti-CD20 antibody with a binding specificity substantially the same as that of the murine B-Ly1 antibody. In another preferred embodiment the antibody is humanized. In another preferred embodiment the antibody comprises a variant heavy chain region comprising at least one amino acid substitution relative to the parent non-substituted heavy chain region, wherein the heavy chain region of the parent non-substituted antibody comprises at least one of the amino acid residues selected from the group consisting of Val11, Leu11 and Pro151, wherein said substitution is at one of said amino acid residues selected from the group consisting of Val11, Leu11 and Pro151, and wherein direct cell death induced by the antibody comprising the variant heavy chain region is altered compared to direct cell death induced by the antibody comprising the parent non-substituted heavy chain region. In this aspect of the invention, the antibodies of the invention are used to deplete the blood of normal B-cells for an extended period.

The subject invention further provides methods for inhibiting the growth of human tumor cells, treating a tumor in a subject, and treating a proliferative type disease in a subject. These methods comprise administering to the subject an effective amount of the composition of the invention.

Other cell proliferation disorders can also be treated with the modified antibodies of the present invention. As encompassed by the present invention, said cell proliferation disorders include, but are not limited to hypergammaglobulinemia, lymphoproliferative disorders, paraproteinemias, purpura, sarcoidosis, Sezary Syndrome, Waldenstrom's Macroglobulinemia, Gaucher's Disease, histiocytosis, and any other cell proliferation disease, besides neoplasia, located in an organ system listed herein.

In another embodiment, the invention is directed to a method for treating an autoimmune disease. In one embodiment, said autoimmune disease include, but is not limited to, immune-mediated thrombocytopenias, such as acute idiopathic thrombocytopenic purpurea and chronic idiopathic thrombocytopenic purpurea, dermatomyositis, Sydenham's chorea, lupus nephritis, rheumatic fever, polyglandular syndromes, Henoch-Schonlein purpura, poststreptococcal nephritis, erythema nodosum, Takayasu's arteritis, Addison's disease, erythema multiforme, polyarteritis nodosa, ankylosing spondylitis, Goodpasture's syndrome, thromboangiitis ubiterans, primary biliary cirrhosis, Hashimoto's thyroiditis, thyrotoxicosis, chronic active hepatitis, polymyositis/dermatomyositis, polychondritis, pamphigus vulgaris, Wegener's granulomatosis, membranous nephropathy, amyotrophic lateral sclerosis, tabes dorsalis, polymyaglia, pernicious anemia, rapidly progressive glomerulonephritis and fibrosing alveolitis, inflammatory responses such as inflammatory skin diseases including psoriasis and dermatitis (e.g., atopic dermatitis), systemic scleroderma and sclerosis, responses associated with inflammatory bowel disease (such as Crohn's disease and ulcerative colitis), respiratory distress syndrome (including adult respiratory distress syndrome, ARDS), dermatitis, meningitis, encephalitis, uveitis, colitis, glomerulonephritis, allergic conditions such as eczema and asthma and other conditions involving infiltration of T cells and chronic inflammatory responses, atherosclerosis, leukocyte adhesion deficiency, rheumatoid arthritis, systemic lupus erythematosus (SLE), diabetes mellitus (e.g., Type 1 diabetes mellitus or insulin dependent diabetes mellitus), multiple sclerosis, Reynaud's syndrome, autoimmune thyroiditis, allergic encephalomyelitis, Sjogren's syndrome, juvenile onset diabetes, and immune responses associated with acute and delayed hypersensitivity mediated by cytokines and T-lymphocytes typically found in tuberculosis, sarcoidosis, polymyositis, granulomatosis and vasculitis, pernicious anemia (Addison's disease), diseases involving leukocyte diapedesis, central nervous system (CNS) inflammatory disorder, multiple organ injury syndrome, hemolytic anemia (including, but not limited to cryoglobinemia or Coombs positive anemia), myasthenia gravis, antigen-antibody complex mediated diseases, anti-glomerular basement membrane disease, antiphospholipid syndrome, allergic neuritis, Graves' disease, Lambert-Eaton myasthenic syndrome, pemphigoid bullous, pemphigus, autoimmune polyendocrinopathies, Reiter's disease, stiff-man syndrome, Behcet disease, giant cell arteritis, immune complex nephritis, IgA nephropathy, IgM polyneuropathies, immune thrombocytopenic purpura (ITP) or autoimmune thrombocytopenia. In a preferred embodiment, said autoimmune disease is selected from the group consisting of rheumatoid arthritis, lupus, multiple sclerosis, Sjogren's syndrome and transplant rejection.

In a further aspect, the invention is directed to an improved method for treating an autoimmune disease as defined herein, based on B-cell depletion comprising administering a therapeutically effective amount of an antibody of the present invention to a human subject in need thereof. In a preferred embodiment, the antibody is a glycoengineered anti-CD20 antibody with a binding specificity substantially the same as that of the murine B-Ly1 antibody. In another preferred embodiment the antibody is humanized. In another preferred embodiment the antibody comprises a variant heavy chain region comprising at least one amino acid substitution relative to the parent non-substituted heavy chain region, wherein the heavy chain region of the parent non-substituted antibody comprises at least one of the amino acid residues selected from the group consisting of Val11, Leu11 and Pro151, wherein said substitution is at one of said amino acid residues selected from the group consisting of Val11, Leu11 and Pro151, and wherein direct cell death induced by the antibody comprising the variant heavy chain region is altered compared to direct cell death induced by the antibody comprising the parent non-substituted heavy chain region. In this aspect of the invention, the antibodies of the invention are used to deplete the blood of normal B-cells for an extended period.

The modified antibodies of the present invention can be used alone or in combination with other treatments or therapeutic agents to treat disorders that are treatable by increasing or decreasing cell signaling activity and/or cross-linking of one or more target antigens. In one embodiment, modified antibodies of the present can be used alone to target and kill tumor cells in vivo. The modified antibodies can also be used in conjunction with an appropriate therapeutic agent to treat human carcinoma. For example, the modified antibodies can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma. In particular embodiments, the conjugates of the modified antibodies of this invention include (1) immunotoxins (conjugates of the modified antibody and a cytotoxic moiety) and (2) labeled (e.g., radiolabeled, enzyme-labeled, or fluorochrome-labeled) modified antibodies in which the label provides a means for identifying immune complexes that include the labeled antibody. The modified antibodies can also be used to induce lysis through the natural complement process, and to interact with antibody dependent cytotoxic cells normally present. The cytotoxic moiety of the immunotoxin may be a cytotoxic drug or an enzymatically active toxin of bacterial or plant origin, or an enzymatically active fragment ("A chain") of such a toxin. Enzymatically active toxins and fragments thereof used are diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin. In another embodiment, the modified antibodies are conjugated to small molecule anticancer drugs. Conjugates of the modified antibody and such cytotoxic moieties are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of the modified antibodies. Additional appropriate toxins are known in the art, as evidenced in e.g., published U.S. Patent Application No. 2002/0128448, incorporated herein by reference in its entirety.

In one embodiment, the antigen binding molecule of the present invention is conjugated to an additional moiety, such as a radiolabel or a toxin. Such conjugated modified antibodies can be produced by numerous methods that are well known in the art.

A variety of radionuclides are applicable to the present invention and those skilled in the art are credited with the ability to readily determine which radionuclide is most appropriate under a variety of circumstances. For example, $^{131}$iodine is a well known radionuclide used for targeted immunotherapy. However, the clinical usefulness of $^{131}$iodine can be limited by several factors including: eight-day physical half-life; dehalogenation of iodinated antibody both in the blood and at tumor sites; and emission characteristics (eg, large gamma component) which can be suboptimal for localized dose deposition in tumor. With the advent of superior chelating agents, the opportunity for attaching metal chelating groups to proteins has increased the opportunities to utilize other radionuclides such as $^{111}$indium and $^{90}$yttrium. $^{90}$Yttrium provides several benefits for utilization in radioimmunotherapeutic applications: the 64 hour half-life of $^{90}$yttrium is long enough to allow antibody accumulation by tumor and, unlike eg, $^{131}$iodine, $^{90}$yttrium is a pure beta emitter of high energy with no accompanying gamma irradiation in its decay, with a range in tissue of 100 to 1000 cell diameters. Furthermore, the minimal amount of penetrating radiation allows for outpatient administration of $^{90}$yttrium-labeled antibodies. Additionally, internalization of labeled antibody is not required for cell killing, and the local emission of ionizing radiation should be lethal for adjacent tumor cells lacking the target antigen.

Effective single treatment dosages (i.e., therapeutically effective amounts) of $^{90}$yttrium labeled modified antibodies of the present invention range from between about 5 and about 75 mCi, more preferably between about 10 and about 40 mCi. Effective single treatment non-marrow ablative dosages of $^{13}$iodine labeled antibodies of the present invention range from between about 5 and about 70 mCi, more preferably between about 5 and about 40 mCi. Effective single treatment ablative dosages (i.e., may require autologous bone marrow transplantation) of $^{131}$iodine labeled antibodies of the present invention range from between about 30 and about 600 mCi, more preferably between about 50 and less than about 500 mCi. In conjunction with a chimeric antibody according to the present invention, owing to the longer circulating half life vis-a-vis murine antibodies, an effective single treatment non-marrow ablative dosages of $^{131}$iodine labeled chimeric antibodies range from between about 5 and about 40 mCi, more preferably less than about 30 mCi. Imaging criteria for the $^{111}$indium label, are typically less than about 5 mCi.

With respect to radiolabeled antibodies of the present invention, therapy therewith can also occur using a single therapy treatment or using multiple treatments. Because of the radionuclide component, it is preferred that prior to treatment, peripheral stem cells ("PSC") or bone marrow ("BM") be "harvested" for patients experiencing potentially fatal bone marrow toxicity resulting from radiation. BM and/or PSC are harvested using standard techniques, and then purged and frozen for possible reinfusion. Additionally, it is most preferred that prior to treatment a diagnostic dosimetry study using a diagnostic labeled antibody (including but not limited to using $^{111}$indium) be conducted on the patient, a purpose of which is to ensure that the therapeutically labeled antibody (eg, using $^{90}$yttrium) will not become unnecessarily "concentrated" in any normal organ or tissue.

In one embodiment, a chimeric, glycoengineered modified antibody of the present invention, is conjugated to ricin A chain. Most advantageously, the ricin A chain is deglycosylated and produced through recombinant means. An advantageous method of making the ricin immunotoxin is described in Vitetta et al., Science 238, 1098 (1987), hereby incorporated by reference in its entirety.

When used to kill human cancer cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques to determine the presence or degree of cancer.

As discussed herein, a cytotoxic radiopharmaceutical for treating cancer may be made by conjugating a radioactive isotope (e.g., I, Y, Pr) to a chimeric, glycoengineered and/or modified antibody of the present invention. The term "cytotoxic moiety" as used herein is intended to include such isotopes.

In another embodiment, liposomes are filled with a cytotoxic drug and the liposomes are coated with the antibodies of the present invention. Because many of the target molecules for the modified antibodies of the present invention are expressed on the cell surface (e.g., there are many CD20 molecules on the surface of the malignant B-cell), this method permits delivery of large amounts of drug to the correct cell type.

Techniques for conjugating such therapeutic agents to antibodies are well known (see, e.g., Arnon et al., "Monoclonal Antibodies for Immunotargeting of Drugs in Cancer Therapy", in Monoclonal Antibodies and Cancer Therapy, Reisfeld et al. (eds.), pp. 243-56 (Alan R. Liss, Inc. 1985); Hellstrom et at, "Antibodies For Drug Delivery", in Controlled Drug Delivery (2nd Ed.), Robinson et al. (eds.), pp. 623-53 (Marcel Defcker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982) (each of which is hereby incorporated by reference in its entirety).

Still other therapeutic applications for the antibodies of the invention include conjugation or linkage, including but not limited to conjugation by recombinant DNA techniques, to an enzyme capable of converting a prodrug into a cytotoxic drug and the use of that antibody-enzyme conjugate in combination with the prodrug to convert the prodrug to a cytotoxic agent at the tumor site (see, e.g., Senter et al., "Anti-Tumor Effects of Antibody-alkaline Phosphatase", Proc. Natl. Acad. ScL USA 55:4842-46 (1988); "Enhancement of the in vitro and in vivo Antitumor Activities of Phosphorylated Mitocycin C and Etoposide Derivatives by Monoclonal Antibody-Alkaline Phosphatase Conjugates", Cancer Research 49:5789-5792 (1989); and Senter, "Activation of Prodrugs by Antibody-Enzyme Conjugates: A New Approach to Cancer Therapy," FASEB J. 4:188-193 (1990)).

Still another therapeutic use for the antibodies of the invention involves use, either unconjugated, in the presence of complement, or as part of an antibody-drug or antibody-toxin conjugate, to remove tumor cells from the bone marrow of cancer patients. According to this approach, autologous bone marrow may be purged ex vivo by treatment with the antibody and the marrow infused back into the patient (see, e.g., Ramsay et al., "Bone Marrow Purging Using Monoclonal Antibodies", J. Clin. Immunol, 8(2):81-88 (1988)).

Furthermore, it is contemplated that the invention comprises a single-chain immunotoxin comprising antigen binding domains that allow substantially the same specificity of binding as a parent antibody (including but not limited to, polypeptides comprising the CDRs of the parent antibody) and further comprising a toxin polypeptide. The single-chain immunotoxins of the invention may be used to treat human carcinoma in vivo.

Similarly, a fusion protein comprising at least the antigen-binding region of an antibody of the invention joined to at least a functionally active portion of a second protein having anti-tumor activity, including but not limited to, a lymphokine or oncostatin, can be used to treat human carcinoma in vivo.

Accordingly, the present invention provides a method for selectively killing tumor cells expressing cell surface receptors including, but not limited to CD20, Her1 (EGFR), Her2/neu, Her3, Her4, TRAIL receptors (e.g., TRAILR1, TRAILR2), TNFR, FGF receptors (e.g., FGFR1), IGF receptors, PDGF receptors, VEGF receptors, and other cell-surface associated receptors. This method comprises reacting the modified antibody of the invention (conjugated, e.g., as an immunotoxin, or unconjugated) with said tumor cells. These tumor cells may be from a human carcinoma.

In a further aspect, the invention relates to an antibody according to the present invention for use as a medicament. In one embodiment, the invention relates to an antibody according to the present invention for use in treating a disease selected from the group consisting of proliferative disorder and autoimmune disease. According to one aspect of the invention said proliferative disorder is selected from the group consisting of B-cell lymphoma, lung cancer, non-small cell lung (NSCL) cancer, bronchioalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the herein cancers, or a combination of one or more of the herein cancers. The precancerous condition or lesion includes, for example, the group consisting of oral leukoplakia, actinic keratosis (solar keratosis), precancerous polyps of the colon or rectum, gastric epithelial dysplasia, adenomatous dysplasia, hereditary nonpolyposis colon cancer syndrome (HNPCC), Barrett's esophagus, bladder dysplasia, and precancerous cervical conditions. Preferably, the cancer is selected from the group consisting of B-cell lymphoma, breast cancer, bladder cancer, head and neck cancer, skin cancer, pancreatic cancer, lung cancer, ovarian cancer, colon cancer, prostate cancer, kidney cancer, and brain cancer. In a preferred embodiment, said proliferative disorder is a CD20 expressing cancer. In another preferred embodiment, said cancer is selected from the group consisting of lymphoma and lymphocytic leukemia.

According to another aspect of the invention said autoimmune disease is selected from the group consisting of immune-mediated thrombocytopenias, such as acute idiopathic thrombocytopenic purpurea and chronic idiopathic thrombocytopenic purpurea, dermatomyositis, Sydenham's chorea, lupus nephritis, rheumatic fever, polyglandular syndromes, Henoch-Schonlein purpura, poststreptococcal nephritis, erythema nodosum, Takayasu's arteritis, Addison's disease, erythema multiforme, polyarteritis nodosa, ankylosing spondylitis, Goodpasture's syndrome, thromboangiitis ubiterans, primary biliary cirrhosis, Hashimoto's thyroiditis, thyrotoxicosis, chronic active hepatitis, polymyositis/dermatomyositis, polychondritis, pamphigus vulgaris, Wegener's granulomatosis, membranous nephropathy, amyotrophic lateral sclerosis, tabes dorsalis, polymyaglia, pernicious anemia, rapidly progressive glomerulonephritis and fibrosing alveolitis, inflammatory responses such as inflammatory skin diseases including psoriasis and dermatitis (e.g., atopic dermatitis), systemic scleroderma and sclerosis, responses associated with inflammatory bowel disease (such as Crohn's disease and ulcerative colitis), respiratory distress syndrome (including adult respiratory distress syndrome, ARDS), dermatitis, meningitis, encephalitis, uveitis, colitis, glomerulonephritis, allergic conditions such as eczema and asthma and other conditions involving infiltration of T cells and chronic inflammatory responses, atherosclerosis, leukocyte adhesion deficiency, rheumatoid arthritis, systemic lupus erythematosus (SLE), diabetes mellitus (e.g., Type 1 diabetes mellitus or insulin dependent diabetes mellitus), multiple sclerosis, Reynaud's syndrome, autoimmune thyroiditis, allergic encephalomyelitis, Sjogren's syndrome, juvenile onset diabetes, and immune responses associated with acute and delayed hypersensitivity mediated by cytokines and T-lymphocytes typically found in tuberculosis, sarcoidosis, polymyositis, granulomatosis and vasculitis, pernicious anemia (Addison's disease), diseases involving leukocyte diapedesis, central nervous system (CNS) inflammatory disorder, multiple organ injury syndrome, hemolytic anemia (including, but not limited to cryoglobinemia or Coombs positive anemia), myasthenia gravis, antigen-antibody complex mediated diseases, anti-glomerular basement membrane disease, antiphospholipid syndrome, allergic neuritis, Graves' disease, Lambert-Eaton myasthenic syndrome, pemphigoid bullous, pemphigus, autoimmune polyendocrinopathies, Reiter's disease, stiff-man syndrome, Behcet disease, giant cell arteritis, immune complex nephritis, IgA nephropathy, IgM polyneuropathies, immune thrombocytopenic purpura (ITP) or autoimmune thrombocytopenia. In a preferred embodiment, said autoimmune disease is selected from the group consisting of rheumatoid arthritis, lupus, multiple sclerosis, Sjögren's syndrome and transplant rejection.

Yet another embodiment is the use of the antibody according to the present invention for the manufacture of a medicament for the treatment or prophylaxis of cancer or for the treatment or prophylaxis of a precancerous condition or lesion. Cancer and precancerous condition or lesions are defined as herein. In one embodiment, said cancer is a CD20 expressing cancer. In a specific embodiment said cancer is a lymphoma or lymphocytic leukemia. In another specific embodiment said cancer is selected from the group consisting of follicular lymphomas, Small Non-Cleaved Cell Lymphomas/Burkitt's lymphoma (including endemic Burkitt's lymphoma, sporadic Burkitt's lymphoma and Non-Burkitt's lymphoma), marginal zone lymphomas (including extranodal marginal zone B cell lymphoma (Mucosa-associated lymphatic tissue lymphomas, MALT), nodal marginal zone B cell lymphoma and splenic marginal zone lymphoma), Mantle cell lymphoma (MCL), Large Cell Lymphoma (including diffuse large B-cell lymphoma (DLBCL), Diffuse Mixed Cell Lymphoma, Immunoblastic Lymphoma, Primary Mediastinal B-Cell Lymphoma, Angiocentric Lymphoma-Pulmonary B-Cell Lymphoma), hairy cell leukemia, lymphocytic lymphoma, Waldenstrom's macroglobulinemia, acute lymphocytic leukemia (ALL), chronic lymphocytic leukemia (CLL)/small lymphocytic lymphoma (SLL), B-cell prolymphocytic leukemia, plasma cell neoplasms, plasma cell myeloma, multiple myeloma, plasmacytoma, Hodgkin's disease. In a preferred embodiment, said cancer is selected from the group consisting of Non-Hodgkin's lymphomas (NHL), follicular lymphomas, diffuse large B-cell lymphoma (DLBCL) and chronic lymphocytic leukemia (CLL).

The present invention encompasses pharmaceutical compositions, combinations, uses, and methods for treating human carcinomas. The invention includes pharmaceutical compositions for use in the treatment of human carcinomas comprising a pharmaceutically effective amount of an antibody of the present invention and a pharmaceutically acceptable carrier.

The antibody compositions of the invention can be administered using conventional modes of administration including, but not limited to, intravenous, intraperitoneal, oral, intralymphatic or administration directly into the tumor. Intravenous administration is preferred.

The present invention is further directed to pharmaceutical compositions comprising the modified antibodies of the present invention and a pharmaceutically acceptable carrier. In one aspect of the invention, therapeutic formulations containing the antibodies of the invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (Halozyme, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Lyophilized formulations adapted for subcutaneous administration are described in WO 97/04801. Such lyophilized formulations may be reconstituted with a suitable diluent to a high protein concentration and the reconstituted formulation may be administered subcutaneously to the individual to be treated herein.

The formulation herein may also contain more than one active compound as necessary for the particular indication being treated, preferably those with complementary activities that do not adversely affect each other. For example, it may be desirable to further provide a cytotoxic agent, chemotherapeutic agent, cytokine or immunosuppressive agent (e.g. one which acts on T cells, such as cyclosporin or an antibody that binds T cells, e.g., one which binds LFA-1). The effective amount of such other agents depends on the amount of antagonist present in the formulation, the type of disease or disorder or treatment, and other factors discussed herein. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antagonist, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

The compositions of the invention may be in a variety of dosage forms which include, but are not limited to, liquid solutions or suspension, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

The most effective mode of administration and dosage regimen for the pharmaceutical compositions of this invention depends upon the severity and course of the disease, the patient's health and response to treatment and the judgment of the treating physician. Accordingly, the dosages of the compositions should be titrated to the individual patient. Nevertheless, an effective dose of the compositions of this invention will generally be in the range of from about 0.01 to about 2000 mg/kg.

The dosages of the present invention may, in some cases, be determined by the use of predictive biomarkers. Predictive biomarkers are molecular markers that are used to determine (i.e., observe and/or quantitate) a pattern of expression and/or activation of tumor related genes or proteins, or cellular components of a tumor-related signaling pathway. Elucidating the biological effects of targeted therapies in tumor tissue and correlating these effects with clinical response helps identify the predominant growth and survival pathways operative in tumors, thereby establishing a profile of likely responders and conversely providing a rationale for designing strategies to overcoming resistance to therapy. For example, where the modified antibody is an antibody specific for EGFR, biomarkers for anti-EGFR therapy may comprise one or more molecules that are in the EGFR downstream signaling pathway leading to a cell proliferation disorder including, but not limited to, Akt, RAS, RAF, MAPK, ERK1, ERK2, PKC, STAT3, STATS (Mitchell, Nature Biotech. 22: 363-364 (2004); Becker, Nature Biotech 22: 15-18 (2004); Tsao and Herbst, Signal 4: 4-9 (2003)). Biomarkers for anti-EGFR therapy may also comprise growth factor receptors such as EGFR, ErbB-2 (HER2/neu), and ErbB-3 (HER3), and may be positive or negative predictors of patient response to anti-EGFR therapy. For example, the growth factor receptor ErbB-3 (HER3) was determined to be a negative predictive biomarker for the anti-EGFR antibody ABX-EGF (U.S. Pat. Appl. Pub. No. 2004/0132097 A1).

Predictive biomarkers may be measured by cellular assays that are well known in the art including, but not limited to immunohistochemistry, flow cytometry, immunofluorescence, capture-and-detection assays, and reversed phase assays, and/or assays set forth in U.S. Pat. Appl. Pub. No. 2004/0132097 A1, the entire contents of which is hereby incorporated by reference in its entirety. Predictive biomarkers of anti-EGFR therapy, themselves, can be identified according to the techniques set forth in U.S. Pat. Appl. Pub. No. 2003/0190689 A1, the entire contents of which is hereby incorporated by reference in its entirety.

Thus, in one aspect, the present invention provides for a method for treating a disorder that is related to altered or dysregulated cell signaling by a target antigen and/or altered ability to mediate cross-linking and/or oligomerization of one or more target antigens comprising predicting a response to therapy with a modified antibody in a human subject in need of treatment by assaying a sample from the human subject prior to therapy with one or a plurality of reagents that detect expression and/or activation of predictive biomarkers for a disorder that is related to altered or dysregulated cell signaling by a target antigen and/or altered ability to mediate cross-linking and/or oligomerization of one or more target antigens (such as cancer); determining a pattern of expression and/or activation of one or more of the predictive biomarkers, wherein the pattern predicts the human subject's response to the modified antibody therapy; and administering to a human subject who is predicted to respond positively to modified antibody treatment a therapeutically effective amount of a composition comprising a modified antibody of the present invention. As used herein, a human subject who is predicted to respond positively to modified antibody treatment is one for whom the modified antibody will have a measurable effect on the disease or disorder that is related to altered or dysregulated cell signaling by a target antigen and/or altered ability to mediate cross-linking and/or oligomerization of one or more target antigens (e.g., tumor regression/shrinkage) and for whom the benefits of modified antibody therapy are not outweighed by adverse effects (e.g., toxicity).

As used herein, a sample means any biological sample from an organism, particularly a human, comprising one or more cells, including single cells of any origin, tissue or biopsy samples which has been removed from organs such as breast, lung, gastrointestinal tract, skin, cervix, ovary, prostate, kidney, brain, head and neck, or any other organ or tissue of the body, and other body samples including, but not limited to, smears, sputum, secretions, cerebrospinal fluid, bile, blood, lymph fluid, urine and feces.

The composition comprising a modified antibody of the present invention will be formulated, dosed, and administered in a fashion consistent with good medical practice. Factors for consideration in this context include the particular disease or disorder being treated, the particular mammal being treated, the clinic condition of the individual patient, the cause of the disease or disorder, the site of delivery of the agent, the method of administration, the scheduling of administration, and other factors known to medical practitioners. The therapeutically effective amount of the antagonist to be administered will be governed by such considerations.

In a preferred embodiment, the antibody modified according to the present invention is a humanized antibody. Suitable dosages for such an unconjugated antibody are, for example, in the range from about 20 mg/m$^2$ to about 1000 mg/m$^2$. In one embodiment, the dosage of the antibody modified according to the present invention is equal to the dosage presently recommended for the non-substituted parent antibody. In one embodiment, the dosage of the antibody modified according to the present invention differs from the dosage presently recommended for the non-substituted parent antibody. In one embodiment, the dosage of the antibody modified according to the present invention is lower compared to the dosage presently recommended for the non-substituted parent antibody. In one embodiment, the dosage of the antibody modified according to the present invention is higher compared to the dosage presently recommended for the non-substituted parent antibody. In one embodiment, antibodies modified according to the present invention are administer to the patient in one or more doses of substantially less than 375 mg/m$^2$ of the antibody, including but not limited to, where the dose is in the range from about 20 mg/m$^2$ to about 250 mg/m$^2$, or from about 50 mg/m$^2$ to about 200 mg/m$^2$. In another embodiment, the modified antibodies are used in a therapeutically effective amount from about 375 mg/m$^2$ to about 1000 mg/m$^2$.

According to the invention one or more initial dose(s) of the antibody followed by one or more subsequent dose(s) are administered, wherein the mg/m$^2$ dose of the antibody in the subsequent dose(s) exceeds the mg/m$^2$ dose of the antibody in the initial dose(s). For example, the initial dose may be in the range from about 20 mg/m$^2$ to about 250 mg/m$^2$ and the subsequent dose may be in the range from about 250 mg/m$^2$ to about 1000 mg/m$^2$.

As noted herein, however, these suggested amounts of modified antibody are subject to a great deal of therapeutic discretion. The key factor in selecting an appropriate dose and scheduling is the result obtained, as indicated herein. For example, relatively higher doses may be needed initially for the treatment of ongoing and acute diseases. To obtain the most efficacious results, depending on the disease or disorder, the antagonist is administered as close to the first sign, diagnosis, appearance, or occurrence of the disease or disorder as possible or during remissions of the disease or disorder.

The modified antibody of the present invention is administered by any suitable means, including parenteral, subcutaneous, intraperitoneal, intrapulinonary, and intranasal, and, if desired for local immunosuppressive treatment, intralesional administration. Parenteral infusions include intramuscular, intravenous, intraarterial, intraperitoneal, or subcutaneous administration. In addition, the antagonist may suitably be administered by pulse infusion, e.g., with declining doses of the antagonist. Preferably the dosing is given by injections, most preferably intravenous or subcutaneous injections, depending in part on whether the administration is brief or chronic.

According to the invention other compounds, such as cytotoxic agents, chemotherapeutic agents, immunosuppressive agents and/or cytokines are administered with the antagonists herein. The combined administration includes coadministration, using separate formulations or a single pharmaceutical formulation, and consecutive administration in either order, wherein preferably there is a time period while both (or all) active agents simultaneously exert their biological activities.

It would be clear that the dose of the composition of the invention required to achieve cures may be further reduced with schedule optimization.

In accordance with the practice of the invention, the pharmaceutical carrier may be a lipid carrier. The lipid carrier may be a phospholipid. Further, the lipid carrier may be a fatty acid. Also, the lipid carrier may be a detergent. As used herein, a detergent is any substance that alters the surface tension of a liquid, generally lowering it.

In one example of the invention, the detergent may be a nonionic detergent. Examples of nonionic detergents include, but are not limited to, polysorbate 80 (also known as Tween 80 or (polyoxyethylenesorbitan monooleate), Brij, and Triton (for example Triton WR-1339 and Triton A-20).

Alternatively, the detergent may be an ionic detergent. An example of an ionic detergent includes, but is not limited to, alkyltrimethylammonium bromide.

Additionally, in accordance with the invention, the lipid carrier may be a liposome. As used in this application, a "liposome" is any membrane bound vesicle which contains any molecules of the invention or combinations thereof.

EXEMPLARY EMBODIMENTS

1. An antibody comprising a variant heavy chain region comprising at least one amino acid substitution relative to the parent non-substituted heavy chain region, wherein the heavy chain region of the parent non-substituted antibody comprises at least one of the amino acid residues selected from the group consisting of Val11 (Kabat numbering), Leu11 (Kabat numbering) and Pro151 (EU numbering), and wherein said substitution is at one of said amino acid residues selected from the group consisting of Val11, Leu11 and Pro151, and wherein direct cell death induced by the antibody comprising the variant heavy chain region is altered compared to direct cell death induced by the antibody comprising the parent non-substituted heavy chain region.

2. The antibody according to embodiment 1, wherein at least one of the amino acid residues selected from the group consisting of Val11, Leu11 and Pro151 is substituted with at least one of the amino acid residues selected from the group consisting of alanine, glycine, phenylalanine, threonine and tryptophan.

3. The antibody according to any one of embodiments 1 or 2, wherein the antibody is an IgG1 antibody.

4. The antibody according to any one of embodiments 1 to 3, wherein the parent non-substituted antibody is an anti-CD20 antibody.

5. The antibody according to any one of embodiments 1 to 4, wherein the parent non-substituted antibody is a type I anti-CD20 antibody.

6. The antibody according to any one of embodiments 1 to 5, wherein the parent non-substituted antibody is a type II anti-CD20 antibody.

7. The antibody according to any one of embodiments 1 to 4 or 6, wherein the parent non-substituted antibody is obinutuzumab.

8. The antibody according to any one of embodiments 1 to 5, wherein the parent non-substituted antibody is rituximab.

9. The antibody according to any one of embodiments 1 to 8, wherein direct cell death induced by the antibody comprising the variant heavy chain region is increased compared to direct cell death induced by the antibody comprising the parent non-substituted heavy chain region.

10. The antibody according to any one of embodiments 1 to 8, wherein direct cell death induced by the antibody comprising the variant heavy chain region is decreased compared to direct cell death induced by the antibody comprising the parent non-substituted heavy chain region.

11. The antibody according to embodiment 10, wherein at least one of the amino acid residues selected from the group consisting of Val11, Leu11 and Pro151 is substituted with at least one of the amino acid residues selected from the group consisting of alanine and glycine.

12. The antibody according to embodiment 9, wherein at least one of the amino acid residues selected from the group consisting of Val11, Leu11 and Pro151 is substituted with at least one of the amino acid residues selected from the group consisting of phenylalanine, threonine and tryptophan.

13. The antibody according to embodiment 12, wherein the amino acid residue Pro151 is substituted with phenylalanine.

14. The antibody according to any one of embodiments 1 to 13, wherein the parent non-substituted heavy chain region comprises the amino acid residues Leu234 (EU numbering), Leu235 (EU numbering) and Pro329 (EU numbering), wherein the variant heavy chain region comprises at least one of the amino acid substitutions Leu234Ala, Leu235Ala and Pro329Gly relative to the parent non-substituted heavy chain region, wherein binding to FcγR and C1q is abolished and wherein Fc-mediated effector function is abolished.

15. The antibody according to embodiment 14, wherein the variant heavy chain region comprises the amino acid substitutions Leu234Ala, Leu235Ala and Pro329Gly relative to the parent non-substituted heavy chain region.

16. The antibody according to any one of embodiments 1 to 15 with an amount of fucose of 60% or less of the total amount of oligosaccharides (sugars) at the amino acid residue Asn297 in the heavy chain region.

17. The antibody according to any one of embodiments 1 to 16, wherein the antibody specifically binds to CD20.

18. The antibody according to any one of embodiments 1 to 17, wherein the antibody binds to CD20 with a dissociation constant (Kd) on cells of 10 nM or less as determined by scatchard analysis.

19. A polynucleotide encoding a variant heavy chain region of an antibody of any one of embodiments 1 to 18.

20. A polynucleotide encoding a light chain region of an antibody of any one of embodiments 1 to 18.

21. A vector comprising at least one of the polynucleotides according to the embodiments 19 and 20.

22. The vector of embodiment 21 which is polycistronic.

23. A host cell comprising one of the vectors according to embodiments 21 and 22 or at least one of the polynucleotides according to the embodiments 19 and 20.

24. The host cell of embodiment 23, wherein said host is engineered to express at least one polynucleotide encoding a polypeptide having β(1,4)-N-acetylglucosaminyltransferase III activity.

25. The host cell of embodiment 24, wherein said polypeptide having β(1,4)-N-acetylglucosaminyltransferase III activity is a fusion polypeptide further comprising the Golgi localization domain of a heterologous Golgi resident polypeptide.

26. The host of embodiment 25, wherein said Golgi localization domain is selected from the localization domain of mannosidase II, the localization domain of β(1,2)-N-acetylglucosaminyltransferase I, the localization of β(1,2)-N-acetylglucosaminyltransferase II, the localization domain of mannosidase I, and the localization of α1-6 core fucosyltransferase.

27. A method for the production of an antibody of any one of embodiments 1 to 18 comprising (i) culturing the host cell of any one of embodiments 23 to 26 under conditions permitting the expression of said at least one polynucleotide; and (ii) recovering said antibody from the culture medium.

28. A pharmaceutical composition comprising an antibody according to any one of embodiments 1 to 18 and a pharmaceutically acceptable carrier.

29. An antibody according to any one of embodiments 1 to 18 for use as a medicament.

30. An antibody according to any one of embodiments 1 to 18 for use in treating a disease selected from the group consisting of proliferative disorder and autoimmune disease.

31. An antibody for use according to embodiment 30, characterized in that said proliferative disorder is a CD20 expressing cancer.

32. An antibody for use according to embodiment 31, characterized in that said cancer is selected from the group consisting of lymphoma and lymphocytic leukemia.

33. An antibody for use according to embodiment 30, characterized in that said autoimmune disease is selected from the group consisting of rheumatoid arthritis, lupus, multiple sclerosis, Sjögren's syndrome and transplant rejection.

34. A method for treating a disease selected from the group consisting of proliferative disorder and autoimmune disease comprising administering to an individual an effective amount of the antibody according to any one of embodiments 1 to 18.

35. The method according to embodiment 34, characterized in that said proliferative disorder is a CD20 expressing cancer.

36. The method according to embodiment 35, characterized in that said cancer is selected from the group consisting of lymphoma and lymphocytic leukemia.

37. The method according to embodiment 34, characterized in that said autoimmune disease is selected from the group consisting of rheumatoid arthritis, lupus, multiple sclerosis, Sjögren's syndrome and transplant rejection.

38. Use of the antibody according to any one of embodiments 1 to 18 for the manufacture of a medicament.

39. The use of embodiment 38, wherein the medicament is for treatment of a disease selected from the group consisting of proliferative disorder and autoimmune disease.

40. The use of embodiment 39, characterized in that said proliferative disorder is a CD20 expressing cancer.

41. The use of embodiment 40, characterized in that said cancer is selected from the group consisting of lymphoma and lymphocytic leukemia.

42. The use of embodiment 41, characterized in that said autoimmune disease is selected from the group consisting of rheumatoid arthritis, lupus, multiple sclerosis, Sjögren's syndrome and transplant rejection.

The examples below explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those disclosed herein will become apparent to those skilled in the art from the foregoing description and accompanying figures. Such modifications are intended to fall within the scope of the appended claims.

III. Examples

The following are examples of methods and compositions of the invention. It is understood that various other embodiments may be practiced, given the general description provided herein.

Example 1

Antibodies

For the experiments disclosed below antibodies against CD20 (obinutuzumab (GA101), recommended INN, WHO Drug Information, Vol. 26, No. 4, 2012, p. 453 and rituximab, U.S. Pat. No. 7,381,560 and EP2000149B1) were used. All variants disclosed herein, GA101-V11A, GA101-V11G, GA101-V11T, GA101-V11F, GA101-V11W, GA101-Ser114del, GA101-Ser114ins, GA101-P151A, GA101-P151F, GA101-hinge ins, GA101-hinge del, GA101-P329F, GA101-V11F P329G L234A L235A, GA101-P329G L234A L235A, GA101-P151F P329G L234A L235A, GA101-hinge del P329G L234A L235A, GA101-V11F P151F, GA101-P151F hin del and GA101-V11F P151F hinge del were generated using PCR based mutagenesis. IgG molecules were expressed in the HEK-EBNA or HEK293 system, and purified using protein A and size exclusion chromatography.

Example 2

Direct Cell Death Induction of Tumor Targets by Obinutuzumab CH1, VH and Fc Variants The induction of direct cell death by obinutuzumab variants was tested using CD20-expressing mantle cell lymphoma (Z-138). Briefly, cells were harvested, counted, checked for viability and re-suspended at $0.556 \times 10^6$ cells/ml in RPMI1640+10% FCS+1% Glutamax. 180 µl of cell suspension (containing 0.1×10⁶ cells) were incubated in round-bottom 96-well plate for 20 hours to 24 hours at 37° C. and 5% $CO_2$ in the cell incubator with different concentrations of the obinutuzumab variants (10 ng/ml-10 µg/ml). Afterwards, the cells were washed once with Annexin V Binding Buffer (10 mM HEPES/NAOH pH7.4, 140 mM NaCl, 2.5 mM $CaCl_2$)) before incubation for 30 min at 4° C. in the dark with 100 µl/well Annexin V FLUOS (Roche #11828681001, pre-diluted in Annexin V Binding Buffer 1:75). The cells were washed by addition of 80 µl/well Annexin V Binding Buffer and immediately analyzed by FACS using a FACS CantoII (Software FACS Diva) after addition of pre-diluted PI solution (Sigma Aldrich #P4864, 1:4000).

FIG. 1 A and FIG. 1B shows the induction of Phosphatidylserine surface expression on Z-138 as measured by Annexin V binding as well as PI staining in the presence of different obinutuzumab elbow hinge variants. 5 out of 14 tested elbow hinge variants induced significantly higher direct cell death of Z-138 compared to wildtype obinutuzumab. The 5 superior variants were: V11T, V11F, V11W, P151F and hinge del.

The superior direct cell death induction was independent of the Fc part of obinutuzumab comparing selected wildtype to P329G L234A L235A elbow hinge variants (FIG. 1 C).

FIG. 1 D shows that combination of selected elbow hinge variations in an obinutuzumab P329G L234A L235A-based IgG did not further improve direct cell death induction compared to the single variants. Obinutuzumab V11F and obinutuzumab P151F performed equally well and were superior to obinutuzumab hin del. Obinutuzumab V11F P151F was inferior to the corresponding single variants in terms of maximal direct cell death induction during 24 h incubation. The same was true for combinations of V11F or P151F with hin del. Table 1 provides the corresponding EC50 values calculated with GraphPad Prism. The extra sum-of-squares F test revealed no significant differences with exception of obinutuzumab hin del compared to obinutuzumab P151F hin del.

TABLE 1

EC50 (ng/ml) values of direct cell death induction using Z-138 (% total AnnV positive cells)

|  | EC50 (ng/ml) |
| --- | --- |
| obinutuzumab V11F | 130.8 |
| obinutuzumab P151F | 133.1 |
| obinutuzumab hin del | 154.7 |
| obinutuzumab V11F P151F | 111.9 |
| obinutuzumab P151F hin del | 68.4 |
| obinutuzumab V11F P151F hin del | ~171.0 |

Example 3

B Cell Depletion in Human Whole Blood Mediated by Obinutuzumab CH1 and VH Variants Normal B cell depletion mediated by obinutuzumab Fc and elbow hinge variants was also assessed using fresh heparinized human blood from healthy volunteers. Briefly, fresh blood was collected in heparin-containing syringes. Blood aliquots (190 4/well) were placed in 96-deep well plates, supplemented with obinutuzumab IgG variant dilutions (10 4/well) and incubated for 20 hours to 24 hours at 37° C. in 5% $CO_2$ in a humidified cell incubator. After incubation, blood was mixed by pipetting up and down before 35 4/well blood aliquots were transferred in 96-round-bottom plates and incubated with fluorescent anti-CD45 (Anti-human CD45 FITC, BD #555482), anti-CD19 (Anti-human CD19 PerCPCy5.5, Biolegend #302230) and anti-CD3 (Anti-human CD3 APCCy7, Biolegend #300318) in total 55 4 volume for flow cytometry. After 15 min incubation at room temperature (in the dark) 200 4/well of FACS lysis solution (BD Biosciences) was added to deplete erythrocytes and to fix cells prior to flow cytometry using a BD FACSCantoII.

Figure 2:
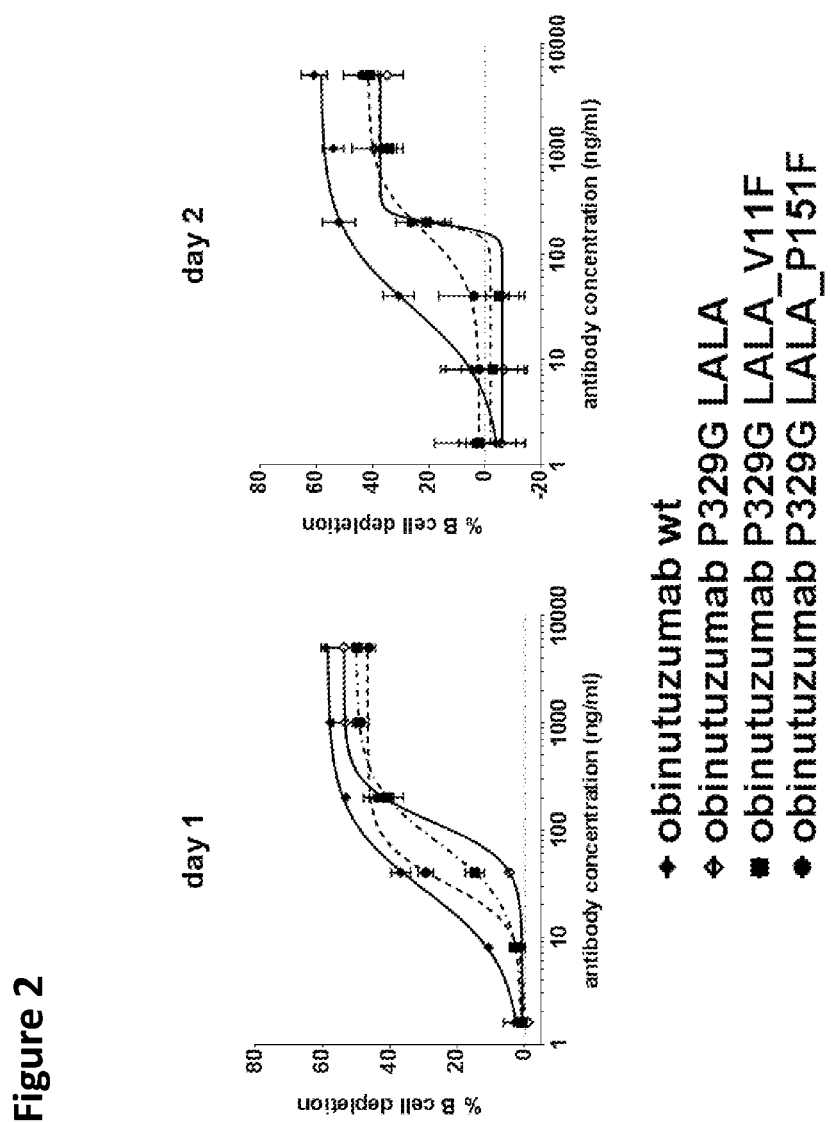

FIG. 2 shows that the obinutuzumab variant GA101-P151F P329G L234A L235A was superior in mediating B cell depletion compared to the GA101-P329G L234A L235A in terms of EC50 especially after 1 day incubation. The P151F elbow hinge variant was also superior to the obinutuzumab variant GA101-V11F P329G L234A L235A which was slightly superior to GA101-P329G L234A L235A after 1 day of incubation but not after 2 days. Obinutuzumab was superior to all P329G L234A L235A variants in this assay. Table 2 shows the corresponding EC50 values.

TABLE 2

EC50 (ng/ml) of B cell depletion

|  | EC50 (ng/ml)_day 1 | EC50 (ng/ml)_day 2 |
| --- | --- | --- |
| obinutuzumab wt | 27.6 | 31.5 |
| obinutuzumab P329G L234A L235A | 117.9 | 191.5 |
| obinutuzumab P329G L234A L235A V11F | 75.3 | 192.5 |
| obinutuzumab P329G L234A L235A P151F | 31.9 | 163.6 |

Example 4

For determination of the PK properties of GA101-V11F P329G L234A L235A and GA101-P151F P329G L234A L235A in direct comparison to GA101-P329G L234A L235A, SCID beige mice were injected intravenously with 1 mg/kg of the respective antibodies. Blood was taken and plasma samples were analyzed with a platform ECLIA method specific for human CH1/kappa domain using a Cobas e411 instrument. Briefly, to test plasma samples of compounds GA101-P329G L234A L235A, GA101-P151F P329G L234A L235A or GA101-V11F P329G L234A L235A, a) capture antibody mAb<H-Fab(kappa)>M-1.7.10-IgG-Bi, b) detection antibody mAb<H-Fab(CH1)>M-1.19.31-IgG-Ru, and c) SA-beads are added stepwise to a detection vessel and incubated for 9 minutes in each step. Finally, the SA-beads-bound complex is detected by a measuring cell which records the counts of SA-beads in replicate. The counts are proportional to the analyte concentration in the test sample.

Figure 3:
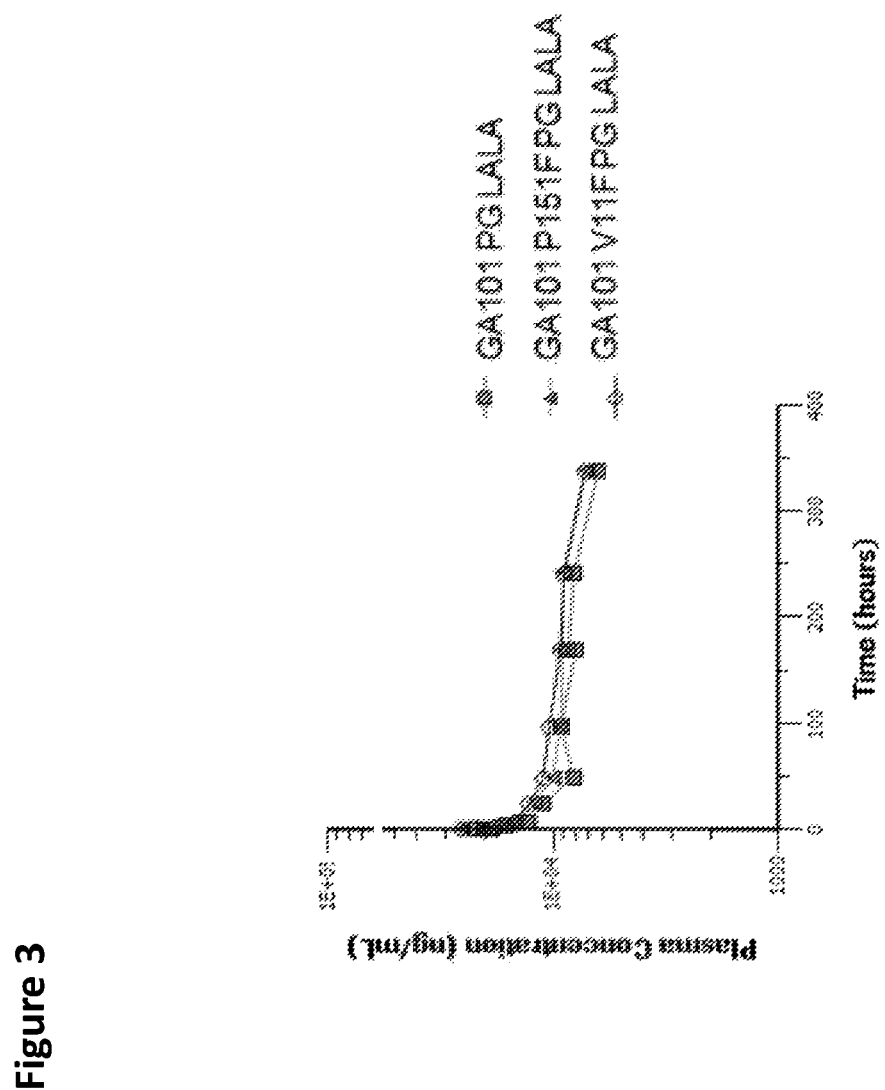

GA101-V11F P329G L234A L235A and GA101-P151F P329G L234A L235A showed pharmacokinetic properties typical for human monoclonal antibodies of IgG1 isotype in terms of clearance and half life and were both comparable to GA101-P329G L234A L235A as shown by FIG. 3.

Example 5

Antitumor Activity of a Type II Anti-CD20 Antibody Obinutuzumab (GA101), GA101-P329G L234A L235A, GA101-V11F P329G L234A L235A and GA101-P151F P329G L234A L235A Test Agents The antibodies were provided as stock solution from Roche Glycart AG, Schlieren, Switzerland, in histidine buffers with different additives. The antibody was diluted with 0.9% NaCl solution prior to in vivo application.

Cell Lines and Culture Conditions

The human SU-DHL-4 lymphoma cell line was cultured in RPMI 1640 supplemented with 10% fetal bovine serum (PAA Laboratories, Austria) and 2 mM L-glutamine at 37° C. in a water-saturated atmosphere at 5% $CO_2$. For in-vivo xenograft experiments the cells were co-injected with Matrigel.

Animals

Female SCID beige mice, age 5 weeks at arrival (purchased from Charles River, Sulzfeld, Germany), were maintained in the quarantine part of the animal facility for one week and afterwards under specific-pathogen-free condition with daily cycles of 12 h light/12 h darkness according to guidelines (GV-Solas; Felasa; TierschG). The experimental study protocol was reviewed and approved by Roche and the local government (Regierung von Oberbayern; registration no. 55.2-1-54-2531.2-26-09). Diet food (KLIBA NAFAG 3807) and water (filtered) were provided ad libitum.

Induction of SC SU-DHL-4 Tumors in SCID Beige Mice

Five millions ($5 \times 10^6$) SU-DHL-4 tumor cells in 100 µl of PBS with matrigel (50:50, BD Biosciences, France) were subcutaneously (SC) injected into the right flank of female SCID beige mice.

Monitoring

Animals were monitored daily for clinical symptoms and detection of adverse effects. During the experiment the body weight of animals was checked two times a week and tumor volume was measured by caliper.

Treatment of Animals

Animal treatment started at the day of randomization 20 days after tumor cell inoculation. Humanized type II anti-CD20 antibody obinutuzumab (GA101), rituximab, GA101-P329G L234A L235A, GA101-V11F P329G L234A L235A and GA101-P151F P329G L234A L235A was administered as single agent i.p. q7d once weekly (day 20, 27, 34 and 41) for 4 weeks at a dosage of 30 mg/kg. The corresponding vehicle was administered on the same days.

Tumor Growth Inhibition (TGI) on Day 48

Monotherapy treatment using GA101-P329G L234A L235A, GA101-V11F P329G L234A L235A, GA101-P151F P329G L234A L235A resulted in tumor growth inhibition of 59%, 64% or 79%, respectively (based on medians). Obinutuzumab or rituximab treatment showed tumor regression (TGI>100%) on day 48 after tumor cell inoculation.

Nonparametric Treatment-to-Control-Ratios (TCRnpar) on Day 48

Nonparametric Treatment-to-Control-Ratios (TCRnpar) and the two-sided nonparametric confidence intervals (CI) was calculated based on baseline corrected data by ratio to assess statistical significance on day 48 after tumor cell inoculation. Each treatment was statistically significant compared to the control group.

TABLE 3

Summary of antitumor activity according to FIG. 4

| Treatment schedule | TGI (%) | np TCR compared to vehicle | [95% CI] | Tumor free Animals on Day 48 |
| --- | --- | --- | --- | --- |
| Vehicle | — | — | [—] | 0 |
| obinutuzumab once weekly; 30 mg/kg × 4 | >100 | 0 | [0-0.01] | 8 |
| GA101 P329G L234A L235A once weekly; 30 mg/kg × 4 | 59 | 0.50 | [0.39-0.60] | 0 |
| GA101 V11F P329G L234A L235A once weekly; 30 mg/kg × 4 | 64 | 0.45 | [0.31-0.60] | 0 |
| GA101 P151F P329G L234A L235A once weekly; 30 mg/kg × 4 | 80 | 0.30 | [0.22-0.39] | 0 |
| rituximab once weekly; 30 mg/kg × 4 | >100 | 0.03 | [0-0.45] | 2 |

Although, the foregoing invention has been disclosed in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An antibody comprising a variant heavy chain region comprising at least one amino acid substitution relative to the parent non-substituted heavy chain region of a parent non-substituted antibody,
   wherein the amino acid residue Pro151 is substituted with phenylalanine, and
   wherein the parent non-substituted antibody is obinutuzumab, and
   wherein direct cell death induced by the antibody comprising the variant heavy chain region is altered compared to direct cell death induced by the antibody comprising the parent non-substituted heavy chain region.

2. The antibody according to claim 1, wherein direct cell death induced by the antibody comprising the variant heavy chain region is increased compared to direct cell death induced by the antibody comprising the parent non-substituted heavy chain region.

3. The antibody according to claim 1, wherein direct cell death induced by the antibody comprising the variant heavy chain region is decreased compared to direct cell death induced by the antibody comprising the parent non-substituted heavy chain region.

4. The antibody according to claim 1, wherein the parent non-substituted heavy chain region comprises the amino acid residues Leu234 (EU numbering), Leu235 (EU numbering) and Pro329 (EU numbering), wherein the variant heavy chain region comprises at least one of the amino acid substitutions Leu234Ala, Leu235Ala and Pro329Gly relative to the parent non-substituted heavy chain region, wherein binding to FcγR and C1q is abolished and wherein Fc-mediated effector function is abolished.

5. A pharmaceutical composition comprising an antibody according claim 1 and a pharmaceutically acceptable carrier.

\* \* \* \* \*